(12) United States Patent
Salituro et al.

(10) Patent No.: US 7,329,652 B2
(45) Date of Patent: Feb. 12, 2008

(54) DIAMINOTRIAZOLE COMPOUNDS USEFUL AS PROTEIN KINASE INHIBITORS

(75) Inventors: Francesco Salituro, Marlboro, MA (US); Mark Ledeboer, Acton, MA (US); Brian Ledford, Attleboro, MA (US); Jian Wang, Newton, MA (US); Albert Pierce, Cambridge, MA (US); John Duffy, Northborough, MA (US); David Messersmith, Somerville, MA (US)

(73) Assignee: Vertex Pharamaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/230,221

(22) Filed: Sep. 19, 2005

(65) Prior Publication Data

US 2006/0063756 A1    Mar. 23, 2006

Related U.S. Application Data

(60) Provisional application No. 60/610,902, filed on Sep. 17, 2004.

(51) Int. Cl.
*A61K 31/551* (2006.01)
*A61K 31/553* (2006.01)
*A61K 31/5377* (2006.01)
*A61K 31/496* (2006.01)
*C07D 413/02* (2006.01)
*C07D 403/02* (2006.01)
*C07D 267/10* (2006.01)
*C07D 239/24* (2006.01)
*C07D 413/12* (2006.01)

(52) U.S. Cl. .............. 514/211.15; 514/217.09; 514/218; 514/254.05; 514/235.5; 514/326; 514/383; 540/524; 540/544; 540/137; 540/330; 546/210; 548/265.2; 548/264.8

(58) Field of Classification Search ........... 514/211.15, 514/217.09, 218, 254.05, 235.5, 326, 383; 540/524, 544; 544/137, 330; 546/210; 548/265.2, 548/264.8
See application file for complete search history.

(56) References Cited

U.S. PATENT DOCUMENTS

2004/0214817 A1* 10/2004 Pierce et al. ........... 514/217.09

FOREIGN PATENT DOCUMENTS

| WO | WO 2004/046120 A2 | 6/2004 |
| WO | WO 2004/052280 A2 | 6/2004 |
| WO | WO 2004/058753 A1 | 7/2004 |
| WO | WO 2005/013982 A1 | 2/2005 |

* cited by examiner

*Primary Examiner*—Rebecca Anderson
*Assistant Examiner*—Yong Chu
(74) *Attorney, Agent, or Firm*—Karen E. Brown

(57) ABSTRACT

The present invention relates to inhibitors of protein kinases, particularly to inhibitors of JAK2 and JAK3. The invention also provides pharmaceutical compositions comprising the compounds of the invention, processes for preparing the compounds and methods of using the compositions in the treatment of various disorders.

15 Claims, No Drawings

DIAMINOTRIAZOLE COMPOUNDS USEFUL AS PROTEIN KINASE INHIBITORS

This application claims the benefit of priority of U.S. Provisional Application 60/610,902, filed Sep. 17, 2004, which is herein incorporated by reference.

TECHNICAL FIELD OF THE INVENTION

The present invention relates to compounds useful as inhibitors of Janus kinases (JAK). The present invention also relates to compounds useful as inhibitors of Aurora-2 kinase, Flt3 kinase, GSK-3 kinase and KDR. The invention also provides pharmaceutically acceptable compositions comprising the compounds of the invention and methods of using the compositions in the treatment of various disorders.

BACKGROUND OF THE INVENTION

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. JAK2 has also been implicated in myeloproliferative disorders, which include polycythemia vera, essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

WO2004/046120 describes diaminotriazoles useful as inhibitors of protein kinases, including Flt3, FMS, c-Kit, PDGFR, JAK, AGC sub-family of protein kinases, CDK, GSK, Src, ROCK and/or Syk. However, there is a need to develop compounds that are more selective inhibitors of protein kinases, such as those that inhibit Aurora-2, Flt3, KDR, JAK2 and JAK3. In particular, it would be desirable to develop compounds that are useful as inhibitors of JAK family kinases.

SUMMARY OF THE INVENTION

It has now been found that compounds of this invention, and pharmaceutically acceptable compositions thereof, are effective as inhibitors of protein kinases. In certain embodiments, these compounds, and pharmaceutically acceptable compositions thereof, are effective as inhibitors of GSK-3, JAK-2, JAK-3, Flt3, KDR or Aurora-2 protein kinases. In preferred embodiments, these compounds and pharmaceutically acceptable compositions are inhibitors of JAK-2 or JAK-3. These compounds have the general formula I:

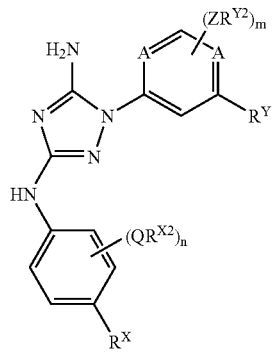

or a pharmaceutically acceptable derivative thereof, wherein the variables are as defined herein.

These compounds and pharmaceutical compositions thereof are useful for treating or preventing a variety of disorders, including, but not limited to, allergies, asthma, autoimmune diseases such as transplant rejection, rheumatoid arthritis, amyotrophic lateral sclerosis and multiple sclerosis, as well as in solid and hematologic malignancies such as leukemias and lymphomas. The compounds and pharmaceuticals compositions thereof are also useful in treating or preventing myeloproliferative disorders, including polycythemia vera, essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999; "March's Advanced Organic Chemistry", 5$^{th}$ Ed., Ed.: Smith, M. B. and March, J., John Wiley & Sons, New York: 2001; "Encyclopedia of Organic Transformations"; Ed.: Richard C. Larock, John Wiley & Sons, New York: 1999; "Encyclopedia of Reagents for Organic Synthesis" Ed.: Leo A. Paquette, John Wiley & Sons, New York: 1995; T. W. Greene & P. G. M Wutz, "Protective Groups in Organic Synthesis", 3$^{rd}$ Edition, John Wiley & Sons, Inc. (1999)(and earlier editions) the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted-hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle", "cycloaliphatic", or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle", or "cycloalkyl") refers to a monocyclic $C_{3-8}$ hydrocarbon or bicyclic $C_{8-12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl, or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocyclic rings include benzimidazolone (e.g., 3-1H-benzimidazol-2-one, 3-(1-alkyl)-benzimidazol-2-one), tetrahydrofuranyl (e.g., 2-tetrahydrofuranyl, 3-tetrahydrofuranyl), tetrahydrothiophenyl (e.g., 2-tetrahydrothiophenyl, 3-tetrahydrothiophenyl), morpholino (e.g., 2-morpholino, 3-morpholino, 4-morpholino), thiomorpholino (e.g., 2-thiomorpholino, 3-thiomorpholino, 4-thiomorpholino), pyrrolidinyl (e.g., 1-pyrrolidinyl, 2-pyrrolidinyl, 3-pyrrolidinyl), tetrahydropiperazinyl (e.g., 1-tetrahydropiperazinyl, 2-tetrahydropiperazinyl, 3-tetrahydropiperazinyl), piperidinyl (e.g., 1-piperidinyl, 2-piperidinyl, 3-piperidinyl, 4-piperidinyl), pyrazolinyl (e.g., 1-pyrazolinyl, 3-pyrazolinyl, 4-pyrazolinyl, 5-pyrazolinyl), thiazolidinyl (e.g., 2-thiazolidinyl, 3-thiazolidinyl, 4-thiazolidinyl), imidazolidiny (e.g., 1-imidazolidinyl, 2-iridazolidinyl, 4-imidazolidinyl, 5-imidazolidinyl), indolinyl, tetrahydroquinolinyl, tetrahydroisoquinolinyl, benzothiolane, benzodithiane, and dihydro-imidazol-2-one (1,3-dihydro-imidazol-2-one).

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl), or $NR^+$ (as in N-substituted pyrrolidinyl)).

The term "unsaturated", as used herein, means that a moiety has one or more units of unsaturation.

The term "alkoxy" or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl", and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

Examples of heteroaryl rings include furanyl (e.g., 2-furanyl, 3-furanyl), imidazolyl (e.g., N-imidazolyl, 2-imidazolyl, 4-imidazolyl, 5-imidazolyl)benzimidazolyl, isoxazolyl (e.g., 3-isoxazolyl, 4-isoxazolyl, 5-isoxazolyl) oxazolyl (e.g., 2-oxazolyl, 4-oxazolyl, 5-oxazolyl), pyrrolyl, (e.g., N-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), tetrazolyl (e.g., 5-tetrazolyl), triazolyl (e.g., 2-triazolyl and 5-triazolyl), thienyl, (e.g., 2-thienyl, 3-thienyl), benzofuryl, thiophenyl, benzothiophenyl, indolyl (e.g., 2-indolyl), pyrazolyl (e.g., 2-pyrazolyl), isothiazolyl, oxadiazolyl (e.g., 1,2,3-oxadiazolyl), oxadiazolyl (e.g., 1,2,5-oxadiazolyl), oxadiazolyl (e.g., 1,2,4-oxadiazolyl), triazolyl (e.g., 1,2,3-triazolyl), thiadiazolyl (e.g., 1,2,3-thiadiazolyl), thiadiazolyl (e.g., 1,3,4-thiadiazolyl), thiadiazolyl (e.g., 1,2,5-thiadiazolyl), purinyl, pyrazinyl, triazinyl (e.g., 1,3,5-triazinyl), quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph) optionally substituted with R°; —CH=CH(Ph) optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —C(=NH)—N(R°)$_2$, —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$^2$)$_{0-2}$NHC(O)R° wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of R° are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic), wherein each of the foregoing C$_{1-4}$ aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic), wherein each of the foregoing C$_{1-4}$ aliphatic groups of R* is unsubstituted.

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic), wherein each of the foregoing C$_{1-4}$ aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R$^+$, or any other variable similarly defined herein), are taken together together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

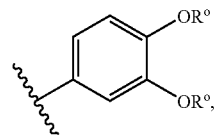

these two occurrences of R° are taken together with the oxygen atoms to which they are bound to form a fused 6-membered oxygen containing ring:

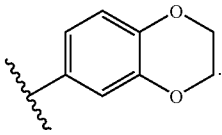

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a $^{12}C$ carbon by a $^{13}C$ or $^{14}C$ carbon are within the scope of this invention. Such compounds are useful, for example, as analytical tools or probes in biological assays.

Description of Compounds of the Invention

The invention provides a compound of formula I:

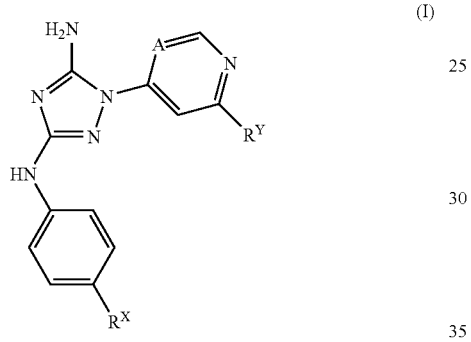

or a pharmaceutically acceptable salt, derivative or prodrug thereof, wherein:

A is N or $CR^1$;

$R^1$ is H, halogen or a $C_{1-6}$ alkyl;

$R^X$ is selected from

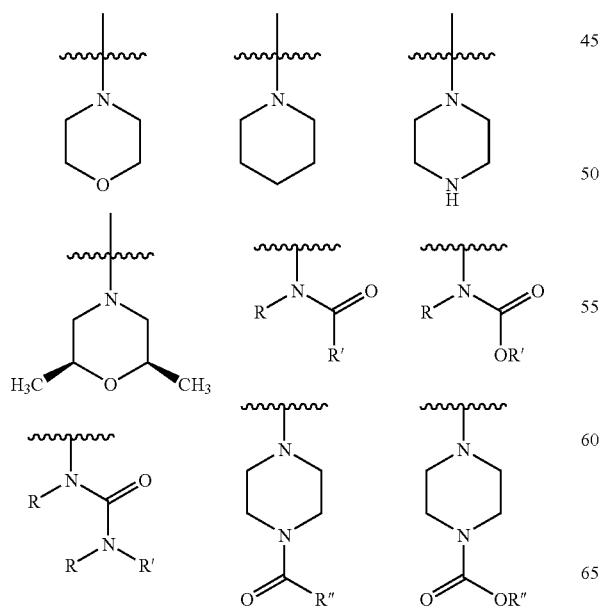

$R^Y$ is selected from

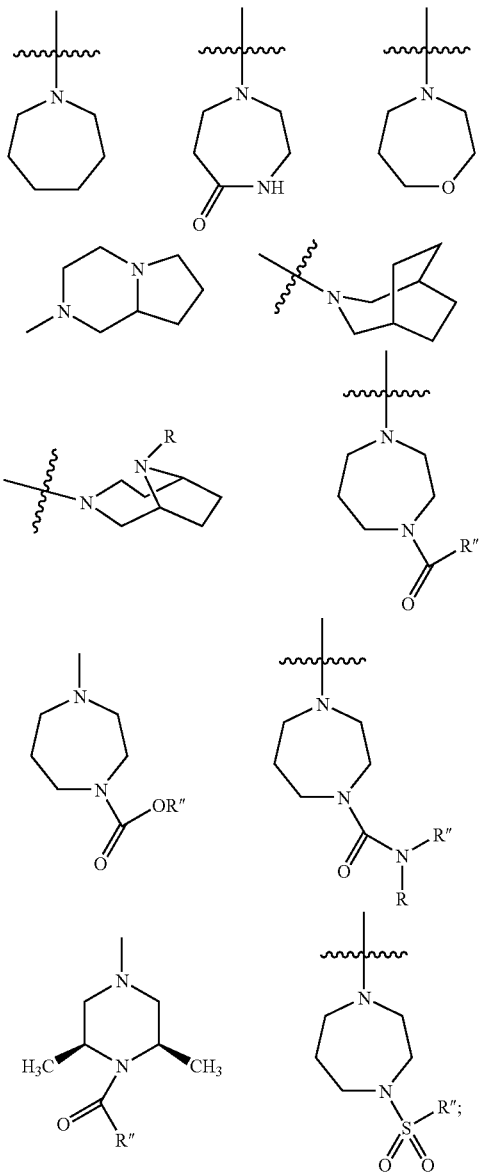

each occurrence of R is independently selected from hydrogen or a $C_{1-6}$ aliphatic group optionally substituted with J or J'; and R' is independently selected from hydrogen or a group selected from $C_{1-8}$ aliphatic optionally substituted with up to three occurrences of J or J', $C_{6-10}$ aryl optionally substituted with up to three occurrences of J, a heteroaryl ring having 5-10 ring atoms optionally substituted with up to three occurrences of J, or a heterocyclyl ring having 3-10 ring atoms optionally substituted with up to three occurrences of J or J', or wherein R and R' taken together, form a 5-8 membered cycloalkyl, heterocyclyl, aryl, or heteroaryl ring having 0-3 heteroatoms independently selected from nitrogen, oxygen, or sulfur, each ring being optionally and independently substituted with up to three occurrences of J;

each occurrence of R" is independently selected from hydrogen or a group selected from $C_{1-8}$ aliphatic optionally substituted with up to three occurrences of J or J', $C_{6-10}$ aryl optionally substituted with up to three occurrences of J, a heteroaryl ring having 5-10 ring atoms optionally substituted with up to three occurrences of J, or a heterocyclyl ring having 3-10 ring atoms optionally substituted with up to three occurrences of J or J', or wherein R and R" taken together, form a 5-8 membered cycloalkyl, heterocyclyl, aryl, or heteroaryl ring having 0-3 heteroatoms independently selected from nitrogen, oxygen, or sulfur, each ring being optionally and independently substituted with up to three occurrences of J;

each occurrence of J is independently selected from halogen; —R°; —OR°; —SR°; 1,2-methylenedioxy; 1,2-ethylenedioxy; phenyl (Ph) optionally substituted with R°; —O(Ph) optionally substituted with R°; —$(CH_2)_{1-2}$(Ph) optionally substituted with R°; —CH=CH(Ph) optionally substituted with R°; —$NO_2$; —CN; —N(R°)$_2$; —NR°C(O)R°; —NR°C(S)R°; —NR°C(O)N(R°)$_2$; —NR°C(S)N(R°)$_2$; —NR°$CO_2$R°; —NR°NR°C(O)R°; —NR°NR°C(O)N(R°)$_2$; —NR°NR°$CO_2$R°; —C(O)C(O)R°; —C(O)C(O)OR°, —C(O)C(O)N(R°)$_2$, —C(O)$CH_2$C(O)R°; —$CO_2$R°; —C(O)R°; —C(S)R°; —C(S)OR°, —C(O)N(R°)$_2$; —C(S)N(R°)$_2$; —C(=NH)—N(R°)$_2$, —OC(O)N(R°)$_2$; —OC(O)R°; —C(O)N(OR°)R°; —C(NOR°)R°; —S(O)$_2$R°; —S(O)$_3$R°; —$SO_2$N(R°)$_2$; —S(O)R°; —NR°$SO_2$N(R°)$_2$; —NR°$SO_2$R°; —N(OR°)R°; —C(=NH)—N(R°)$_2$; C(=NOR°)R°; $(CH_2)_{0-2}$NHC(O)R°; —P(O)$_2$R°; —PO(R°)$_2$; —OPO(R°)$_2$; or —P(O)(H)(OR°);

wherein each independent occurrence of R° is selected from hydrogen, optionally substituted $C_{1-6}$ aliphatic, optionally substituted 5-6 membered heteroaryl or heterocyclic ring, optionally substituted phenyl (Ph); optionally substituted —O(Ph); optionally substituted —$(CH_2)_{1-2}$(Ph); optionally substituted —CH=CH(Ph); or, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur;

wherein a substituent for an aliphatic group of R° is optionally substituted heteroaryl, optionally substituted, heterocyclic, $NH_2$, NH($C_{1-6}$ aliphatic), N($C_{1-6}$ aliphatic)$_2$, halogen, $C_{1-6}$ aliphatic, OH, O($C_{1-6}$ aliphatic), $NO_2$, CN, $CO_2$H, $CO_2$($C_{1-6}$ aliphatic), O(halo $C_{1-6}$ aliphatic), or halo($C_{1-6}$ aliphatic), wherein each of these $C_{1-6}$ aliphatic groups of R° is unsubstituted;

wherein a substituent for a phenyl, heteroaryl or heterocyclic group of R° is $C_{1-6}$ aliphatic, $NH_2$, NH($C_{1-4}$ aliphatic), N($C_{1-6}$ aliphatic)$_2$, halogen, $C_{1-6}$ aliphatic, OH, O($C_{1-6}$ aliphatic), $NO_2$, CN, $CO_2$H, $CO_2$($C_{1-6}$ aliphatic), O(halo $C_{1-6}$ aliphatic), or halo($C_{1-6}$ aliphatic), wherein each of these $C_{1-6}$ aliphatic groups of R° is unsubstituted;

each occurrence of J' is independently selected from =O, =S, =NNHR*, =NN(R*)$_2$, =NNHC(O)R*, =NNHCO$_2$ (alkyl), =NNHSO$_2$(alkyl), or =NR*, where each R* is independently selected from hydrogen or an optionally substituted $C_{1-6}$ aliphatic; wherein an aliphatic group of R* is optionally substituted with $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2$H, $CO_2$($C_{1-4}$ aliphatic), O(halo $C_{1-4}$ aliphatic), or halo($C_{1-4}$ aliphatic), wherein each of the $C_{1-4}$ aliphatic groups of R* is unsubstituted.

In certain embodiments, $R^X$ is selected from

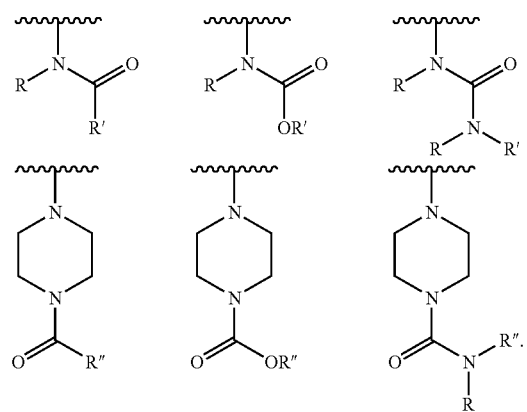

In certain embodiments of the invention, $R^Y$ is

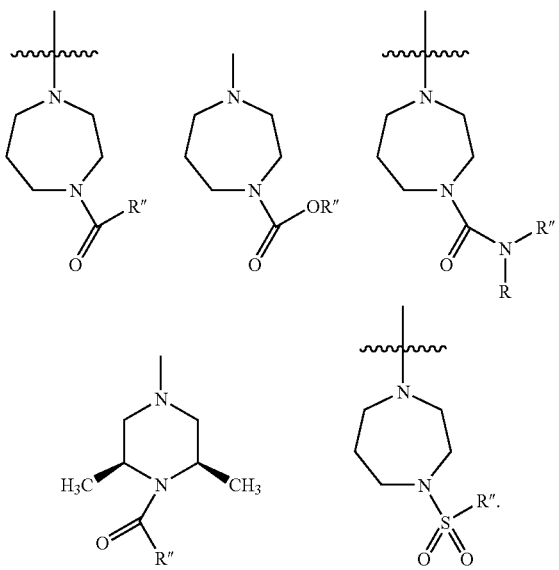

In certain embodiments, A is N.

In other embodiments, A is $CR^2$. In further embodiments, A is CH.

In some embodiments, $R^X$ is selected from

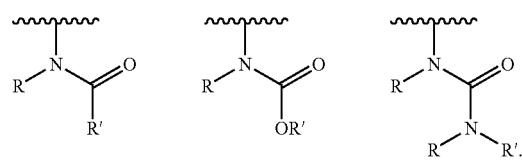

In further embodiments, R' is a $C_{1-6}$ aliphatic, phenyl or a 5-8 membered heteroaryl group, wherein R' is optionally substituted with up to one occurrence of J. In further embodiments, R' is a $C_{1-6}$ aliphatic group or phenyl, wherein R' is optionally substituted with up to one occurrence of J, wherein J is —COOR$^o$, —OR$^o$, R$^o$ or —CF$_3$, and wherein R$^o$ is a $C_{1-3}$ aliphatic group. In still further embodiments, R' is methyl, ethyl, propyl, isopropyl, —CH$_2$-isopropyl, butyl, t-butyl, —CH$_2$-t-butyl or cyclohexyl, wherein R' is optionally substituted with —COOR$^o$, —OR$^o$ or R$^o$. In certain embodiments, R is hydrogen or methyl.

In some embodiments, R$^X$ is selected from

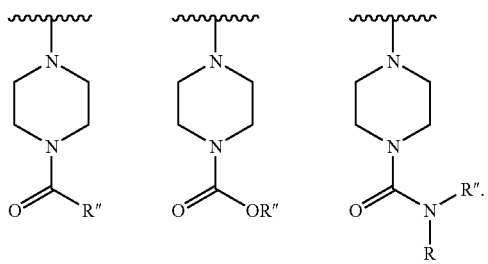

In further embodiments, R" is independently selected from a $C_{1-6}$ aliphatic group, phenyl or a 5-8 membered heterocycle group, wherein R" is optionally substituted with up to one occurrence of J. In further embodiments, R" is independently selected from a $C_{1-6}$ aliphatic group or phenyl, wherein R" is optionally substituted with up to one occurrence of J, wherein J is selected from halogen, —CF$_3$, —CN, —COOR$^o$, —COR$^o$ or —OR$^o$, wherein R$^o$ is a $C_{1-3}$ aliphatic group. In still further embodiments, R" is methyl, ethyl, propyl, isopropyl, —CH$_2$-isopropyl, butyl, t-butyl or —CH$_2$-t-butyl, wherein R" is optionally substituted with —CN, —COOR$^o$ or —OR$^o$. In certain embodiments, R is hydrogen or methyl.

Specific embodiments of R$^X$ are depicted in the compounds in Table 1.

In some embodiments, R$^Y$ is selected from

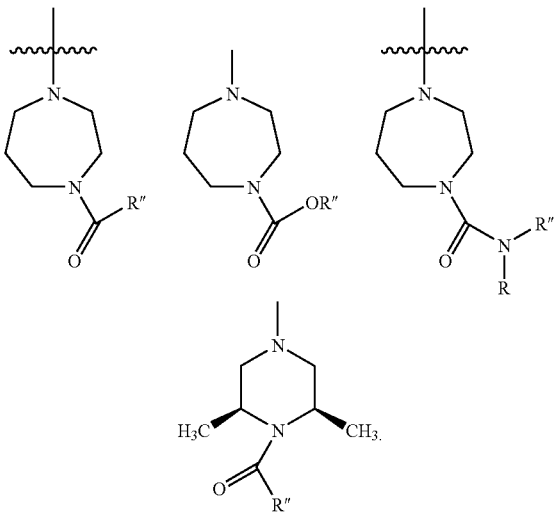

In further embodiments, R" is independently selected from a $C_{1-6}$ aliphatic group, phenyl or a 5-8 membered heterocycle group, wherein R" is optionally substituted with up to one occurrence of J. In further embodiments, R" is independently selected from a $C_{1-6}$ aliphatic group or phenyl, wherein R" is optionally substituted with up to one occurrence of J, wherein J is selected from halogen, —CF$_3$, —CN, —COOR$^o$, —COR$^o$ or —OR$^o$, wherein R$^o$ is a $C_{1-3}$ aliphatic group. In still further embodiments, R" is methyl, ethyl, propyl, isopropyl, —CH$_2$-isopropyl, butyl, t-butyl or —CH$_2$-t-butyl, wherein R" is optionally substituted with —CN, —COOR$^o$ or —OR$^o$. In certain embodiments, R is hydrogen or methyl.

Specific embodiments of R$^Y$ are depicted in the compounds in Table 1.

Representative examples of compounds of formula I are set forth in Table 1.

TABLE 1

Examples of Compounds of Formula I:

| Compound | Cmpd # (I-#) |
|---|---|
|  | 1 |

TABLE 1-continued

Examples of Compounds of Formula I:

| Compound | Cmpd # (I-#) |
|---|---|
| (structure) | 2 |
| (structure) | 3 |
| (structure) | 4 |
| (structure) | 5 |

TABLE 1-continued
Examples of Compounds of Formula I:
| Compound | Cmpd # (I-#) |
|---|---|
| 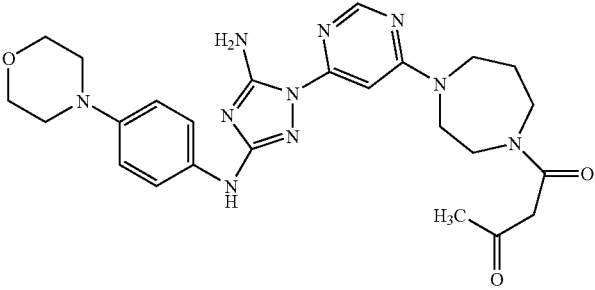 | 6 |
| 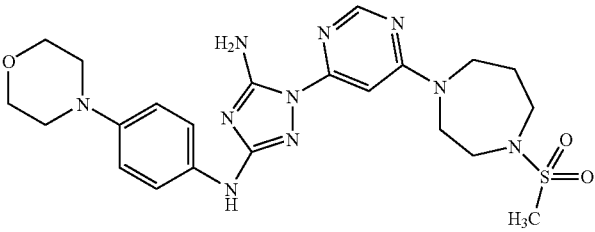 | 7 |
| 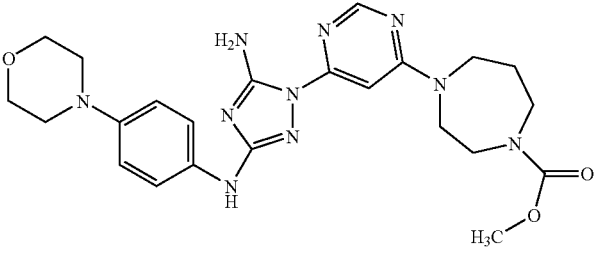 | 8 |
| 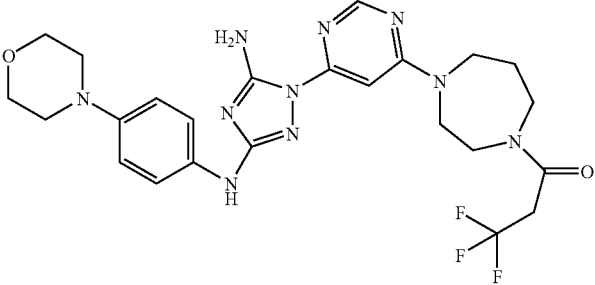 | 9 |
| 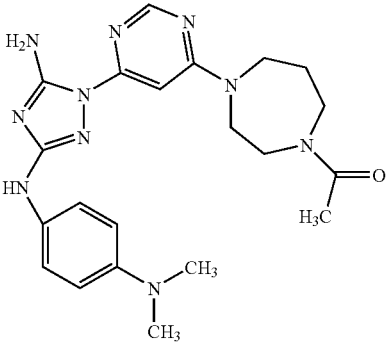 | 10 |

TABLE 1-continued

Examples of Compounds of Formula I:

| Compound | Cmpd # (I-#) |
|---|---|
| | 11 |
| | 12 |
| | 13 |
| | 14 |

TABLE 1-continued
Examples of Compounds of Formula I:
| Compound | Cmpd # (I-#) |
|---|---|
| 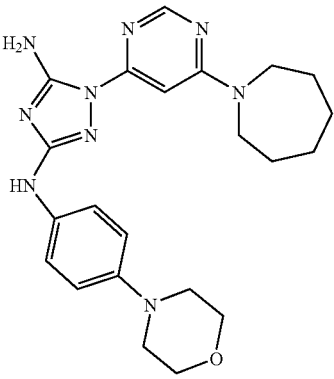 | 15 |
| 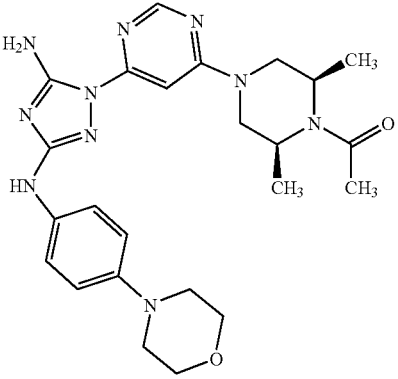 | 16 |
| 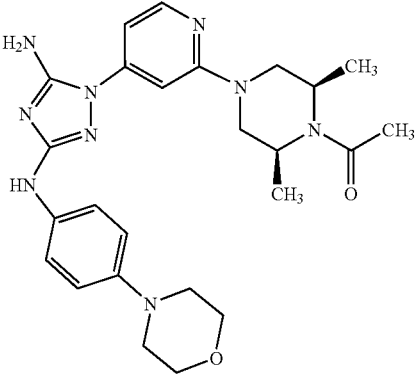 | 17 |

TABLE 1-continued

Examples of Compounds of Formula I:

| Compound | Cmpd # (I-#) |
|---|---|
| (structure) | 18 |
| (structure) | 19 |
| (structure) | 20 |
| (structure) | 21 |

TABLE 1-continued

Examples of Compounds of Formula I:

| Compound | Cmpd # (I-#) |
|---|---|
| | 22 |
| | 23 |
| | 24 |

TABLE 1-continued
Examples of Compounds of Formula I:
| Compound | Cmpd # (I-#) |
|---|---|
| 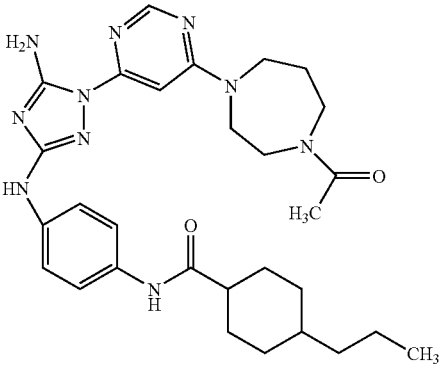 | 25 |
| 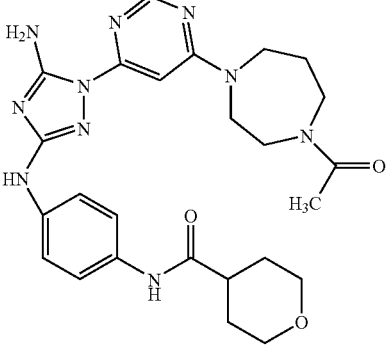 | 26 |
| 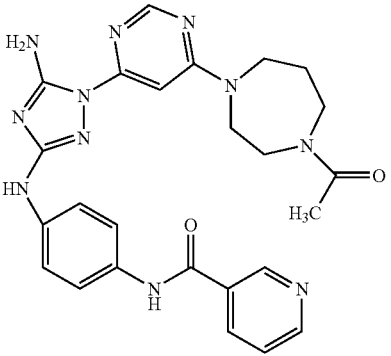 | 27 |
| 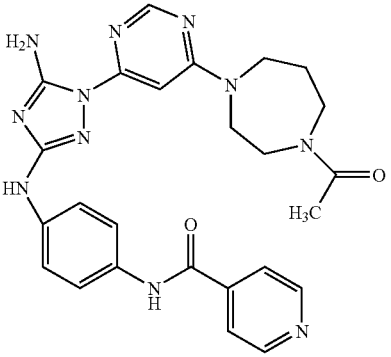 | 28 |

TABLE 1-continued

Examples of Compounds of Formula I:

| Compound | Cmpd # (I-#) |
|---|---|
| (structure) | 29 |
| (structure) | 30 |
| (structure) | 31 |
| (structure) | 32 |

TABLE 1-continued
Examples of Compounds of Formula I:
| Compound | Cmpd # (I-#) |
|---|---|
| 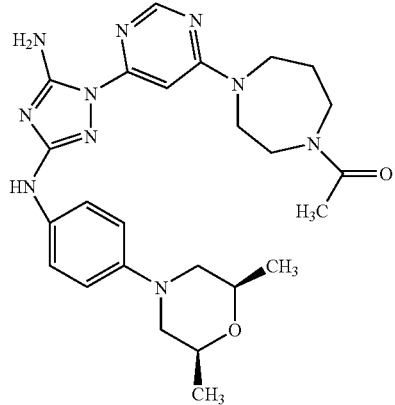 | 33 |
| 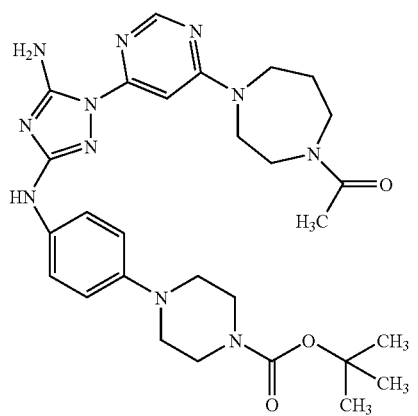 | 34 |
| 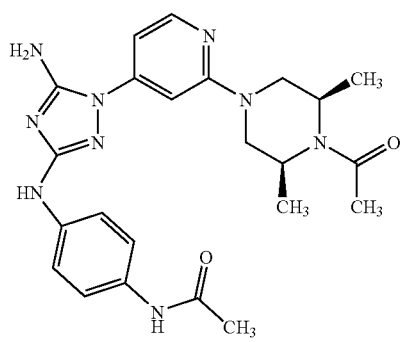 | 35 |

TABLE 1-continued

Examples of Compounds of Formula I:

| Compound | Cmpd # (I-#) |
|---|---|
| (structure) | 36 |
| (structure) | 37 |
| (structure) | 38 |

TABLE 1-continued
Examples of Compounds of Formula I:
| Compound | Cmpd # (I-#) |
|---|---|
| 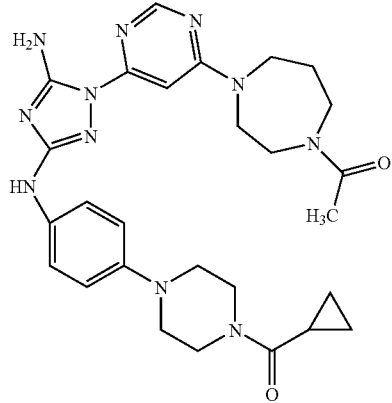 | 39 |
| 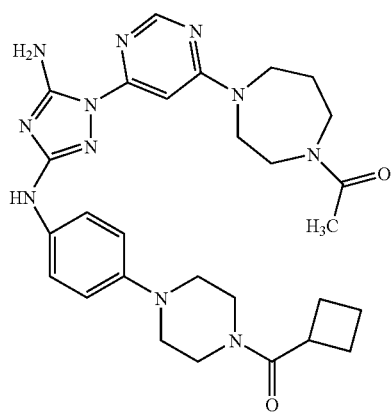 | 40 |
| 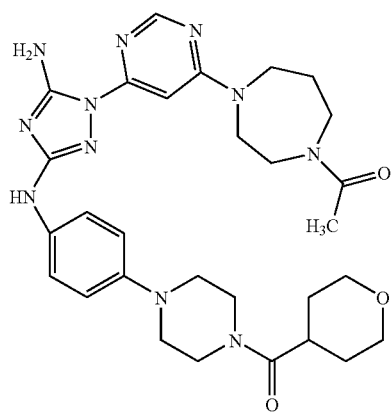 | 41 |

TABLE 1-continued

Examples of Compounds of Formula I:

| Compound | Cmpd # (I-#) |
|---|---|
| [chemical structure] | 42 |
| [chemical structure] | 43 |
| [chemical structure] | 44 |

TABLE 1-continued

Examples of Compounds of Formula I:

| Compound | Cmpd # (I-#) |
|---|---|
|  | 45 |
|  | 46 |
|  | 47 |

TABLE 1-continued

Examples of Compounds of Formula I:

| Compound | Cmpd # (I-#) |
|---|---|
| (structure) | 48 |
| (structure) | 49 |
| (structure) | 50 |

TABLE 1-continued

Examples of Compounds of Formula I:

| Compound | Cmpd # (I-#) |
|---|---|
| *[chemical structure]* | 51 |
| *[chemical structure]* | 52 |
| *[chemical structure]* | 53 |

TABLE 1-continued
Examples of Compounds of Formula I:
| Compound | Cmpd # (I-#) |
|---|---|
| 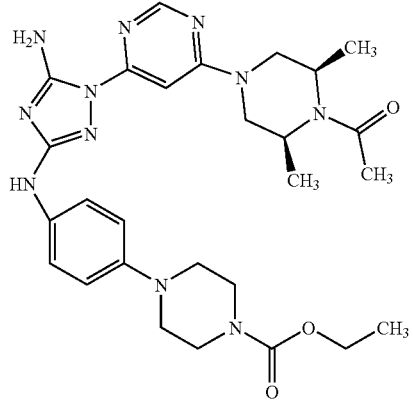 | 54 |
| 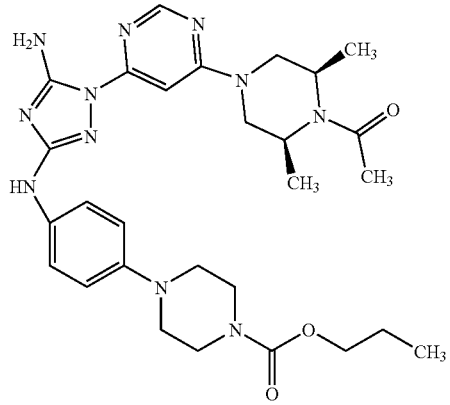 | 55 |
| 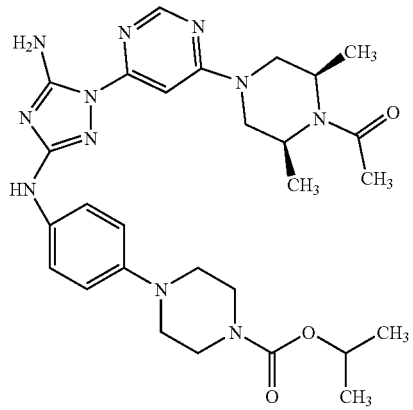 | 56 |

TABLE 1-continued
Examples of Compounds of Formula I:
| Compound | Cmpd # (I-#) |
|---|---|
| 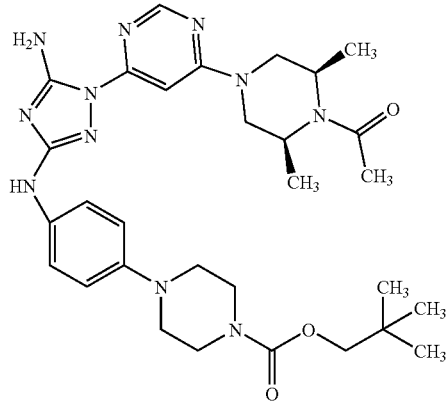 | 57 |
| 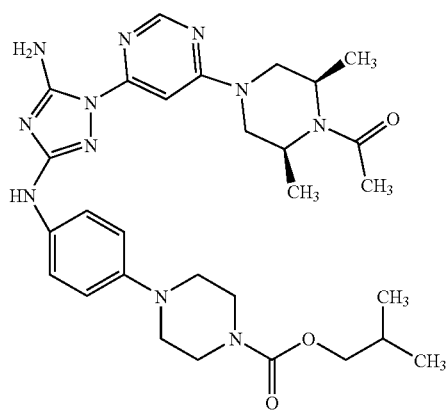 | 58 |
| 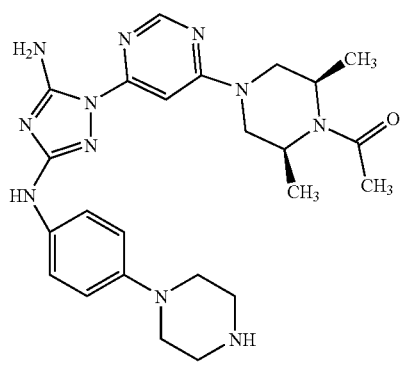 | 59 |

TABLE 1-continued
Examples of Compounds of Formula I:
| Compound | Cmpd # (I-#) |
|---|---|
| 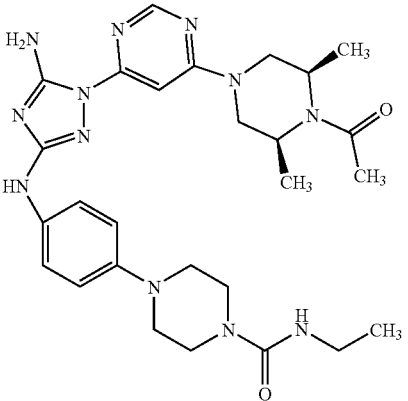 | 60 |
| 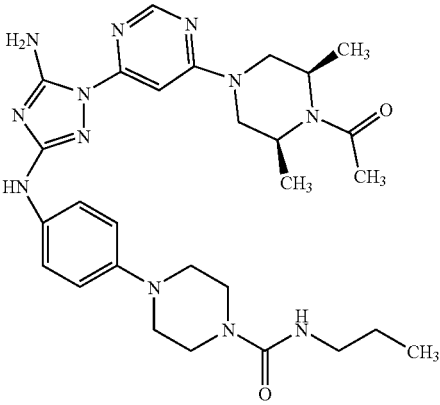 | 61 |
| 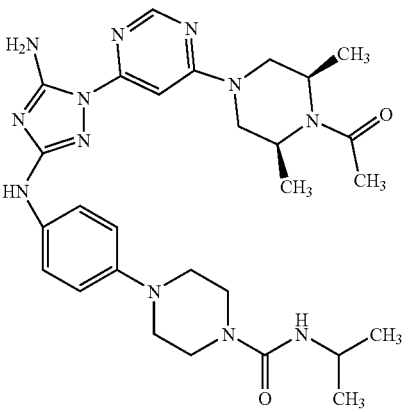 | 62 |

TABLE 1-continued
Examples of Compounds of Formula I:
| Compound | Cmpd # (I-#) |
|---|---|
| 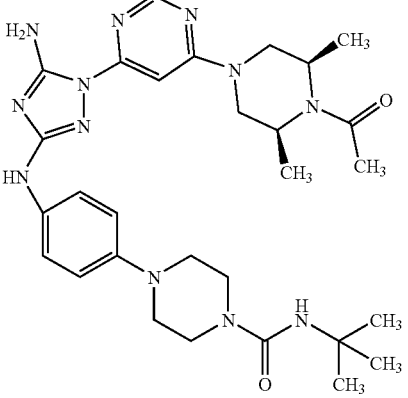 | 63 |
| 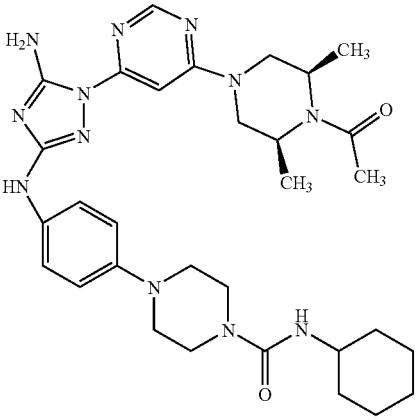 | 64 |
| 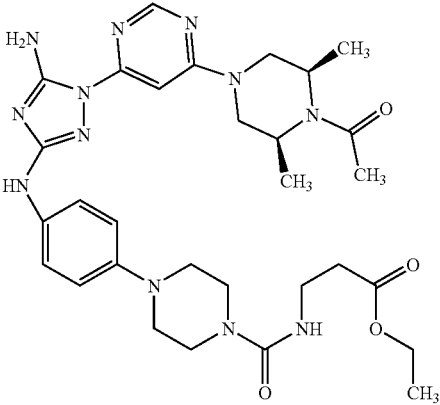 | 65 |

TABLE 1-continued

Examples of Compounds of Formula I:

| Compound | Cmpd # (I-#) |
|---|---|
| (structure) | 66 |
| (structure) | 67 |
| (structure) | 68 |
| (structure) | 69 |

TABLE 1-continued

Examples of Compounds of Formula I:

| Compound | Cmpd # (I-#) |
|---|---|
| (structure) | 70 |
| (structure) | 71 |
| (structure) | 72 |
| (structure) | 73 |

TABLE 1-continued

Examples of Compounds of Formula I:

| Compound | Cmpd # (I-#) |
|---|---|
| (structure) | 74 |
| (structure) | 75 |
| (structure) | 76 |
| (structure) | 77 |

TABLE 1-continued
Examples of Compounds of Formula I:
| Compound | Cmpd # (I-#) |
|---|---|
| 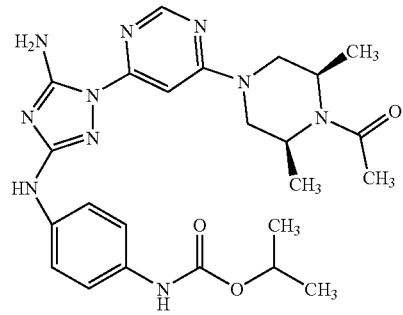 | 78 |
| 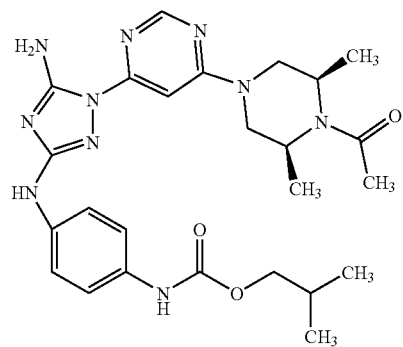 | 79 |
| 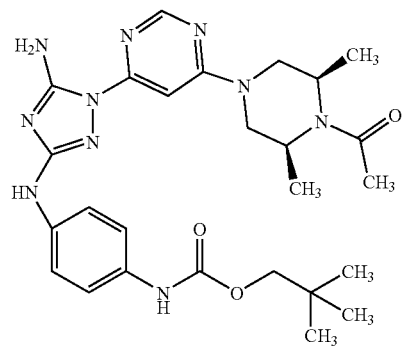 | 80 |
| 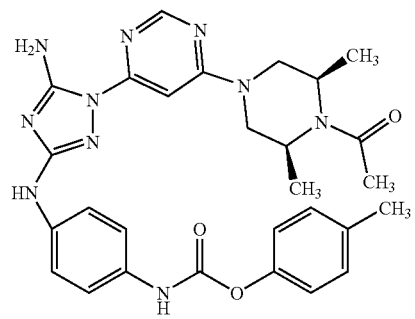 | 81 |

TABLE 1-continued

Examples of Compounds of Formula I:

| Compound | Cmpd # (I-#) |
|---|---|
| (structure) | 82 |
| (structure) | 83 |
| (structure) | 84 |
| (structure) | 85 |

TABLE 1-continued

Examples of Compounds of Formula I:

| Compound | Cmpd # (I-#) |
|---|---|
| (structure) | 86 |
| (structure) | 87 |
| (structure) | 88 |

TABLE 1-continued
Examples of Compounds of Formula I:
| Compound | Cmpd # (I-#) |
|---|---|
| 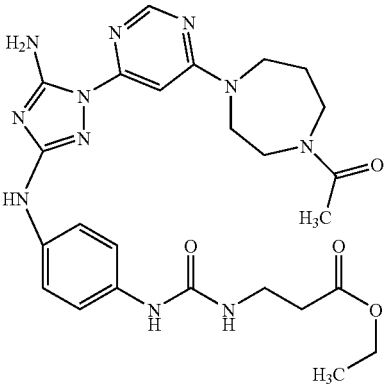 | 89 |
| 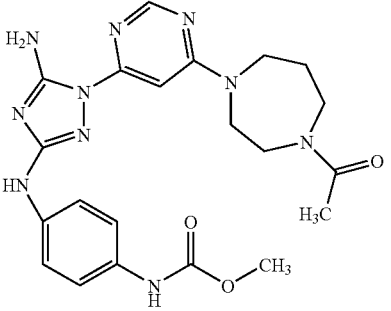 | 90 |
| 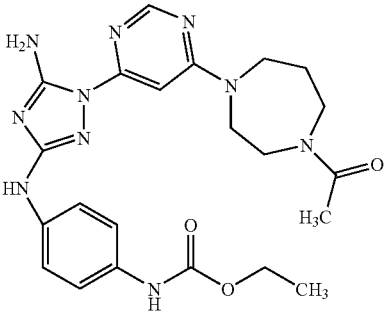 | 91 |
| 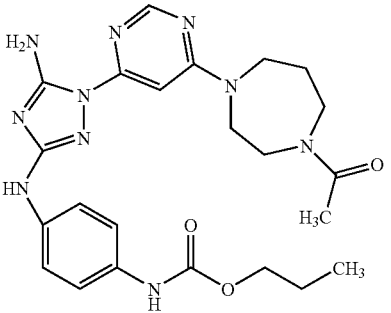 | 92 |

TABLE 1-continued
Examples of Compounds of Formula I:
| Compound | Cmpd # (I-#) |
|---|---|
| 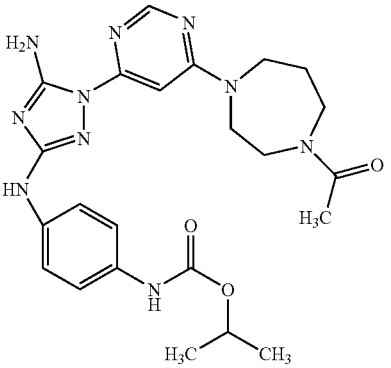 | 93 |
| 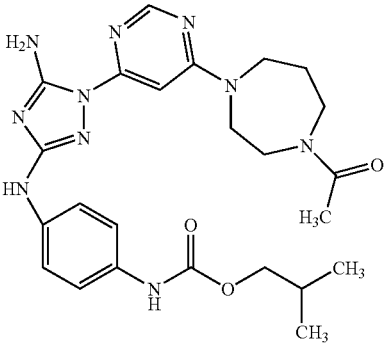 | 94 |
| 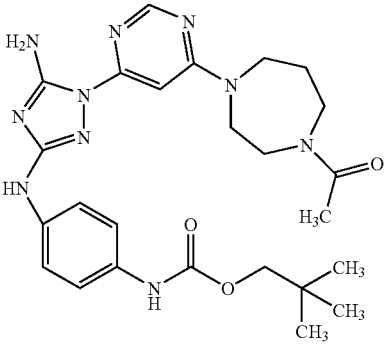 | 95 |

TABLE 1-continued

Examples of Compounds of Formula I:

| Compound | Cmpd # (I-#) |
|---|---|
| | 96 |
| | 97 |
| | 98 |

TABLE 1-continued
Examples of Compounds of Formula I:
| Compound | Cmpd # (I-#) |
|---|---|
| 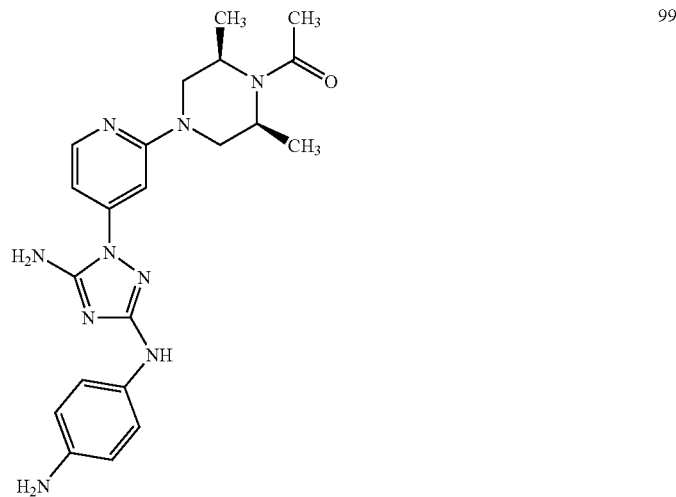 | 99 |
| 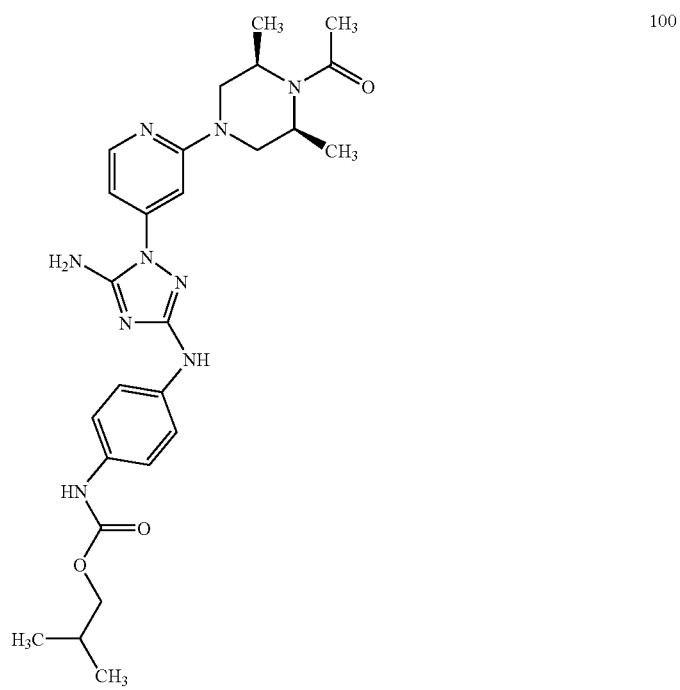 | 100 |

TABLE 1-continued
Examples of Compounds of Formula I:
| Compound | Cmpd # (I-#) |
|---|---|
| 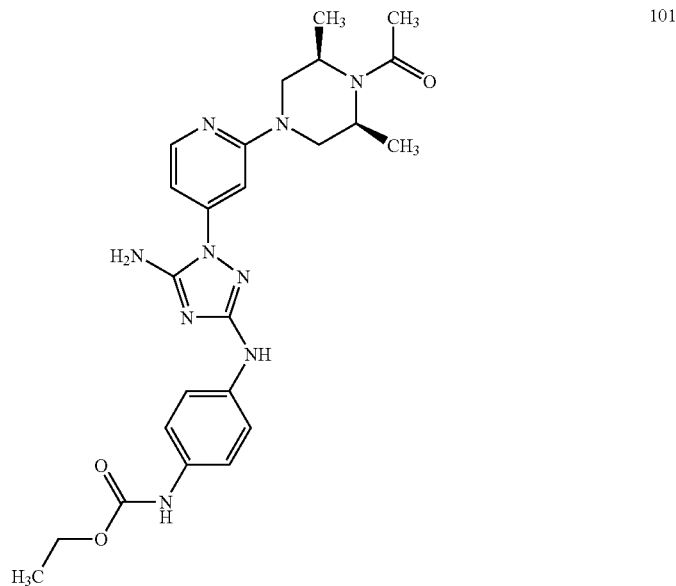 | 101 |
| 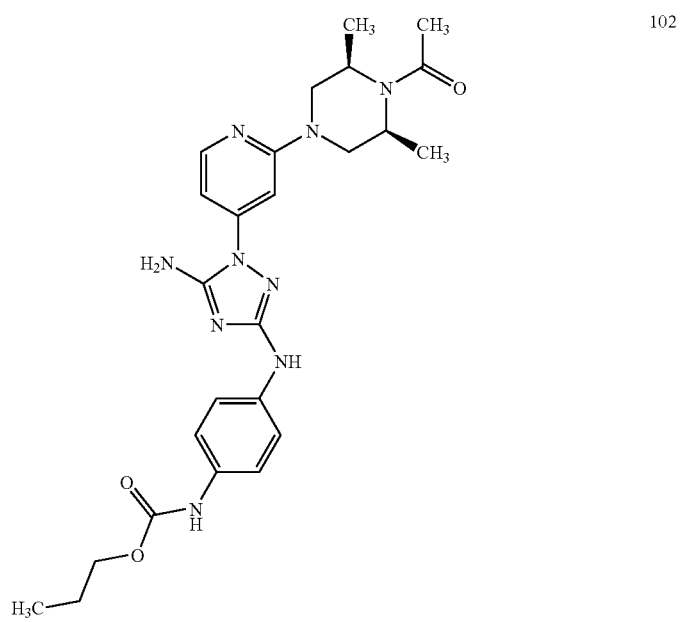 | 102 |

TABLE 1-continued
Examples of Compounds of Formula I:
| Compound | Cmpd # (I-#) |
|---|---|
| 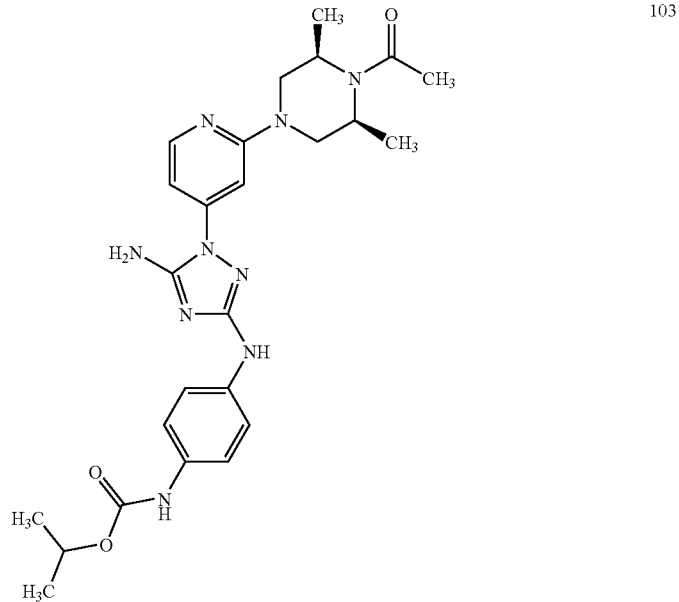 | 103 |
| 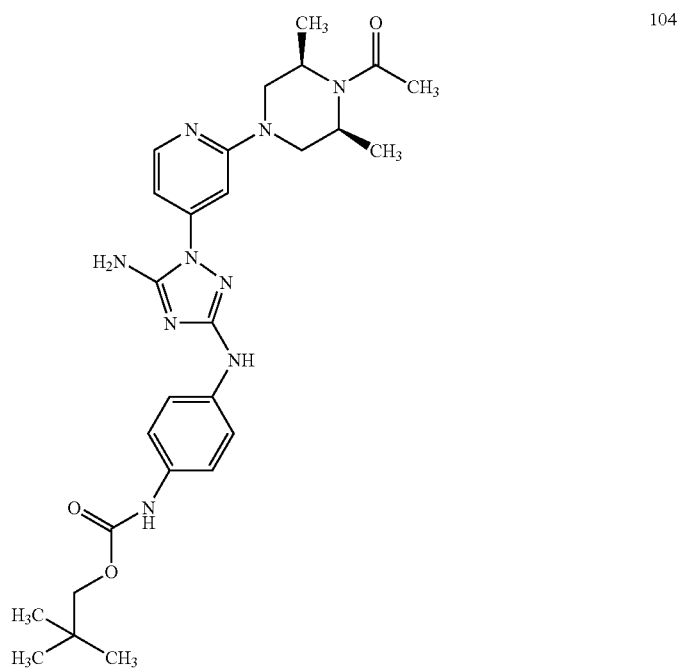 | 104 |

TABLE 1-continued

Examples of Compounds of Formula I:

| Compound | Cmpd # (I-#) |
|---|---|
| (structure) | 105 |
| (structure) | 106 |
| (structure) | 107 |

TABLE 1-continued

Examples of Compounds of Formula I:

| Compound | Cmpd # (I-#) |
|---|---|
| *(structure)* | 108 |
| *(structure)* | 109 |
| *(structure)* | 110 |

TABLE 1-continued
Examples of Compounds of Formula I:
| Compound | Cmpd # (I-#) |
|---|---|
| 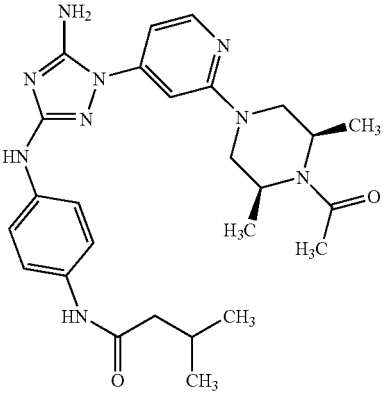 | 111 |
| 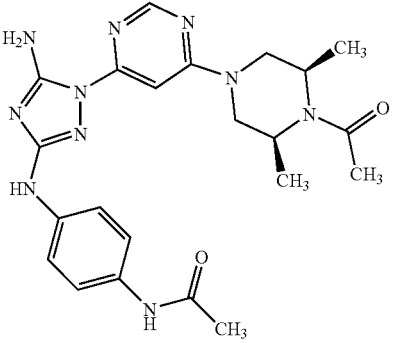 | 112 |
| 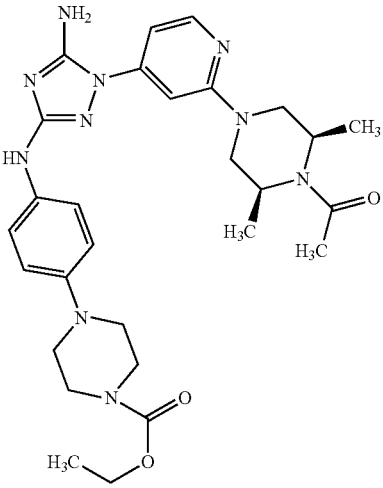 | 113 |

TABLE 1-continued

Examples of Compounds of Formula I:

| Compound | Cmpd # (I-#) |
|---|---|
| | 114 |
| | 115 |
| | 116 |
| | 117 |

TABLE 1-continued
Examples of Compounds of Formula I:
| Compound | Cmpd # (I-#) |
|---|---|
| 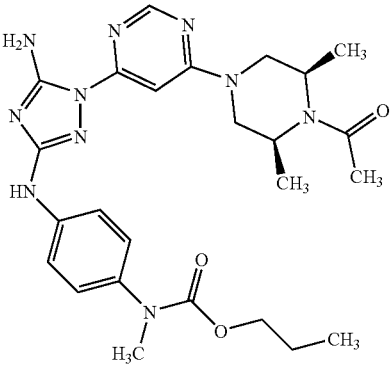 | 118 |
| 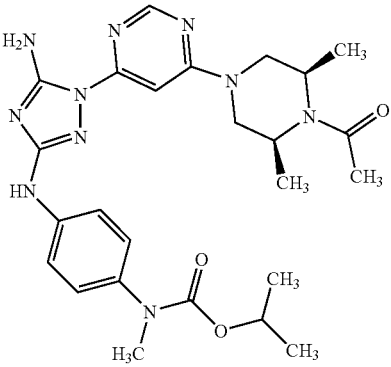 | 119 |
| 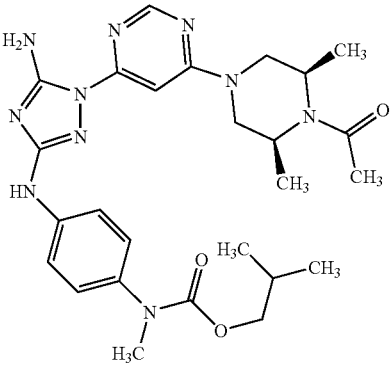 | 120 |
| 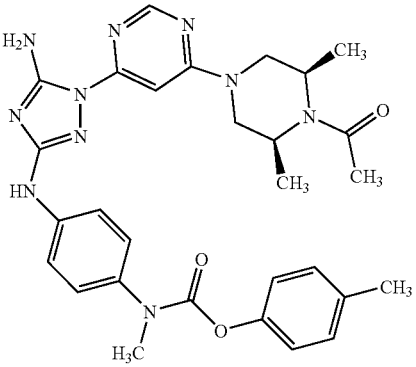 | 121 |

TABLE 1-continued
Examples of Compounds of Formula I:
| Compound | Cmpd # (I-#) |
|---|---|
| 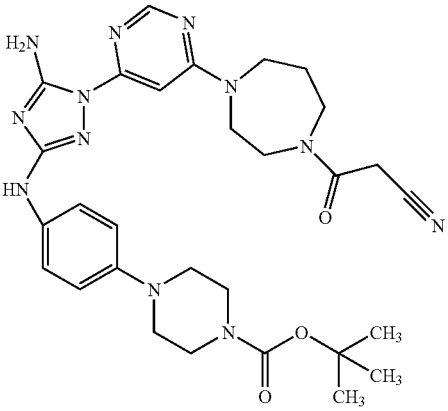 | 122 |
| 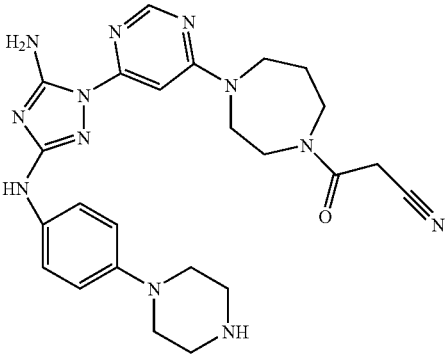 | 123 |
| 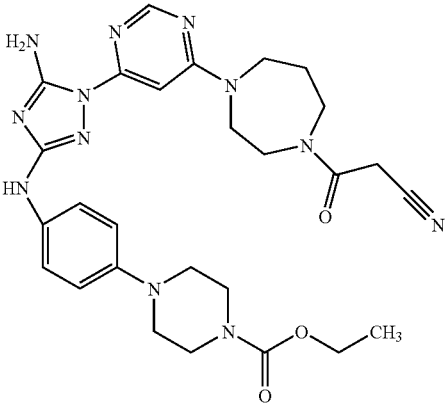 | 124 |

TABLE 1-continued

Examples of Compounds of Formula I:

| Compound | Cmpd # (I-#) |
|---|---|
| [chemical structure] | 125 |
| [chemical structure] | 126 |
| [chemical structure] | 127 |

TABLE 1-continued

Examples of Compounds of Formula I:

| Compound | Cmpd # (I-#) |
|---|---|
| (structure) | 128 |
| (structure) | 129 |
| (structure) | 130 |

TABLE 1-continued

Examples of Compounds of Formula I:

| Compound | Cmpd # (I-#) |
|---|---|
| (structure) | 131 |
| (structure) | 132 |
| (structure) | 133 |

TABLE 1-continued

Examples of Compounds of Formula I:

| Compound | Cmpd # (I-#) |
|---|---|
| (structure) | 134 |
| (structure) | 135 |
| (structure) | 136 |

TABLE 1-continued

Examples of Compounds of Formula I:

| Compound | Cmpd # (I-#) |
|---|---|
| | 137 |
| | 138 |
| | 139 |

TABLE 1-continued
Examples of Compounds of Formula I:
| Compound | Cmpd # (I-#) |
|---|---|
| 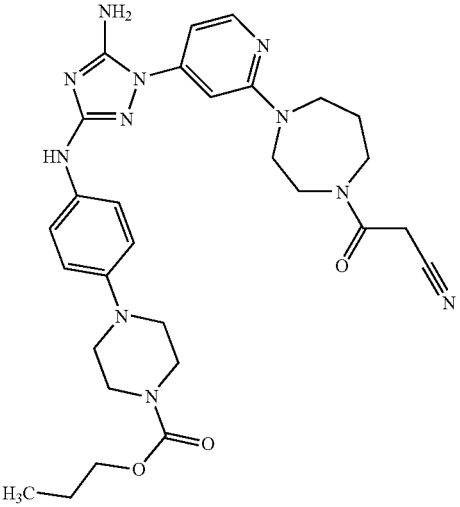 | 140 |
| 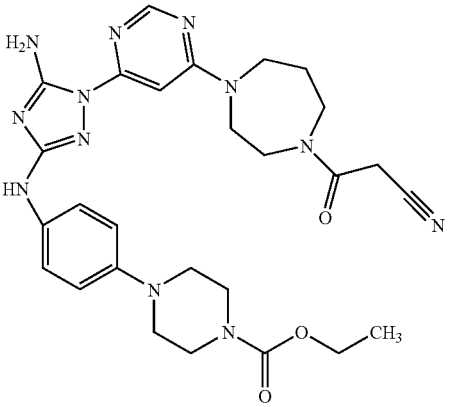 | 141 |
| 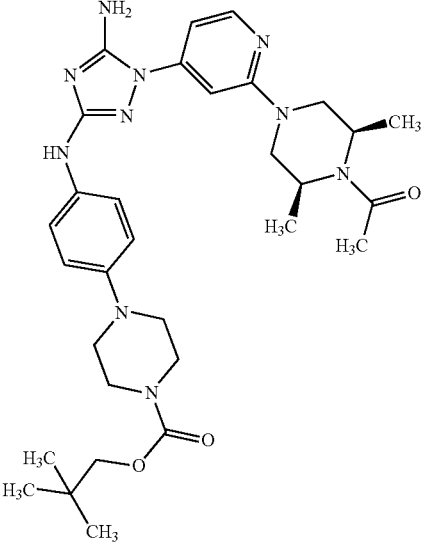 | 142 |

TABLE 1-continued

Examples of Compounds of Formula I:

| Compound | Cmpd # (I-#) |
|---|---|
| *(structure)* | 143 |
| *(structure)* | 144 |
| *(structure)* | 145 |

TABLE 1-continued
Examples of Compounds of Formula I:
| Compound | Cmpd # (I-#) |
|---|---|
| 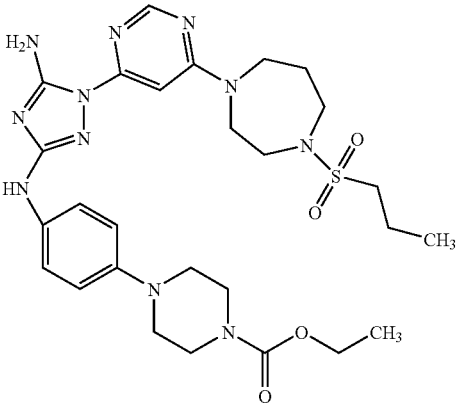 | 146 |
| 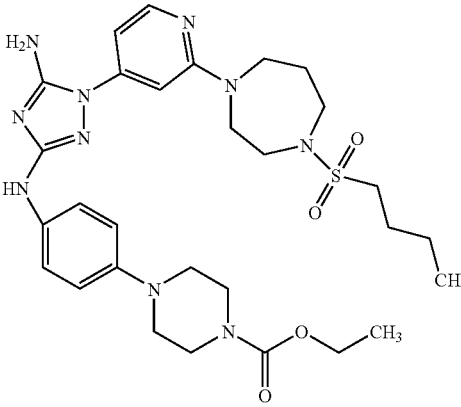 | 147 |
| 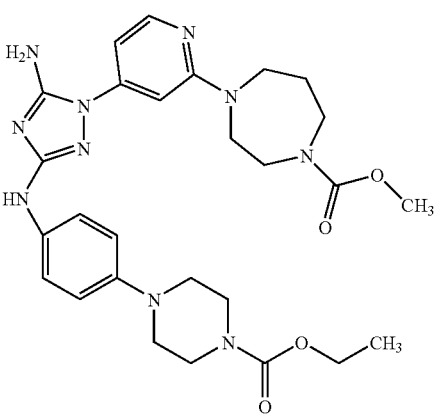 | 148 |

TABLE 1-continued
Examples of Compounds of Formula I:
| Compound | Cmpd # (I-#) |
|---|---|
| 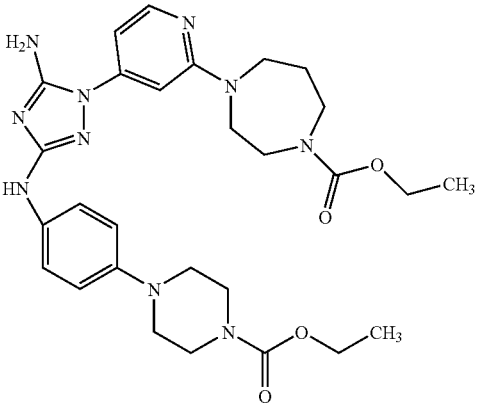 | 149 |
| 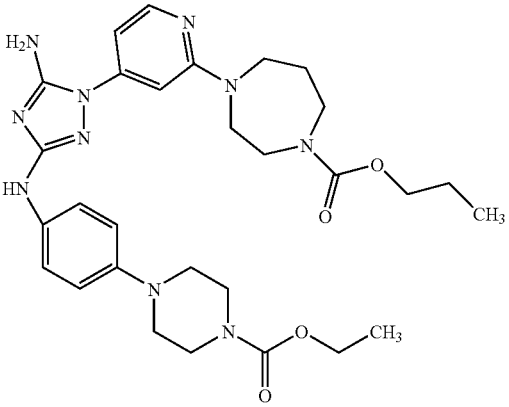 | 150 |
| 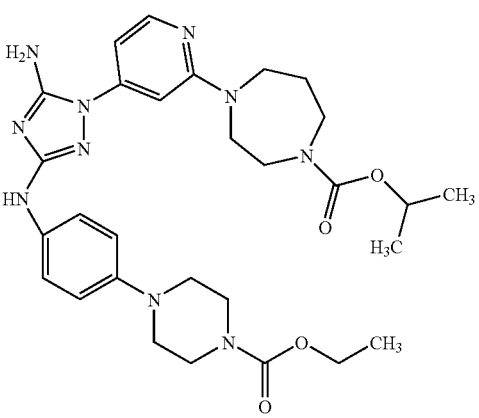 | 151 |

TABLE 1-continued

Examples of Compounds of Formula I:

| Compound | Cmpd # (I-#) |
|---|---|
| (structure) | 152 |
| (structure) | 153 |
| (structure) | 154 |

TABLE 1-continued

Examples of Compounds of Formula I:

| Compound | Cmpd # (I-#) |
|---|---|
| | 155 |
| | 156 |
| | 157 |

TABLE 1-continued
Examples of Compounds of Formula I:
| Compound | Cmpd # (I-#) |
|---|---|
| 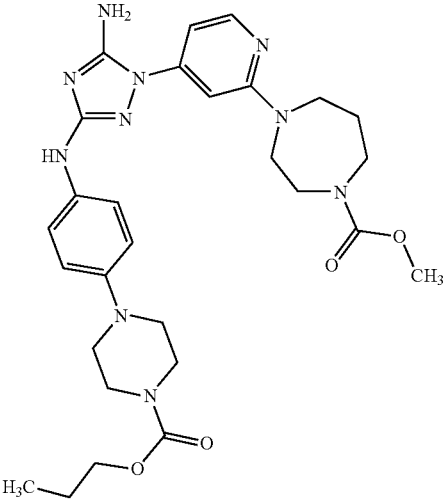 | 158 |
| 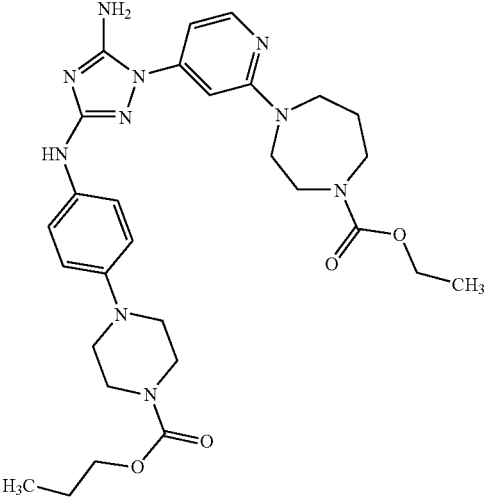 | 159 |
| 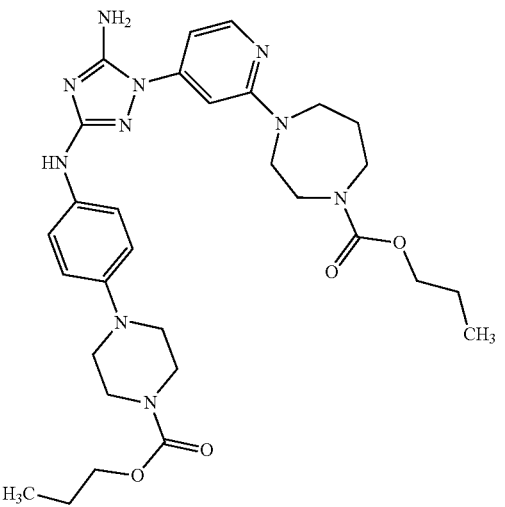 | 160 |

TABLE 1-continued

Examples of Compounds of Formula I:

| Compound | Cmpd # (I-#) |
|---|---|
| (structure) | 161 |
| (structure) | 162 |
| (structure) | 163 |

TABLE 1-continued
Examples of Compounds of Formula I:
| Compound | Cmpd # (I-#) |
|---|---|
| 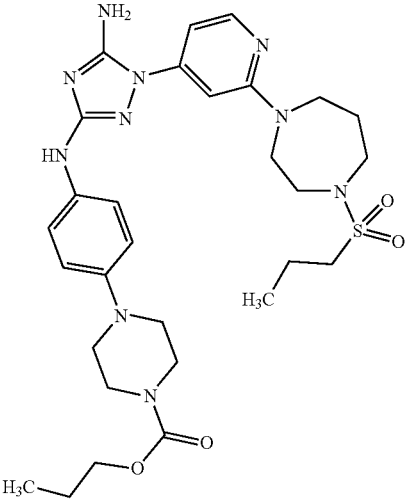 | 164 |
| 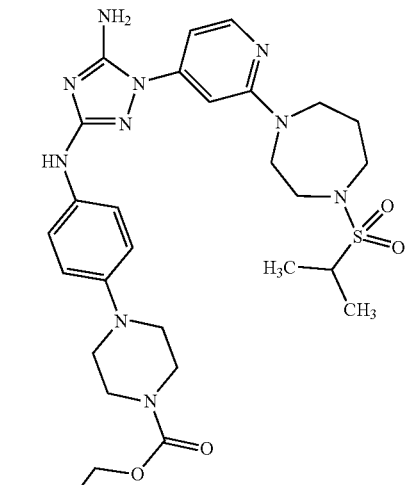 | 165 |
| 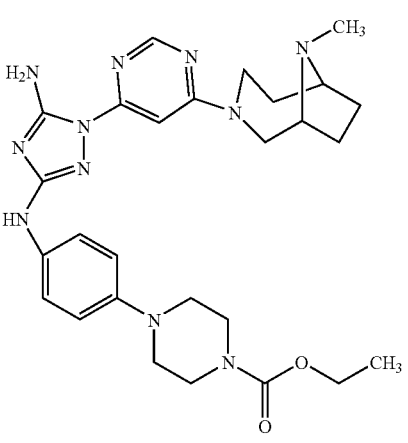 | 166 |

TABLE 1-continued

Examples of Compounds of Formula I:

| Compound | Cmpd # (I-#) |
|---|---|
| (structure) | 167 |
| (structure) | 168 |
| (structure) | 169 |

TABLE 1-continued
Examples of Compounds of Formula I:
| Compound | Cmpd # (I-#) |
|---|---|
| 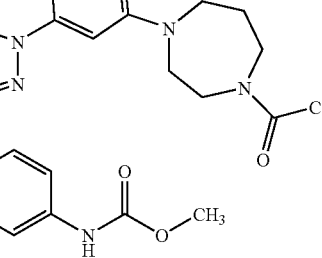 | 170 |
| 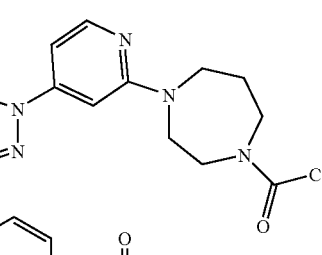 | 171 |
| 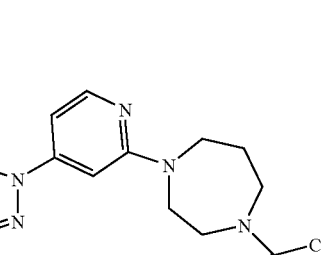 | 172 |
| 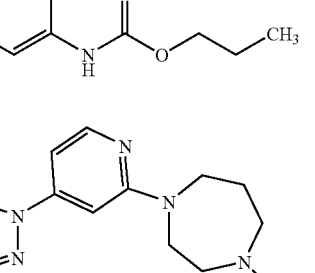 | 173 |

TABLE 1-continued

Examples of Compounds of Formula I:

| Compound | Cmpd # (I-#) |
|---|---|
| 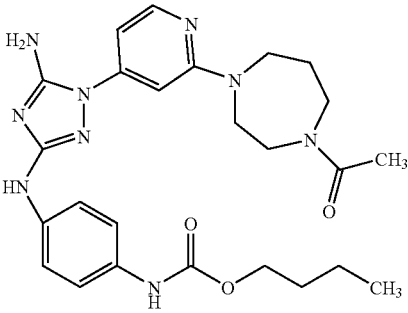 | 174 |
| 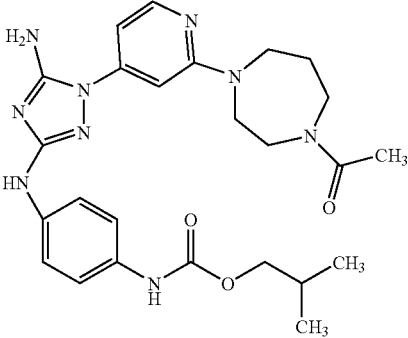 | 175 |
| 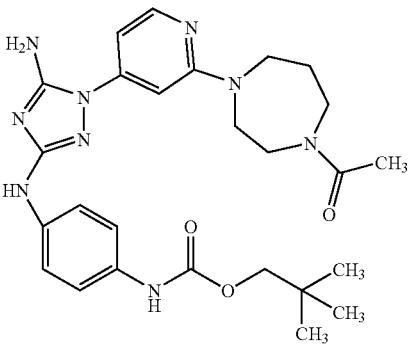 | 176 |

General Synthetic Methodology:

The compounds of this invention may be prepared in general by methods known to those skilled in the art for analogous compounds, by methods as illustrated by the general schemes below, and by the preparative examples that follow. The processes for preparing the compounds of this invention are as described in the schemes and examples. In the schemes, the variables are as defined in the compounds (e.g., formula I) herein or are readily recognized by referring to those compounds.

Scheme 7 depicts the synthesis of certain exemplary compounds where $Ar^1$ and $Ar^2$ is substituted.

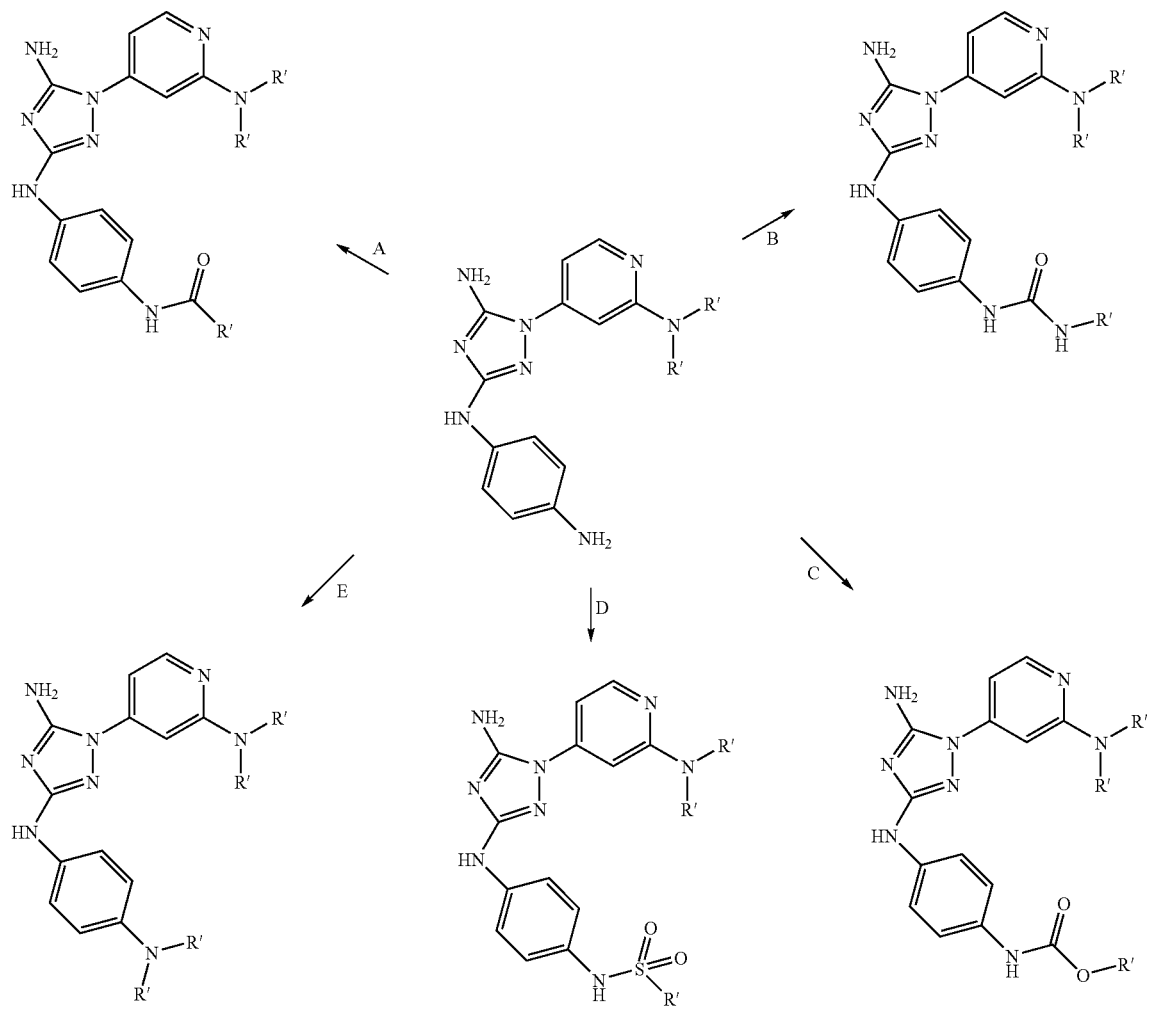

General conditions: solvent, base, appropriate coupling agent, e.g.: A. DMF, DIEA, RCOCl; B. DMF, IEA, isocyanate; C. DMF, DIEA, chloroformate D. DMF, DIEA, lSO2R; E. iProH, alkyl halide, heat.

Scheme 7 depicts a route to compounds of this invention wherein an $Ar^1$ is substituted with an amine derivative, specifically where $R^2$ is $(T)_nAr^1$, and $Ar^1$ is substituted with an amine derivative. In Scheme 7, the amine group is reacted under standard coupling conditions to provide an amine derivative. It should be understood that the depicted synthesis could be modified to also provide other amine derivatives. Furthermore, coupling conditions other than those depicted could be used. Such methods are well-known to skilled practitioners (see, e.g., Greene or Greene & Wutz, Protective Groups in Organic Synthesis; WO 01/81330). It should be understood that the conditions should typically be chosen to be compatible with (i.e., unreactive to) the remaining substituents (e.g., the —$NR^1R^2$).

Scheme 1:
Route to diamino triazole compounds

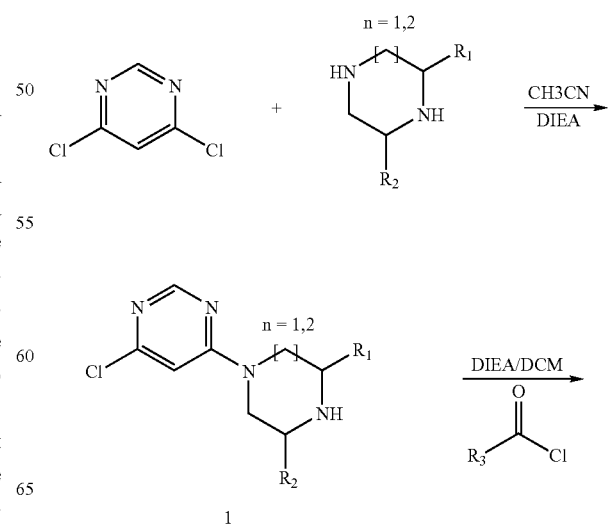

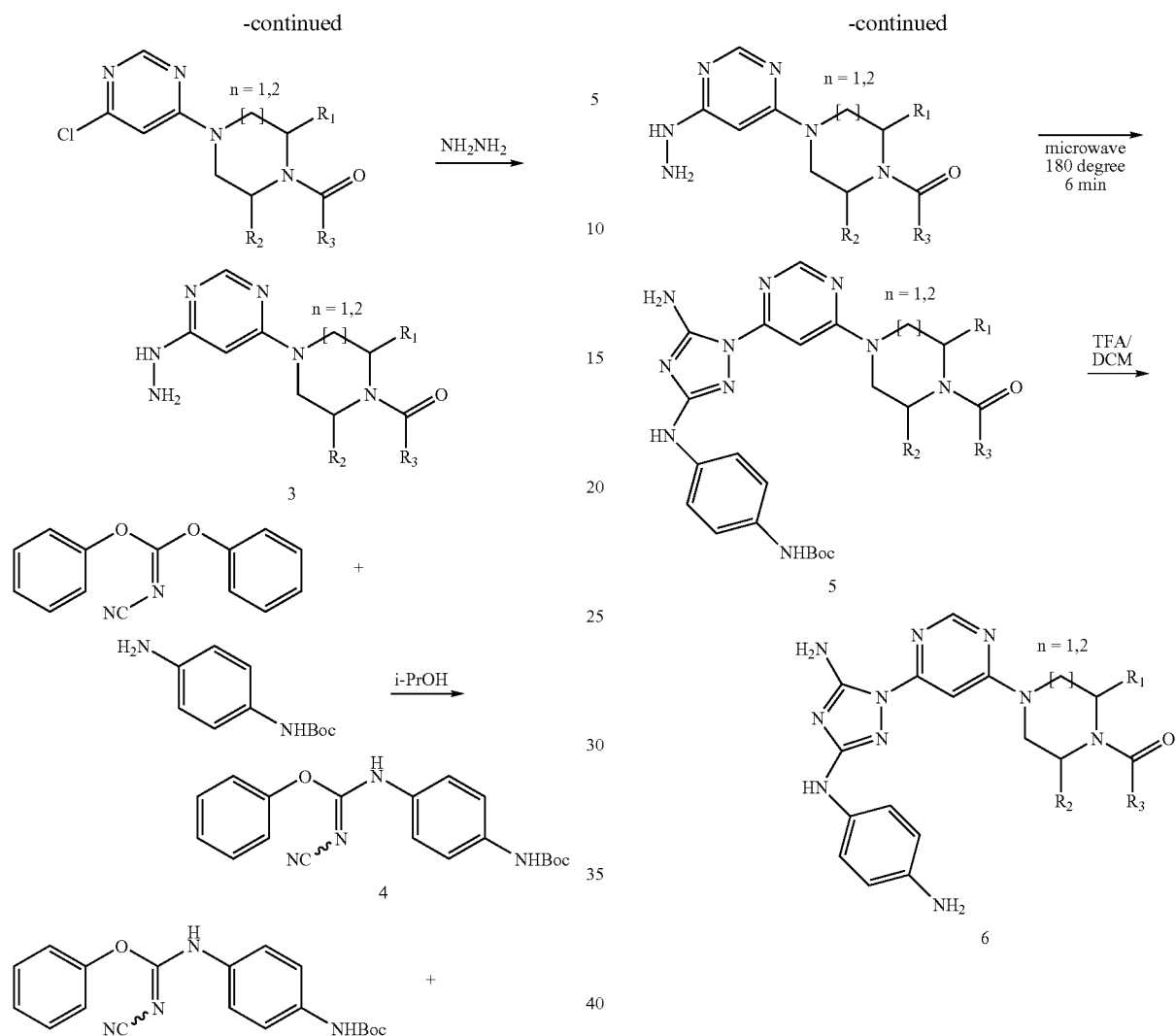
Scheme 2:
Route to derivatives diamino triazole compounds
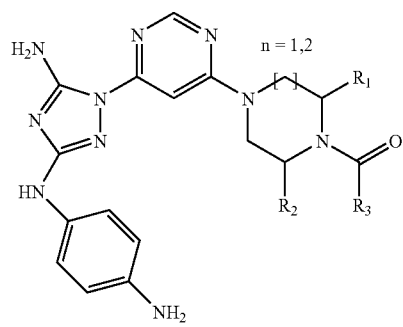
Method A          Method C          Method B

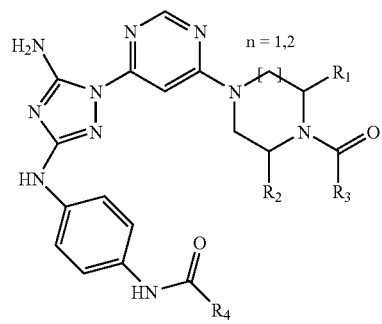
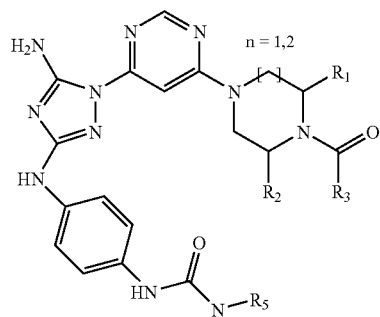
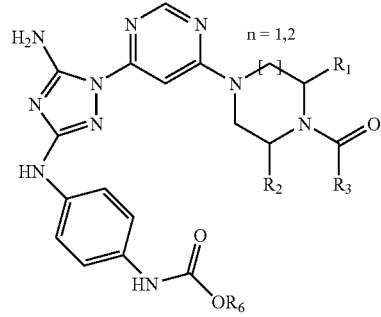
Method A: DMF, DIEA, R.T., carboxylate chloride
Method B: DMF, DIEA, R.T., isocynate
Method C: DMF, DIEA, R.T., chloroformate
Scheme 3:
Route to diamino triazole compounds
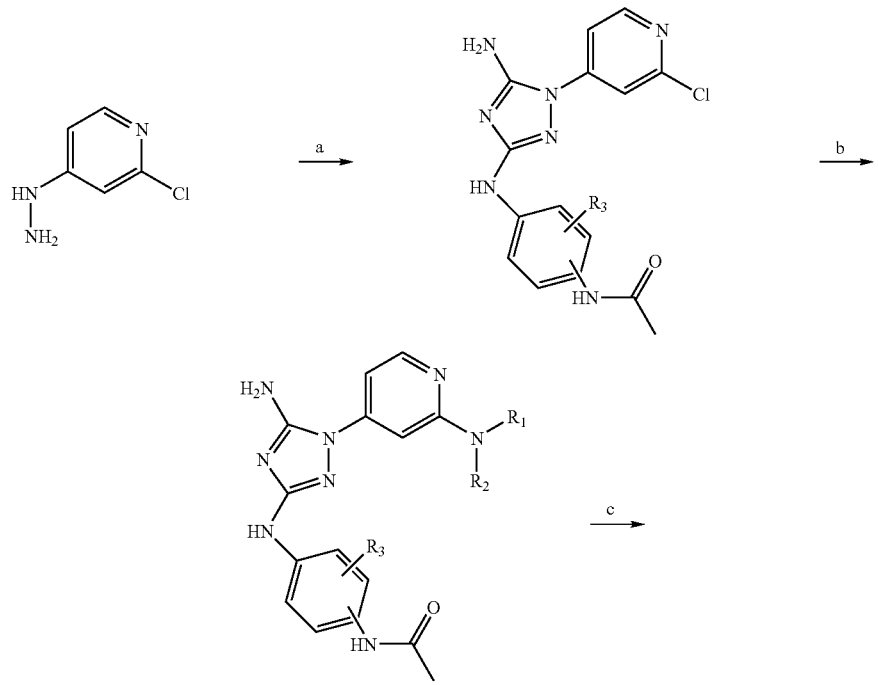

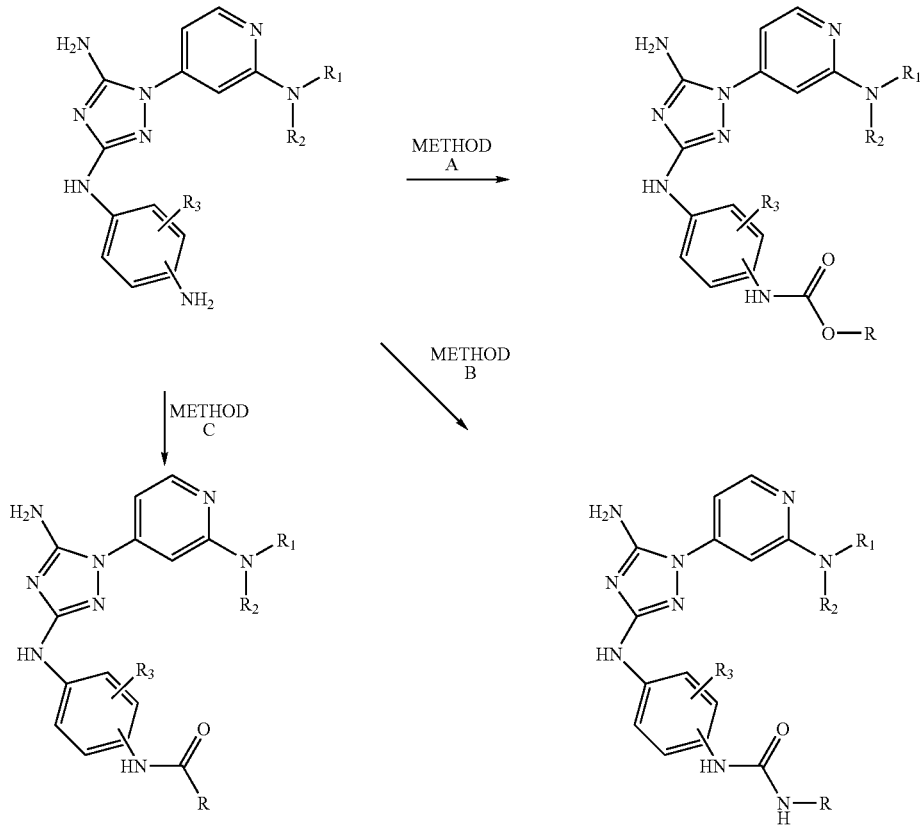

(a) N-cyano-N'-aryl-O-phenylisourea, NMP, DIEA, MW, 160-220° C., 6-15 min; (b) HNR₁R₂, NMP, MW, 220-250° C., 6-15 min; (c) 6N HCl, 95° C.; METHOD A: ClCO₂R (chloroformate), DIEA, DMF; METHOD B: OCN—R (isocyanate), DIEA, DMF; METHOD C: RCO₂H (carboxylic acid), DCC, DCM, or RCOCl (acid chloride), DIEA or pyridine, DMF Another general route to compounds of this invention is depicted in Scheme 3. Although specific reagents are depicted in Scheme 3, skilled practitioners would realize that other steps and reagents could be used to carry out the depicted synthesis. Schemes 4 and 5 below depict this general scheme more specifically.

Although certain exemplary embodiments are depicted and described above and herein, it will be appreciated that the compounds of the invention can be prepared according to the methods described generally above using appropriate starting materials by methods generally available to one of ordinary skill in the art.

Uses, Formulations and Administration

Pharmaceutically Acceptable Compositions

As discussed above, the present invention provides compounds that are inhibitors of protein kinases, and thus the present compounds are useful for the treatment of diseases, disorders, and conditions including, but not limited to, allergic disorders, proliferative disorders, autoimmune disorders, conditions associated with organ transplant, inflammatory disorders, immunologically mediated disorders, viral diseases, or destructive bone disorders (such as bone resorption disorders). Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or a metabolite or residue thereof that inhibits the kinase of interest, including Aurora-2, Flt3, KDR, JAK2 and JAK3. In particular embodiments, the compound or pharmaceutically acceptable salt thereof inhibits JAK2 or JAK3.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts.

This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of allergic disorders, proliferative disorders, autoimmune disorders, conditions associated with organ transplant, inflammatory disorders, immunologically mediated disorders, viral diseases, or destructive bone disorders(such as bone resorption disorders) is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of the disease, disorder, or condition of interest. The compounds and compositions, according to the method of the present invention, may be administered using any amount and any route of administration effective for treating or lessening the severity of the disease, disorder, or condition of interest. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of Aurora-2, Flt3, KDR, JAK2 and JAK3. In certain preferred embodiments, these compounds are effective as inhibitors of JAK2 and JAK3. Thus, without wishing to be bound by any particular theory, the compounds and compositions are particularly useful for treating or lessening the severity of a disease, condition, or disorder where activation of one or more of the protein kinases, including Aurora-2, Flt3, KDR, JAK2 and JAK3 kinases, is implicated in the disease, condition, or disorder. When activation of the Aurora-2, Flt3, KDR, JAK2 and JAK3 kinases is implicated in a particular disease, condition, or disorder, the disease, condition, or disorder may also be referred to as "Aurora-2, Flt3, KDR, JAK2 or JAK3-mediated disease" or disease symptom. Accordingly, in another aspect, the present invention provides a method for treating or lessening the severity of a disease, condition, or disorder where activation or one or more protein kinase, including the Aurora-2, Flt3, KDR, JAK2 and JAK3 kinases is implicated in the disease state.

The activity of a compound utilized in this invention as an inhibitor of a protein kinase, may be assayed in vitro, in vivo or in a cell line. In vitro assays include assays that determine inhibition of either the phosphorylation activity or ATPase activity of, e.g., activated Aurora-2, Flt3, KDR, JAK2 and JAK3. Alternate in vitro assays quantitate the ability of the inhibitor to bind to the protein kinase. Inhibitor binding may be measured by radiolabelling the inhibitor prior to binding, isolating the inhibitor/enzyme, complex and determining the amount of radiolabel bound. Alternatively, inhibitor binding may be determined by running a competition experiment where new inhibitors are incubated with, e.g., Aurora-2, Flt3, KDR, JAK2 and JAK3 bound to known radioligands.

The term "measurably inhibit", as used herein means a measurable change in a kinase activity activity between a sample comprising a composition and a kinase and an equivalent sample comprising the kinase in the absence of the composition.

The term "FLT-3-mediated disease", as used herein means any disease or other deleterious condition in which a FLT-3 family kinase is known to play a role. Such conditions include, without limitation, hematopoietic disorders, in particular, acute-myelogenous leukemia (AML), acute-promyelocytic leukemia (APL), and acute lymphocytic leukemia (ALL).

The term "JAK-mediated disease", as used herein means any disease or other deleterious condition in which a JAK family kinase, in particular JAK-3, is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas. Conditions in which JAK2 play a role include myeloproliferative disorders, such as polycythemia vera, essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

The term "AUR-mediated disease" or "AUR-mediated condition", as used herein, means any disease or other deleterious condition in which AUR protein kinase is known to play a role. Such conditions include, without limitation, allergic disorders, especially asthma.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to auenuatc any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adrianiycin, dexamethasone, and cyclophosphamide. For a more comprehensive discussion of updated cancer therapies see the NCI/NIH web site, a list of the FDA approved oncology drugs at FDA web site, and the Merck Manual, Seventeenth Ed. 1999, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting a protein kinase (e.g., Aurora02, activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of kinase activity, including Aurora-2, Flt3, KDR, JAK2 and JAK3 kinase activity, in a biological sample is useful for a variety of purposes that are known to one of skill in the art. Examples of such purposes include, but are not limited to, blood transfusion, organ-transplantation, biological specimen storage, and biological assays.

EXAMPLES

Compounds of general formula I were prepared according to the general procedures described in the Schemes and Examples herein.

Example 1

Preparation of 4-chloro-6-((3S,5R)-3,5-dimethylpiperazin-1-yl)pyrimidine (1)

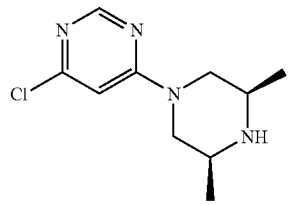

1

To a solution of 4,6-dichloropyrymidine (14.9 g, 100.0 mmol) in 150 ml anhydrous acetonitrile was added (2S,6R)-2,6-dimethylpiperazine (22.8 g, 200.0 mmol) portionwise over 10 min. The reaction was kept at room temperature using a water-bath and stirred for another 20 minutes. Solid precipitated out from solution during the course of reaction. Solid was removed by filtration. The filtrate was concentrated to an oily material. This material was dissolved in EtOAc (300 ml) and organic layer was washed with water (100 ml×3). Organic layer was dried over $Na_cSO_4$. Removal of solvent left an oil product as desired product confirmed by LC/MS (MS+1=227.1). This material was weighted at 22.1 g (yield 97.6%).

Example 2

Preparation of 1-((2S,6R)-4-(6-chloropyrimidin-4-yl)-2,6-dimethylpiperazin-1-yl)ethanone (2)

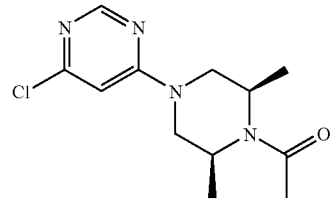

2

To a solution of 4-chloro-6-((3S,5R)-3,5-dimethylpiperazin-1-yl)pyrimidine(1, 10.29 g, 45.4 mmol) and DIEA (8.80 g, 68.1 mmol. 1.50 equiv.) in 100 ml DCM was added acetyl chloride (4.03 ml, 56.7 mmol, 1.25 equiv.) at room temperature portionwise over 10 min. The reaction was stirred at room temperature for another 30 min. Aqueous NaHCO3 was added to the reaction and the organic layer was washed with NahCO3 (100 ml×2) followed by saturated aqueous NaCl solution. The organic layer was dried over Organic layer was dried over $Na_cSO_4$. Removal of solvent left a yellow oil. This oily material was triturated in diethyl ether to afford a white solid. The solid was collected by filtration and the washed with diethyl ether again. The solid was dried under vacuum and was weighted at 11.95 g. The yield is 98.2%. LC/MS (M+1=269.1).

Example 3

Preparation of 3

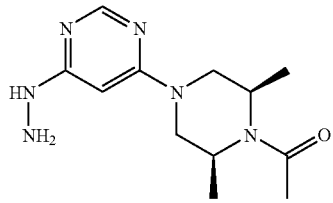

3

To a solution of 1-((2S,6R)-4-(6-chloropyrimidin-4-yl)-2,6-dimethylpiperazin-1-yl)ethanone (2, 9.61 g, 35.7 mmol) in 75 ml anhydrous THF was added hydrazine (5.72 g, 5.60 ml, 178.8 mmol, 5.0 equiv.). Solid was precipitated out of the solution during the course of reaction. The reaction was stirred and refluxed overnight. The reaction was cooled to room temperature. The solid was collected filtration and was washed by cold methanol (25 ml×3) to get rid of excess hydrazine and its HCl salt. The solid was dried under vacuum and was weighted at 8.95 g (83.3% yield). LC/MS (M+1=265.2).

Example 4

Preparation of tert-butyl 4-((Z)-1-cyano-2-phenylisoureido)phenylcarbamate (4)

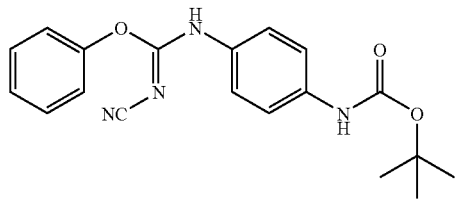

4

To a suspension of diphenyl cyanocarbonimidate (11.04 g, 46.4 mmol) in 130 ml isopropanol was added tert-butyl 4-aminophenylcarbamate (9.20 g, 44.2 mmol). The reaction was stirred at room temperature overnight and the solid was collected by filtration. Solid was dried under vacuum and it was weighted at 10.85 g (69.7% yield). LC/MS (M+1=353.2).

Example 5

Preparation of 5

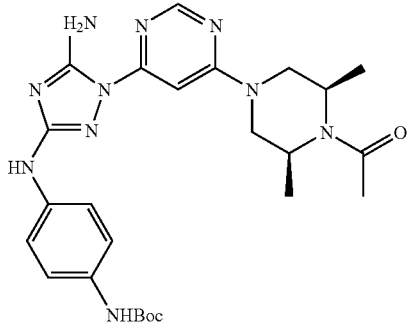

5

To a solution of 3 (3.17 g, 12.0 mmol) and tert-butyl 4-((Z)-1-cyano-2-phenylisoureido)phenylcarbamate (4, 3.52 g, 10.0 mmol) in 6 ml NMP was added 1 ml DIEA. The reaction was sealed in a microwave reaction tube and heated in a microwave reactor at 180 degree over 6 min. The reaction was cooled to room temperature and partitioned between ethyl acetate and water. The organic layer was washed with water twice and was dried over Na2SO4. Removal of solvent left yellow solid. This solid was washed by DCM to afford a white solid. NMR: DMSO-d6: 8.98 (bs, 1H); 8.94 (s, 1H); 8.38 (s, 1H); 7.72 (bs, 2H); 7.45 (d, 2H); 7.25 (d, 2H); 6.73 (s, 1H); 4.60-4.10 (m, 4H); 3.20 (m, 2H); 2.02 (s, 3H); 1.40 (s, 9H); 1.15 (m, 6H). LC/MS (M+1=523.3).

Example 6

Preparation of 1-((2S,6R)-4-(6-(3-(4-aminophenylamino)-5-amino-1H-1,2,4-triazol-1-yl)pyrimidin-4-yl)-2,6-dimethylpiperazin-1-yl)ethanone (6)

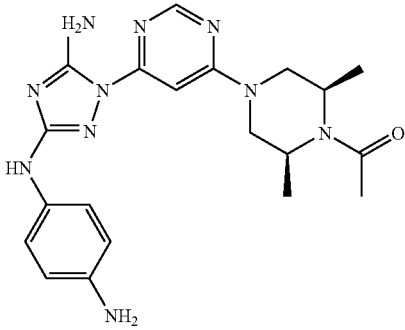

6

To a solution of 6 (2.0 g, 3.83 mmol) in 15 ml DCM was added 5 ml TFA. The reaction was stirred at room temperature over 30 min. HPLC showed the completion of the reaction. The solvent was removed in vacuum and the resulting oily material was partitioned between DCM and aqueous NaHCO₃. The organic layer was washed by aqueous NaHCO₃ several times and was dried over Na₂SO₄. Removal of solvent afforded 1.56 g desired product (the yield is 96.9%).

Example 7

General Method for Formation of Carbamate. Following is a Typical Example for the Formation of Carbamate. Preparation of I-76

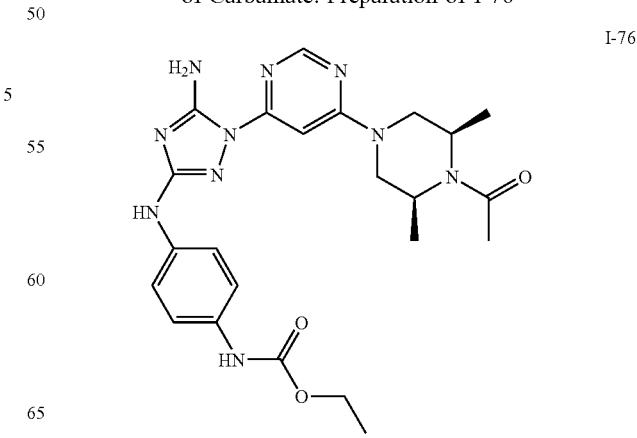

I-76

To a solution of 1-((2S,6R)-4-(6-(3-(4-aminophenylamino)-5-amino-1H-1,2,4-triazol-1-yl)pyrimidin-4-yl)-2,6-dimethylpiperazin-1-yl)ethanone (21 mg, 0.05 mmol) in 2 ml DMF was added ethyl chloroformate (6.5 mg, 0.06 mmol, 1.2 equiv.). A drop of DIEA was also added to the reaction. The reaction was stirred at room temperature over 20 min. The reaction crude was injected onto P-HPLC and 18 mg of desired product was obtained as a TFA salt.

Example 8

General Method for Formation of a Urea

The following is a typical example for the formation of a urea:

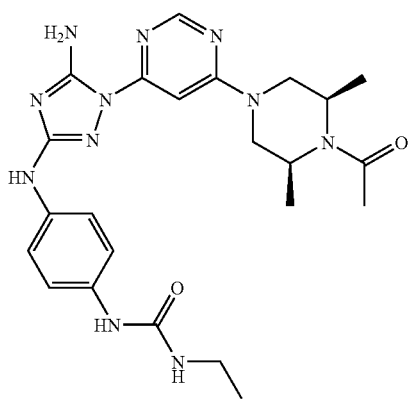

I-67

To a solution of 1-((2S,6R)-4-(6-(3-(4-aminophenylamino)-5-amino-1H-1,2,4-triazol-1-yl)pyrimidin-4-yl)-2,6-dimethylpiperazin-1-yl)ethanone (21 mg, 0.05 mmol) in 2 ml DMF was added isocyanatoethane (4.2 mg, 0.06 mmol, 1.2 equiv.). A drop of DIEA was also added to the reaction. The reaction was stirred at room temperature over 20 min. The reaction crude was injected onto P-HPLC and 17 mg of desired product was obtained as a TFA salt.

Example 9

Preparation of 9

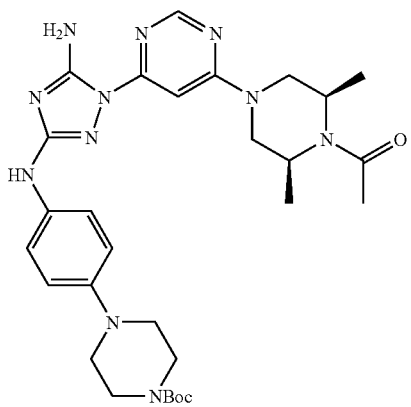

9

To a solution of 3 (1.58 g, 12.0 mmol) and tert-butyl 4-(4-((Z)-1-cyano-2-phenylisoureido)phenyl)piperazine-1-carboxylate (2.10 g, 5.0 mmol) in 6 ml NMP was added 1 ml DIEA. The reaction was sealed in a microwave reaction tube and heated in a microwave reactor at 180 degree over 6 min. The reaction was cooled to room temperature and partitioned between ethyl acetate and water. The organic layer was washed with water twice and was dried over Na2SO4. Removal of solvent left yellow solid. This solid was washed by DCM to afford a white solid. NMR in DMSO-d6: 8.86 (s, 1H); 8.38 (s, 1H); 7.70 (bs, 2H); 7.48 (d, 2H); 6.90 (d, 2H); 6.70 (s, 1H); 4.65-4.15 (m, 4H); 3.45 (m, 4H); 3.18 (m, 2H); 2.98 (m, 4H); 2.20 (s, 3h); 1.38 (s, 9H); 1.22 (m, 6H); LC/MS (M+1=592.3).

Example 10

Preparation of 1-((2S,6R)-4-(6-(3-(4-(piperazin-1-yl)phenylamino)-5-amino-1H-1,2,4-triazol-1-yl)pyrimidin-4-yl)-2,6-dimethylpiperazin-1-yl)ethanone (10)

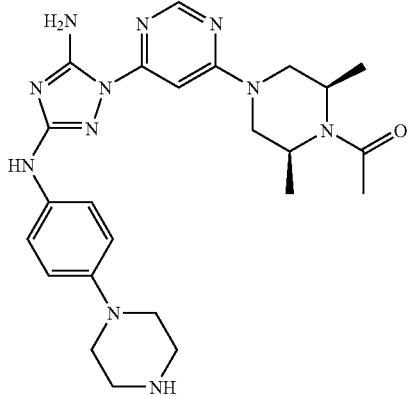

10

To a solution of 9 (1.0 g, 1.70 mmol) in 15 ml DCM was added 5 ml TFA. The reaction was stirred at room temperature over 30 min. HPLC showed the completion of the reaction. The solvent was removed in vacuum and the resulting oily material was partitioned between DCM and aqueous NaHCO3. The organic layer was washed by aqueous NaHCO3 several times and was dried over Na2SO4. Removal of solvent afforded 805 mg desired product (the yield is 96.9%).

141
Example 11
Preparation of I-113
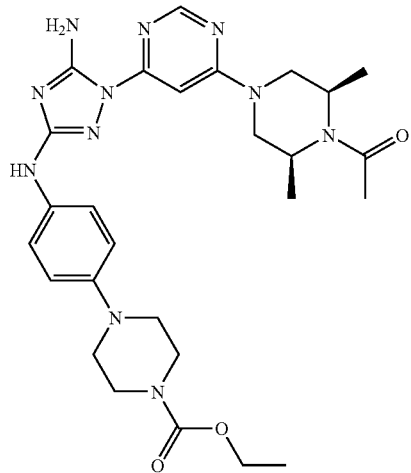
The general method for formation of carbamate as described above was utilized here to prepare I-113.
142
Example 12
Preparation of I-60
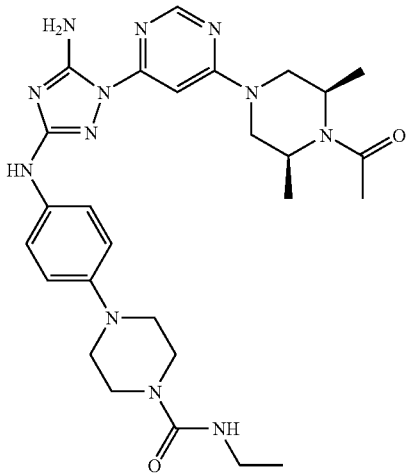
The general method for formation of urea as described above was utilized here to prepare I-60.
Scheme 4:
Route to diamino triazole compounds
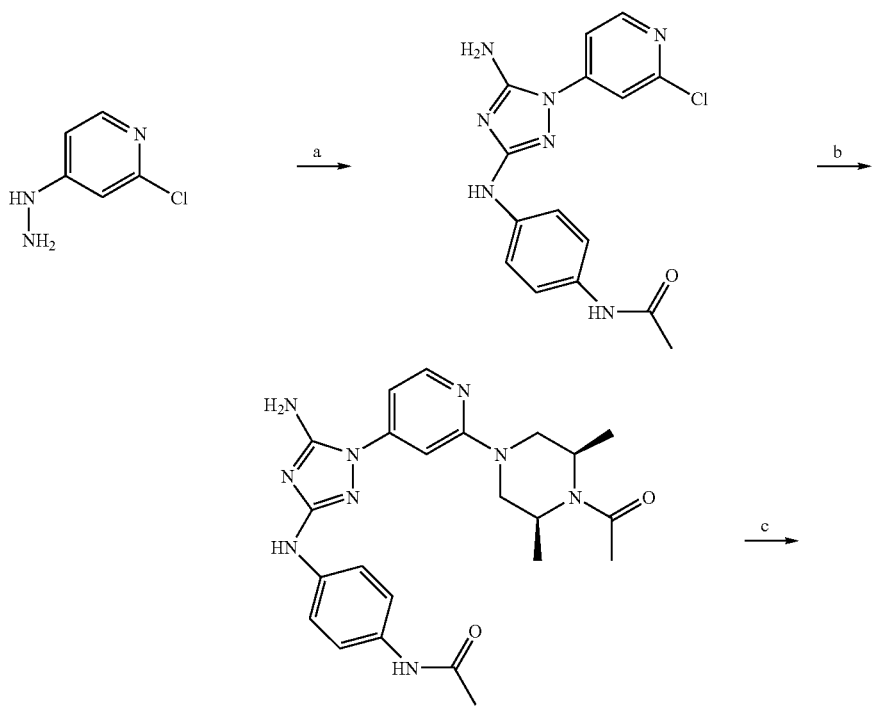

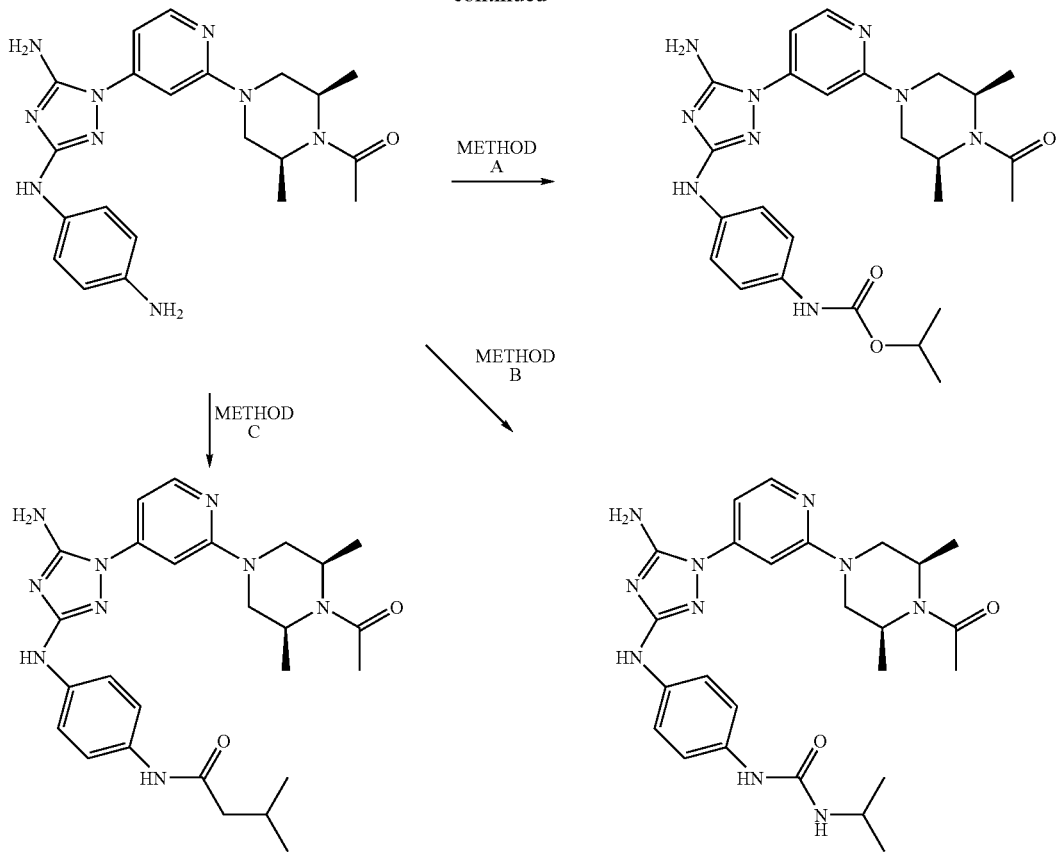
(a) N-cyano-N'-(4-acetamidophenyl)-O-phenylisourea, NMP, DIEA, MW, 220° C.; (b) i: cis-2,6-dimethylpierazine, NMP, MW, 250° C., ii: Ac$_2$O, base; (c) 6N HCl, 95° C.;
METHOD A: isopropyl chloroformate, DIEA, DMF;
METHOD B: isopropyl isocyanate, DIEA, DMF;
METHOD C: isovaleric acid, DCC, DCM.
Scheme 5:
Route to diamino triazole compounds
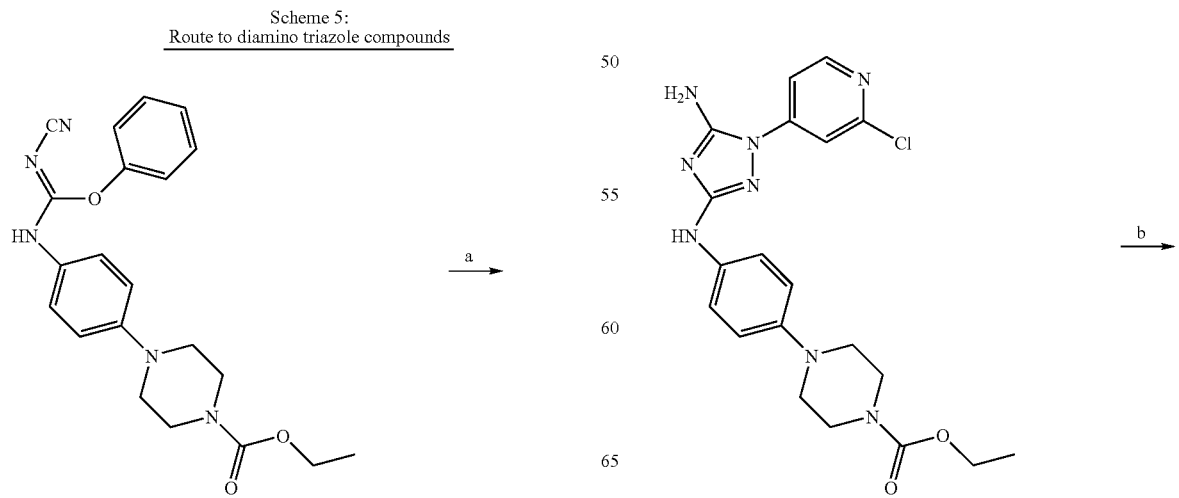

-continued

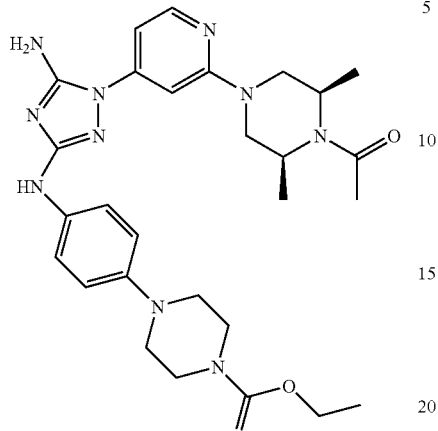

1-(2-chloropyridin-4-yl)-hydrazine, NMP, MW, 220° C.;
(b) cis-2,6-dimethylpiperazine, NMP, MW, 250° C.

Example 13

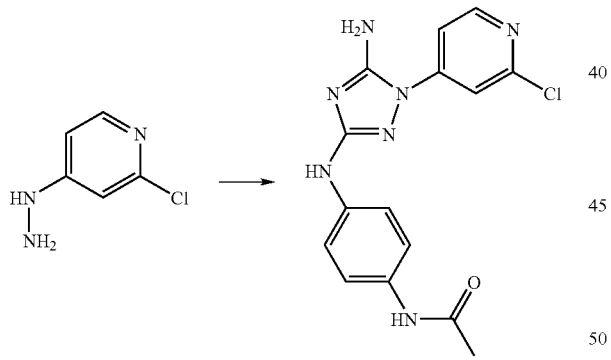

N-{4-[5-Amino-1-(2-chloro-pyridin-4-yl)-1H-[1,2,4]triazol-3-ylamino]-phenyl}-acetamide. A microwave reaction vessel was charged with 1.34 g of (2-Chloro-pyridin-4-yl)-hydrazine (7.48 mmol, 1.1 equiv) and 2.00 g of N-cyano-N'-(4-acetamidophenyl)-O-phenylisourea (6.80 mMol, 1 equiv). The solids were dissolved in 40 mL of NMP and 8 mL of DIEA. The sealed vessel was warmed to 220° C. for 6 min via microwave irradiation. Upon cooling, the resulting solution was poured into 200 mL of saturated sodium bicarbonate. The precipitate was collected and washed with 3×100 mL of water. After azeotropic drying (3×50 mL of acetonitrile) the dark yellow solid (2.0 g, 5.80 mMol, 85% yield) was used without further purification. $^1$H NMR (500 Mhz, DMSO-$d_6$) δ 9.68 (1 H, s), 9.00 (1 H, s), 8.40 (1 H, d), 7.67 (2 H, m), 7.50 (2 H, d), 7.40 (2 H, d), 6.95 (2 H, s), 2.0 (3 H, s) ppm. LCMS: 2.16 minutes/343.95 (M+H).

Example 14

Preparation of I-35

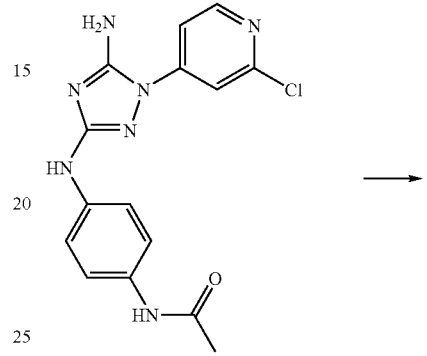

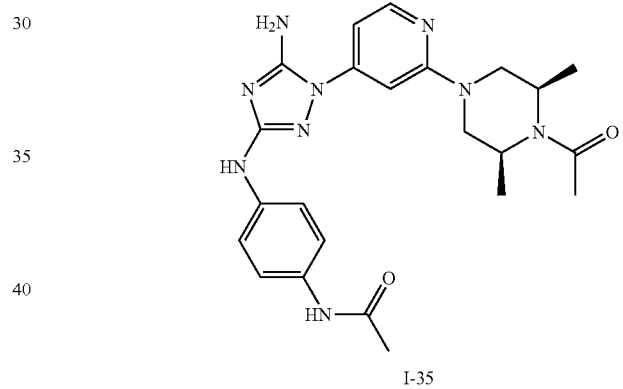

I-35

N-(4-{1-[2-(4-Acetyl-3,5-dimethyl-piperazin-1-yl)-pyridin-4-yl]-5-amino-1H-[1,2,4]triazol-3-ylamino}-phenyl)-acetamide. To a solution of 100 mg of N-{4-[5-Amino-1-(2-chloro-pyridin-4-yl)-1H-[1,2,4]triazol-3-ylamino]-phenyl}-acetamide (0.291 mMol, 1 equiv) in 5 mL of NMP was added 100 mg of cis-2,6-dimethylpiperazine (0.877 mMol, 3.0 equiv). The stirred solution was heated to 250° C. via microwave irradiation for 15 min. The reaction mixture was concentrated under vacuum by pouring and then redissolved in 5 mL of $CH_2Cl_2$ and 5 mL of DMF. To the stirred solution was added sequentially 1 mL of Hunig's base and 100 μL of acetic anhydridide. After 3 hr at 25° C., the reaction mixture was concentrated to a dark oil and purified by flash chromatography (EtOAc), yielding 15 mg of N-(4-{1-[2-(4-Acetyl-3,5-dimethyl-piperazin-1-yl)-pyridin-4-yl]-5-amino-1H-[1,2,4]triazol-3-ylamino}-phenyl)-acetamide (0.0323 mMol, 11% yield) as a yellow solid.

Example 15

Preparation of I-41

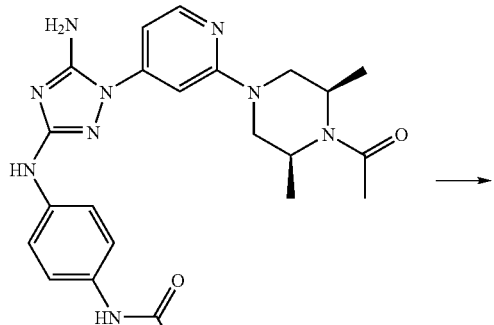

I-35

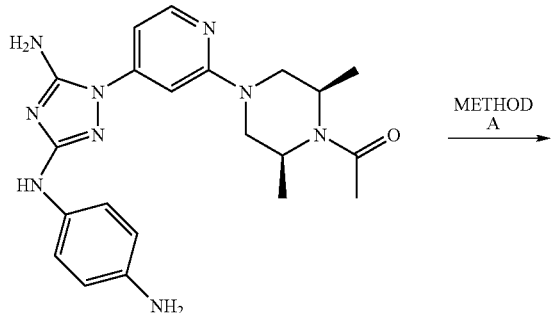

A

Compound A: 223.4 mg (0.48 mmol) of I-7 was dissolved in 2.0 ml of 6N HCl. The reaction mixture was heated to 95 degrees. After 1 hour, the reaction mixture was allowed to cool to RT. All volatiles were removed at reduced pressure. The last trace of water was azeotropically removed by co-distillation with toluene. The residue was pumped down with hi-vac overnight. Yield: Assume 100%. $^1$H NMR (500 MHz, DMSO-d6) ∂ 8.36 (s, br, 1H), 8.11 (s, br, 1H), 7.25 (s, br, 2H), 6.90 (d, br, 2H), 6.53 (d, br, 4H), 4.59-3.98 (m, 6H), 3.04 (s, br, 2H), 2.03 (m, 3H), 1.20 S, br, 6H). LC/MS: 1.51 min/422.2 (M+H).

Example 16

Preparation of I-103

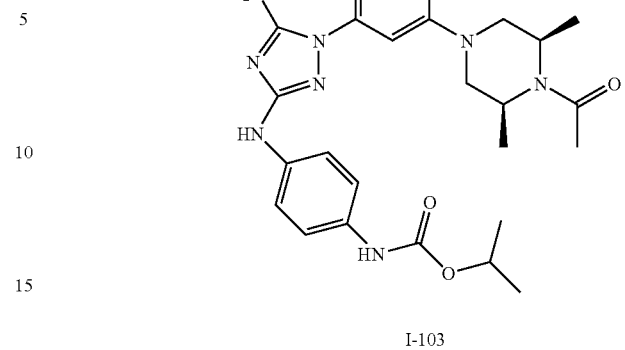

I-103

METHOD A: I-103: 46.0 mg (0.10 mmol) of I-7, 80 μl (0.46 mmol) of DIEA and 120 μl of a 1.0 M solution of isopropyl chloroformate (0.12 mmol) were dissolved in 1.0 ml of DMF. The reaction mixture was allowed to stir at RT overnight. The reaction mixture was diluted with 2.0 ml of H2O and filtered through a 0.45 μm disc. The resulting solution was then injected on to the preparative HPLC system (in 2 batches) and eluted with 5-95% Acetonitrile/Water. Yield: 8.8 mg, approximately 14%.

Example 17

Preparation of I-107

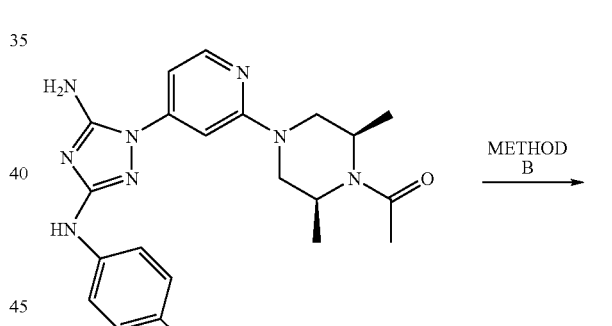

I-107

METHOD B: I-107: 55.0 mg (0.12 mmol) of I-7, 100 μl (0.56 mmol) of DIEA and 12.3 mg (0.14 mmol) of Isopropyl isocyanate were dissolved in 1.0 ml of DMF. The reaction mixture was allowed to stir at RT overnight. The reaction mixture was diluted with 2.0 ml of H2O and filtered through a 0.45 μm disc. The resulting solution was then injected on to the preparative HPLC system (in 2 batches) and eluted with 5% -95% Acetonitrile/Water. Yield: 35.3 mg, approximately 47%.

Example 18

Preparation of I-111

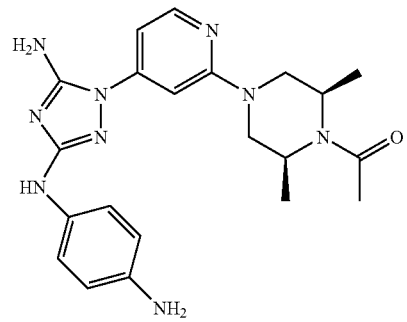

A

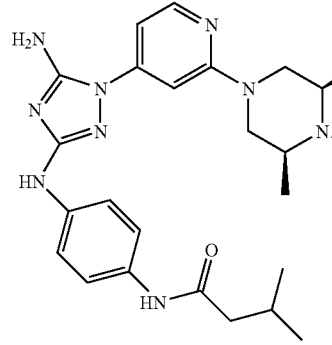

I-111

METHOD C: I-111: 31.2 mg (0.30 mmol) of Isovaleric acid was dissolved in 850 μl of CH2Cl2. Added was 150 μl (0.15 mmol) of a 1.0 M solution of DCC in CH2Cl2. After stirring for 15 min. at RT, the solution was filtered onto 55.6 mg (0.121 mmol) of I-7. The filtered material was washed through with 2.0 ml of DMF. The resulting reaction mixture was allowed to stir at RT overnight. The reaction mixture was diluted with 2.0 ml of H2O and filtered through a 0.45 μm disc. The resulting solution was then injected on to the preparative HPLC system (in 2 batches) and eluted with 10%-90% Acetonitrile/Water. Yield: 23.6 mg, approximately 40%.

Example 19

Preparation of I-111

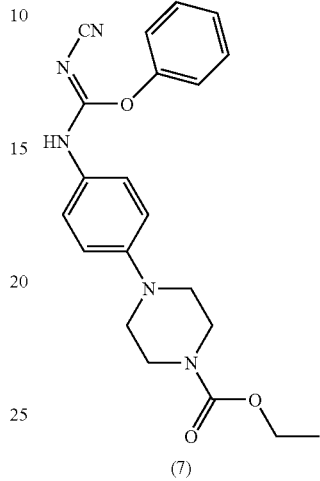

(7)

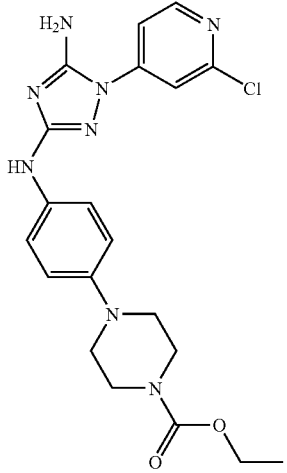

(8)

(8): 5.25 g (13.3 mmol) of (7), 3.78 g (17.5 mmol) of (2-Chloro-pyridin-4-yl)-hydrazine and 13.3 ml (74.7 mmol) of DIEA were suspended in 26.6 ml of NMP. The reaction mixture was capped and heated to 220 degrees C. via microwave irradiation. After 6 min., the reaction mixture was allowed to cool to RT. The reaction mixture was then poured onto a saturated aqueous solution of sodium bicarbonate. This aqueous phase was diluted with EtOAc and the layers were separated. The organic was dried over MgSO4, filtered and evaporated to dryness. This crude material was chromatographed on 6 inches of silica gel and eluted with 5-9% MeOH/CH2Cl2. The still slightly crude material was recrystallized from EtOAc/Hexane. Yield: 1.38 g, approximately 23%.

Example 20

Preparation of I-113

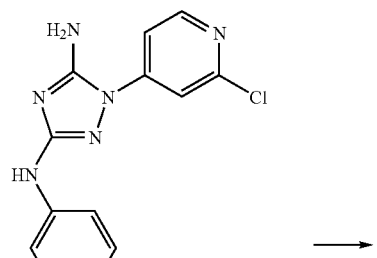

9

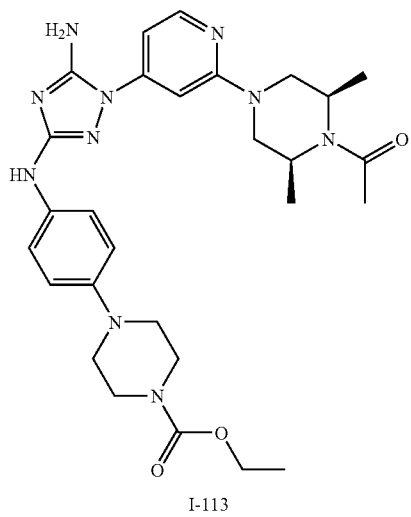

I-113

I-55: 603.6 mg (1.36 mmol) of (9) and 622.5 mg (5.5 mmol) of 2,6-Dimethyl piperazine were suspended in NMP. The reaction mixture was warmed to 250 degrees via microwave irradiation. After 15 min., the reaction mixture was allowed to cool to RT. Added was 130 μl (1.6 mmol) of pyridine followed by 1.3 ml (13.8 mmol) of Acetic Anhydride. After 30 min., the reaction mixture was slowly added to a saturated solution of sodium bicarbonate. The product was extracted with EtOAc, dried over MgSO4, filtered and evaporated to dryness. This crude material was chromatographed on 6 inches of silica gel and eluted with 5-9% MeOH/CH$_2$Cl$_2$. Yield: 108 mg, approximately 14%.

Example 21

NMR and Mass Spectrometry of Compounds

Analytical data for certain compounds of the present invention was collected and recorded as follows: Proton NMR was collected using a Bruker AMX 500 instrument and appropriate solvent. The LC/MS method used a Hypersil BDS C18 5 micron 2.1×50 mm column with a flow rate of 1.0 ml/min with an appropriate gradient. Mass spectrometer samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spectrometer analysis consisted of acetonitrile-water mixtures. TFA in some instances. Table 2 below depicts exemplary LC mass spectral data (LC/MS), retention time (RT) and $^1$H-NMR data for certain compounds of the present invention, wherein compound numbers in Table 2 correspond to the compounds depicted in Table 1 (empty cells indicate that the test was not performed).

TABLE 2

| Cmpd # | LC/MS | RT | NMR |
|---|---|---|---|
| 1 | | 2.11 | 500MHZ CH3CN-d3: 8.05(m, 1H), 7.75(d, 2H), 7.6(d, 2H), 7.2(m, 2H), 3.9(m, 7H), 3.7(m, 6H), 2.15(s, 3H) 2.0(m, 5H) |
| 2 | 479.00 | 1.96 | 1H NMR(500MHZ, DMSO-d6) d 8.95(1H, br s), 8.39(1H, d), 7.73(2H, br s), 7.51(2H, d), 6.99(2H, br s), 6.61(1H, d), 3.88(7H, m), 3.63(5H, m), 3.44(2H, t), 3.40(2H, t), 1.95-1.93(3H, m), 1.82(2H, m) ppm. |
| 3 | 451.00 | 1.76 | 1H NMR(500MHZ, DMSO-d6) d 8.86(1H, s), 8.40(1H, s), 7.73(2H, s), 7.69(1H, t), 7.50(2H, d), 6.89(2H, d), 6.80(1H, s), 4.30(2H, t), 3.83(2H, m), 3.71(5H, m), 3.42(4H, m), 3.30(3H, m), 3.0(4H, m), 2.60(2H, m) ppm. |
| 4 | 534.00 | 1.96 2.47 | 1H NMR(500MHZ, DMSO-d6) d 9.05(1H, br s), 8.40(1H, d), 7.78(2H, br s), 7.56(2H, br s), 7.40-6.90(3H, m), 6.63(1H, br s), 3.98-3.60(8H, m), 3.54(1H, m), 3.40(2H, m), 3.42(4H, m), 3.0(4H, m) ppm. |
| 5 | | 2.44 | |
| 6 | | 2.43 | |
| 7 | | 2.48 | |
| 8 | | 2.59, 2.61 | |

TABLE 2-continued

| Cmpd # | LC/MS | RT | NMR |
|---|---|---|---|
| 9 | | 2.65 | |
| 10 | 437.20 | 1.50 | DMSO-d6: 9.42(bs, 1h0; 8.32(d, 1H); 7.81(bs, 2H); 7.68(d, 2H); 7.49(m, 2h); 6.65(d, 1H) 3.60-4.00(m, 6H); 3.42(m, 2H); 3.08(m, 6H); 1.75-1.98(m, 5H); |
| 11 | 451.10 | 2.20 | DMSO-d6: 9.6(s, 1H); 9.03(s, 1H); 8.35(d, 1H); 7.80(bs, 2H); 7.45(d, 2H); 7.42(d, 2H); 6.62(m, 1H); 4.55(m, 1H); 3.55-3.95(m, 6H); 3.43(m, 2H); 1.75-1.95(m, 5H); 1.95(s, 3H)1.30(dd, 6H) |
| 12 | 465.10 | 1.70 | DMSO-d6: 10.90(bs, 0.9H); 9.55(s, 1H); 8.36(d, 1H); 7.82(bs, 2H); 7.75(d, 2H); 7.50(m, 2H); 6.63(m, 1H); 3.40-3.95(m, 12H); 1.75-1.98(m, 5H); 1.02(t, 6H) |
| 13 | 477.00 | 1.80 | DMSO-d6: 9.52(s, 1H); 8.41(d, 1H); 7.81(bs, 2H); 7.75(m, 2H); 7.51(m, 2H); 6.65(m, 1H); 3.40-3.95(m, 6H); 3.45(m, 6H); 1.40-1.98(m, 11H); |
| 14 | 437.00 | 2.10 | 500MHZ(dmso) 9.00(s, 1H), 8.05(d, 1H), 7.49(d, 1H), 7.18(m, 2H), 7.17-6.95(complex m, 4H), 3.76(complex m, 6H), 3.76(m, 4H), 3.69(dd, 2H), 1.94(m, 2H) ppm |
| 15 | | 2.72 | |
| 16 | | 2.60 | 500MHZ, DMSO-d6: 9.1(br m, 1H), 8.4(s, 1H), 7.77(m, 2H), 7.6(m, 2H), 7.1(m, 2H), 6.77(s, 1H), 4.3(m, 3H), 3.8(m, 4H), 3.2(m, 7H), 2.03(s, 3H), 1.15(br m, 6H) |
| 17 | 492.00 | 2.50 | 500Hz(dmso) 8.98(s, 1H), 8.11(d, 1H), 7.51(d, 2H), 7.16-6.97(m, 4H), 6.91(m, 2H), 4.70-4.17(broad m, 2H), 4.15(d, 2H), 3.78(m, 4H), 3.24(m, 2H), 3.13(m, 4H), 2.03(s, 3H), 1.23(m, 6H) ppm |
| 18 | 461.00 | 2.90 | 500Hz(dmso) 8.92(s, 1H), 8.03(d, 1H), 7.47(d, 2H), 7.20-6.93(br m, 4H), 6.91(m, 2H), 3.75(m, 8H), 3.03(m, 4H), 2.21(m, 2H), 1.68(s, 8H) ppm |
| 19 | 435.00 | 2.70 | 500Hz(dmso) 9.00(s, 1H), 8.00(d, 1H), 7.48(d, 2H), 7.18(m, 1H), 7.07(br s, 2H), 7.03(s, 1H), 6.93(d, 2H), 3.75(dd, 4H), 3.71(dd, 4H), 3.05(m, 4H), 1.81(m, 4H), 1.55(m, 4H) ppm |
| 20 | 409.00 | 2.20 | DMSO-d6: 9.70(bs, 2H); 9.35(bs, 1H); 8.35(d, 1h); 7.80(bs, 2H); 7.68(d, 2H); 7.22(d, 2H); 6.62(m, 1H); 3.62-3.98(m, 6H); 3.35-3.45(m, 2H); 1.75-1.98(m, 5H) |
| 21 | 509.00 | 3.10 | DMSO-d6: 9.02(bs, 1H); 8.98(s, 1H); 8.35(d, 1H); 7.76(bs, 2H); 7.45(d, 2H); 7.28(d, 2H); 6.62(m, 1H); 3.55-4.00(m, 6H_; 3.42-3.50(m, 2H); 1.72-1.98(m, 5H); 1.42(s, 9H) |
| 22 | 477.00 | 3.30 | 500MHZ(dmso) 9.08(br s, 1H), 8.42(s, 1H), 7.78(br s, 2H), 7.58(d, 2H), 7.12(br s, 2H), 6.81(s, 1H), 4.62(m, 1H), 4.43(m, 1H), 3.92(d, 1H), 3.81(m, 4H), 3.60(m, 1H), 3.20(m, 4H), 2.94(ddd, 1H), 2.84(ddd, 1H), 2.76(t, 1H), 2.30(m, 2H), 2.18(m, 1H), 1.65(m, 1H) |
| 23 | 477.00 | 3.20 | |
| 24 | 533.00 | 3.30 | |
| 25 | 561.10 | 3.80 | DMSO-d6: 9.52(s, 1H); 9.02(s, 1H); 8.35(d, 1H); 7.74(bs, 2H); 7.48(m, 4H); 6.60 m, 1H); 3.55-4.00(m, 6H); 3.45(m, 2H); 2.15(m, 1H); 1.75-1.95(m, 9H); 1.15-1.45(m, 7H); 0.85-0.95(m, 5H) |
| 26 | 521.00 | 2.40 | DMSO-d6: 9.62(s, 1H); 9.02(s, 1H); 8.35(d, 1H); 7.74(bs, 2H); 7.48(m, 4H); 6.62(m, 1H); 3.55-4.00(m, 8H); 3.45(m, 4H); 2.45(m, 1H); 1.75-1.95(m, 5H); 1.60(m, 4H) |
| 27 | 514.00 | 2.10 | DMSO-d6: 10.28(s, 1H); 9.18(s, 1H); 9.15(s, 1H); 8.76(d, 1H); 8.35(d, 2H); 7.78(bs, 2H); 7.54-7.60(m, 5H); 6.62(m, 1H); 3.55-4.00(m, 6H); 3.40-3.45(m, 2H); 1.75-1.98(m, 5H) |
| 28 | 514.00 | 2.10 | DMSO-d6: 10.40(s, 1H); 9.18(s, 1H); 8.80(d, 2H); 8.40(d, 1H); 7.90(d, 2H); 7.78(bs, 2H); 7.54-7.60(m, 4H); 6.62(m, 1H); 3.55-4.00(m, 6H); 3.40-3.45(m, 2H); 1.75-1.98(m, 5H) |
| 29 | 503.00 | 2.60 | DMSO-d6: 9.73(s, 1H); 9.18(s, 1H); 8.42(d, 1H); 8.34(s, 1H); 9.78(s, 1H); 9.77(bs, 2H); 7.55(m, 4H0; 6.95(s, 1H); 6.63(m, 1H); 3.55-4.00(m, 6H); 3.40-3.45(m, 2H); 1.75-1.98(m, 5H) |
| 30 | 503.00 | 2.60 | DMSO-d6: 9.95(s, 1H); 9.13(s, 1H); 8.34(d, 1H); 7.92(s, 1H); 7.78(bs, 2H); 7.55(m, 4H); 7.26(d, 1H); 6.65(m, 2H); 3.55-4.00(m, 6H); 3.40-3.45(m, 2H); 1.75-1.98(m, 5H) |
| 31 | 549.00 | 2.70 | |
| 32 | 549.00 | 2.75 | |
| 33 | 507.10 | 2.30 | DMSO-d6: 9.02(bs, 1H); 8.40(d, 1H); 7.75(bs, 2H); 7.50(m, 2H); 7.03(m, 2H); 6.60(m, 1H); 3.60-4.00(m, 8H); 3.45(m, 4H); 2.45(m, 2H); 1.75-2.00(m, 5H); 1.15(d, 6H) |
| 34 | 578.10 | 2.80 | DMSO-d6: 8.88(s, 1H); 8.35(d, 1H); 7.65(bs, 2H); 7.48(d, 2H); 6.85(d, 2H); 6.62(m, 1H0; 3.40-4.00(m, 12H); 2.94(m, 4H); 1.75-2.00(m, 5H); 1.40(s, 9H) |
| | 578.20 | 2.70 | |
| | 578.30 | 2.70 | |
| | 578.40 | 2.70 | DMSO-d6: 08.85(s, 1H), 8.31(d, 1H), 7.69(s, 2H), 7.45(d, 2H), 6.85(d, 2H); 6.62(m, 1H); 4.00-3.55(m, 6H); 3.40(m, 6H); 2.92(m, 4H); 2.00-1.75(m, 5H); 1.32(s, 9H) |
| | | | DMSO-d6: 9.25(bs, 1H); 8.35(d, 1H); 7.80(bs, 2H); 7.62(m, 2H); 7.22(m, 2H); 6.62(m, 1H); 4.00-3.55(m, 10H); 3.50(m, 2H); 3.28(m, 4H); 2.32(m, 3H); 2.00-1.75(m, 5H); 1.35(s, 9H) |
| 35 | 464.08 | 1.63 | 1H NMR(500MHZ, MeOD-d4) d 8.14(1H, d), 7.48(2H, d), 7.40(3 H, m), 7.03(1H, s), 6.95(1H, d), 3.70(2H, m), 3.30(4H, m), 2.15(3 H, s), 2.09(3H, s), 1.30(6H, d) ppm. |
| 36 | 562.10 | 2.50 | DMSO-d6: 9.02(bs, 1H); 8.38(d, 1H); 7.73(bs, 2H); 7.50(m, 2H); 7.03(m, |

TABLE 2-continued

| Cmpd # | LC/MS | RT | NMR |
|---|---|---|---|
| | | | 2H); 6.60(m, 1H); 3.30-4.00(m, 12H); 3.08(m, 4H); 1.75-2.00(m, 5H); 1.19(s, 9H) |
| 37 | 548.10 | 2.30 | DMSO-d6: 9.02(bs, 1H); 8.38(d, 1H); 7.73(bs, 2H); 7.52(m, 2H); 7.03(m, 2H); 6.62(m, 1H); 3.30-4.00(m, 12H); 3.08(m, 4H); 2.32(t, 2H); 1.75-2.00(m, 5H); 1.58(m, 2H); 0.85(t, 3H) |
| 38 | 562.20 | 2.50 | DMSO-d6: 9.02(bs, 1H); 8.38(d, 1H); 7.73(bs, 2H); 7.52(m, 2H); 7.03(m, 2H); 6.62(m, 1H); 3.30-4.00(m, 12H); 3.08(m, 4H); 2.22(d, 2H); 1.75-2.00(m, 6H); 0.88(d, 6H) |
| 39 | 546.10 | 2.20 | DMSO-d6: 9.02(bs, 1H); 8.38(d, 1H); 7.73(bs, 2H); 7.52(m, 2H); 7.03(m, 2H); 6.62(m, 1H); 3.30-4.00(m, 12H); 3.08(m, 4H); 1.75-2.00(m, 6H); 0.72(m, 4H) |
| 40 | 560.10 | 2.40 | DMSO-d6: 9.02(bs, 1H); 8.38(d, 1H); 7.73(bs, 2H); 7.52(m, 2H); 7.03(m, 2H); 6.62(m, 1H); 3.30-4.00(m, 12H); 3.08(m, 4H); 2.10-2.20(m, 4H); 1.75-2.00(m, 8H) |
| 41 | 590.10 | 2.20 | DMSO-d6: 9.02(bs, 1H); 8.38(d, 1H); 7.73(bs, 2H); 7.52(m, 2H); 7.03(m, 2H); 6.62(m, 1H); 3.50-4.00(m, 12H); 3.37-4.43(m, 4H); 3.08(m, 4H); 2.90(m, 1H); 1.75-2.00(m, 5H); 1.60(m, 4H) |
| 42 | 478.10 | 1.60 | |
| 43 | 592.20 | 2.20 | DMSO-d6: 9.02(bs, 1H); 8.40(d, 1H); 7.75(bs, 2H); 7.50(m, 2H); 7.00(m, 2H); 6.60(m, 1H); 5.18(m, 1H); 3.40-4.00(m, 16H); 3.15(m, 4H); 1.75-2.00(m, 7H) |
| 44 | 548.20 | 2.30 | DMSO-d6: 9.02(bs, 1H); 8.40(d, 1H); 7.75(bs, 2H); 7.50(m, 2H); 7.05(m, 2H); 6.60(m, 1H); 3.40-4.00(m, 12H); 3.15(m, 4H); 2.95(m, 1H); 1.75-2.00(m, 5H); 1.02(d, 6H) |
| 45 | 536.10 | 2.20 | DMSO-d6: 9.10(bs, 1H); 8.38(d, 1H); 7.75(bs, 2H); 7.60(m, 2H); 7.05(m, 2H); 6.60(m, 1H); 3.40-4.00(m, 15H); 3.15(m, 4H); 1.75-2.00(m, 5H); |
| 46 | 550.10 | 2.40 | DMSO-d6: 9.10(bs, 1H); 8.38(d, 1H); 7.75(bs, 2H); 7.60(m, 2H); 7.05(m, 2H); 6.60(m, 1H); 4.08(q, 2H); 3.40-4.00(m, 12H); 3.15(m, 4H); 1.75-2.00(m, 5H); 1.15(t, 3H) |
| 47 | 564.20, 564.50, 564.40 | 2.70, 2.60, 2.60 | DMSO-d6: 9.10(bs, 1H); 8.38(d, 1H); 7.75(bs, 2H); 7.60(m, 2H); 7.05(m, 2H); 6.60(m, 1H); 4.03(q, 2H); 3.40-4.00(m, 12H); 3.15(m, 4H); 1.75-2.00(m, 5H); 1.55(m, 2H); 0.88(t, 3H) <br> DMSO-d6: 8.88(s, 1H); 8.38(d, 1H); 7.68(bs, 2H); 7.46(d, 2H); 6.88(d, 2H); 6.60(m, 1H); 3.95(t, 2H); 4.00-3.55(m, 6H); 3.50-3.38(m, 6H); 2.98(m, 4H); 2.00-1.75(m, 5H); 1.60(m, 2H); 0.85(t, 3H) <br> DMSO-d6: 9.30(bs, 1H); 8.35(d, 1H); 7.76)bs, 2H); 7.60(m, 2H); 7.28(m, 2H); 6.60(m, 1H); 3.98(q, 2H); 4.00-3.55(m, 8H); 3.40-3.20(m, 8H); 2.30(s, 3H); 1.95-1.75(m, 5H); 1.55(m, 2H); 0.88(t, 3H) |
| 48 | 564.20 | 2.60 | DMSO-d6: 9.10(bs, 1H); 8.38(d, 1H); 7.75(bs, 2H); 7.60(m, 2H); 7.05(m, 2H); 6.60(m, 1H); 4.80(m, 1H); 3.40-4.00(m, 12H); 3.15(m, 4H); 1.75-2.00(m, 5H); 1.22(d, 6H) |
| 49 | 592.20 | 3.10 | DMSO-d6: 9.10(bs, 1H); 8.38(d, 1H); 7.75(bs, 2H); 7.60(m, 2H); 7.05(m, 2H); 6.60(m, 1H); 3.40-4.00(m, 14H); 3.15(m, 4H); 1.75-2.00(m, 5H); 0.90(s, 9H) |
| 50 | 578.20 | 3.10 | DMSO-d6: 9.10(bs, 1H); 8.38(d, 1H); 7.75(bs, 2H); 7.60(m, 2H); 7.05(m, 2H); 6.60(m, 1H); 3.40-4.00(m, 14H); 3.15(m, 4H); 1.75-2.00(m, 6H); 0.88(d, 6H) |
| 51 | 612.20 | 3.20 | DMSO-d6: 9.10(bs, 1H); 8.38(d, 1H); 7.75(bs, 2H); 7.60(m, 2H); 7.15(d, 2H); 7.05(m, 4H); 6.60(m, 1H); 3.40-4.00(m, 12H); 3.15(m, 4H); 2.22(s, 3H); 1.75-2.00(m, 6H); |
| 52 | 592.30, 592.40 | 3.00, 2.90 | DMSO-d6: 8.86(s, 1H); 8.38(d, 1H); 7.70(bs, 2H); 7.48(d, 2H); 6.90(d, 2H); 6.70(s, 1H); 4.65-4.15(m, 4H); 3.45(m, 4H); 3.18(m, 2H); 2.98(m, 4H); 2.20(s, 3h); 1.38(s, 9H); 1.22(m, 6H) <br> DMSO-d6: 9.25(bs, 1H); 8.35(s, 1H); 7.78(bs, 2H); 7.62(d, 2H); 7.23(m, 2H); 6.75(s, 1H); 4.60-4.00(m, 6H); 3.22(m, 8H); 2.28(s, 3H); 2.02(s, 3H); 1.41(s, 9H); 1.18(m, 6H) |
| 53 | 550.30 | 2.40 | DMSO-d6: 9.12(bs, 1H); 8.35(s, 1H); 7.75(bs, 2H); 7.56(m, 2H); 7.10(m, 2H); 6.76(m, 1H); 4.65-4.10(m, 4H); 3.38(s, 3h); 3.50(m, 4h); 3.15(m, 6H); 2.20(s, 3H); 1.12(m, 6H) |
| 54 | 564.30, 564.30 | 2.60, 2.60 | DMSO-d6: 9.09(bs, 1H); 8.39(s, 1H); 7.80(bs, 2H); 7.56(m, 2H); 7.08(m, 2H); 6.76(m, 1H); 4.65-4.10(m, 4H); 4.03(q, 2H); 3.50(m, 4H); 3.20-3.10(m, 6H); 2.10(s, 3H); 1.15(t, 3H); 1.12(m, 6H) <br> DMSO-d6: 9.22(bs, 1H); 8.38(s, 1H); 7.78(bs, 2H); 7.60(m, 2H); 7.20(m, 2H); 6.65(s, 1H); 4.60-4.00(m, 4H); 4.06(q, 2H); 3.80(m, 4H); 3.20(m, 6H); 2.32(s, 3H); 2.02(s, 3h); 1.18(t, 3H); 1.15(m, 6H) |
| 55 | 578.40, 578.40 | 2.80, 2.80 | DMSO-d6: 9.09(bs, 1H); 8.35(s, 1H); 7.75(bs, 2H); 7.56(m, 2H); 7.08(m, 2H); 6.76(m, 1H); 4.65-4.10(m, 4H); 4.00(q, 2H); 3.55(m, 4H); 3.30-3.10(m, 6H); 2.10(s, 3H); 1.15(t, 3H); 1.55(m, 2H); 1.12(m, 6H); 0.85(t, 3H) <br> DMSO-d6: 9.22(bs, 1H); 8.38(s, 1H); 7.78(bs, 2H); 7.60(m, 2H); 7.20(m, 2H); 6.65(s, 1H); 4.60-4.00(m, 4H); 4.00(q, 2H); 3.80(m, 4H); 3.20(m, 6H); 2.32(s, 3H); 2.02(s, 3h); 1.58(m, 2H); 1.15(m, 6H); 0.88(t, 3H) |
| 56 | 578.40 | 2.80 | DMSO-d6: 9.08(bs, 1H); 8.38(s, 1H); 7.78(bs, 2H); 7.56(m, 2H); 7.05(m, 2H); 6.75(m, 1H); 4.80(m, 1H); 4.60-4.10(m, 4H); 3.52(m, 4H); 3.25-3.05(m, 6H); 2.02(s, 3H); 1.22(d, 6H); 1.15(m, 6H)( |
| 57 | 606.40 | 3.30 | DMSO-d6: 9.08(bs, 1H); 8.38(s, 1H); 7.78(bs, 2H); 7.56(m, 2H); 7.05(m, |

TABLE 2-continued

| Cmpd # | LC/MS | RT | NMR |
|---|---|---|---|
| | | | 2H); 6.75(m, 1H); 4.60-4.10(m, 4H); 3.70(s, 2H); 3.52(m, 4H); 3.25-3.05(m, 6H); 2.02(s, 6H); 1.22(m, 6H); 0.92(s, 9H) |
| 58 | 592.40 | 3.10 | DMSO-d6: 9.08(bs, 1H); 8.38(s, 1H); 7.78(bs, 2H); 7.56(m, 2H); 7.05(m, 2H); 6.75(m, 1H); 4.60-4.10(m, 4H); 3.80(d, 2H); 3.52(m, 4H); 3.25-3.05(m, 6H); 2.02(s, 3H); 1.85(m, 1H); 1.22(m, 6H); 0.88(d, 6H) |
| 59 | 492.40 | 1.80 | DMSO-d6: 8.80(s, 1H); 8.38(s, 1H); 7.70(bs, 2H); 7.48(d, 2H); 6.85(d, 2H); 6.78(s, 1H); 4.60-4.10(m, 4H); 3.40-3.10(m, 6H); 2.95(m, 2H); 2.85(s, 2H); 2.05(s, 3H); 1.12(m, 6H) |
| 60 | 563.40 | 2.20 | DMSO-d6: 9.18(bs, 1H); 8.32(s, 1H); 7.75(bs, 2H); 7.60(d, 2H); 7.20(m, 2H); 6.76(s, 1H); 6.62(bs, 1H); 4.60-4.10(m, 4H); 3.50(m, 4H); 3.20(m, 6H); 3.08(q, 2H); 2.06(s, 3H); 1.16(m, 6H); 0.98(t, 3H) |
| 61 | 577.40 | 2.30 | DMSO-d6: 9.18(bs, 1H); 8.32(s, 1H); 7.75(bs, 2H); 7.60(d, 2H); 7.20(m, 2H); 6.76(s, 1H); 6.62(bs, 1H); 4.60-4.10(m, 4H); 3.55(m, 4H); 3.22(m, 6H); 3.00(m, 2H); 2.06(s, 3H); 1.40(m, 2H); 1.16(m, 6H); 0.80(t, 3H) |
| 62 | 577.40 | 2.30 | DMSO-d6: 9.22(bs, 1H); 8.38(s, 1H); 7.76(bs, 2H); 7.62(d, 2H); 7.22(m, 2H); 6.76(s, 1H); 6.32(m, 1H); 4.60-4.10(m, 4H); 3.72(m, 1H); 3.55(m, 4H); 3.22(m, 6H); 2.02(s, 3H); 1.18(m, 6H); 1.02(d, 6H) |
| 63 | 591.40 | 2.50 | DMSO-d6: 9.22(bs, 1H); 8.38(s, 1H); 7.76(bs, 2H); 7.62(d, 2H); 7.22(m, 2H); 6.76(s, 1H); 5.92(m, 1H); 4.60-4.10(m, 4H); 3.55(m, 4H); 3.22(m, 6H); 2.02(s, 3H); 1.22(s, 9H); 1.18(m, 6H) |
| 64 | 617.40 | 2.60 | DMSO-d6: 9.22(bs, 1H); 8.38(s, 1H); 7.76(bs, 2H); 7.62(d, 2H); 7.22(m, 2H); 6.76(s, 1H); 5.92(m, 1H); 4.60-4.10(m, 4H); 3.40-3.60(m, 5H); 3.22(m, 6H); 2.02(s, 3H); 1.50-1.70(m, 4H); 1.00-1.30(m, 12H) |
| 65 | 635.40 | 2.40 | DMSO-d6: 9.15(bs, 1H); 8.35(s, 1H); 7.76(bs, 2H); 7.55(d, 2H); 7.20(m, 2H); 6.76(s, 1H); 6.66(m, 1H); 4.60-4.10(m, 4H); 4.02(q, 2H); 3.50(m, 4H); 3.25-3.05(m, 8H); 2.50(m, 2H)2.20(s, 3H); 1.08(m, 9H) |
| 66 | 647.30 | 2.60 | DMSO-d6: 9.10(s, 1H); 8.35(m, 2H); 7.75(bs, 2H); 7.60(m, 2H); 7.22(m, 1H); 7.10(m, 2H); 6.85(M, 1H); 6.80(s, 1H); 6.50(m, 1H); 4.60-4.10(m, 4H); 3.60(m, 4H); 3.18(m, 6H); 2.05(s, 3H); 1.12(m, 6H) |
| 67 | 494.30 | 2.50 | DMSO-d6: 8.92(s, 1H); 8.35(s, 1h); 8.12(s, 1H); 7.75(bs, 2H); 7.40(d, 2H); 7.22(d, 2H); 6.73(s, 1H); 5.90(bs, 1H); 4.60-4.10(m, 4H); 3.20(m, 2H); 3.10(q, 2H); 2.02(s, 3H); 1.15(bs, 6H); 1.02(t, 3H) |
| 68 | 508.30 | 2.70 | DMSO-d6: 8.92(s, 1H); 8.35(s, 1h); 8.12(s, 1H); 7.75(bs, 2H); 7.40(d, 2H); 7.22(d, 2H); 6.73(s, 1H); 5.90(bs, 1H); 4.60-4.10(m, 4H); 3.20(m, 2H); 3.10(q, 2H); 2.02(s, 3H); 1.40(m, 2H); 1.15(bs, 6H); 1.02(t, 3H) |
| 69 | 508.30 | 2.70 | DMSO-d6: 8.92(s, 1H); 8.35(s, 1h); 8.12(s, 1H); 7.75(bs, 2H); 7.40(d, 2H); 7.22(d, 2H); 6.73(s, 1H); 5.90(bs, 1H); 4.60-4.10(m, 4H); 3.80(m, 1H); 3.19(m, 2H); 2.02(s, 3H); 1.15(bs, 6H); 1.05(d, 6H) |
| 70 | 522.30 | 2.90 | DMSO-d6: 8.92(s, 1H); 8.35(s, 1h); 8.12(s, 1H); 7.75(bs, 2H); 7.40(d, 2H); 7.22(d, 2H); 6.73(s, 1H); 5.90(bs, 1H); 4.60-4.10(m, 4H); 3.19(m, 2H); 2.02(s, 3H); 1.22(s, 9H); 1.15(m, 6H) |
| 71 | 548.40 | 3.10 | DMSO-d6: 8.92(s, 1H); 8.35(s, 1h); 8.12(s, 1H); 7.75(bs, 2H); 7.40(d, 2H); 7.22(d, 2H); 6.73(s, 1H); 5.90(bs, 1H); 4.60-4.10(m, 4H); 3.42(m, 1H); 3.20(m, 2H); 2.02(s, 3H); 1.78(m, 2H); 1.68(m, 2H); 1.55(m, 1H); 1.30-1.00(m, 11H) |
| 72 | 566.40 | 2.70 | DMSO-d6: 8.88(s, 1H); 8.30(s, 1H); 8.22(s, 1H); 7.75(bs, 3H); 7.40(d, 2H); 7.22(d, 2H); 6.73(s, 1H); 6.10(bs, 1H); 4.60-4.10(m, 4H); 4.03(m, 2H); 3.32-3.15(m, 4H); 3.02(m, 1H); 2.55(m, 1H); 2.02(s, 3h0; 1.10(m, 9H) |
| 73 | 578.30 | 3.00 | DMSO-d6: 8.98(s, 1H); 8.60(s, 1H); 8.32(s, 1H); 7.95(s, 1h); 7.75(bs, 2H); 7.45(d, 2h); 7.28(d, 2H); 7.25(m, 1H); 7.08(m, 1H); 6.73 9s, 1H); 4.60-4.10(m, 4h); 3.15 9m, 2H); 2.02(s, 3h0; 1.15(m, 6H) |
| 74 | 610.30 | 3.40 | DMSO-d6: 9.12(s, 1H); 9.02(s, 1H); 8.35(s, 1H); 7.85(d, 1H); 7.92(s, 1H); 7.75(bs, 2H); 7.60(m, 2h); 7.48(d, 2H); 7.28(d, 2h); 7.20(m, 1H); 6.72(s, 1H); 4.60-4.10(m, 4H); 3.20(m, 2h); 2.02(s, 3h); 1.15(m, 6H) |
| 75 | 481.30 | 2.70 | DMSO-d6: 9.22(s, 1H); 9.00(s, 1H); 8.38(s, 1H); 7.70(bs, 2H); 7.45(d, 2H); 7.30(d, 2H); 7.20(m, 1H); 6.72(s, 1H); 4.60-4.10(m, 4H); 3.60(s, 3H); 3.30(m, 2H); 1.12(m, 6H) |
| 76 | 495.30<br>495.30 | 2.90<br>2.80 | DMSO-d6: 9.22(s, 1H); 9.00(s, 1H); 8.38(s, 1H); 7.70(bs, 2H); 7.45(d, 2H); 7.30(d, 2H); 7.20(m, 1H); 6.72(s, 1H); 4.60-4.10(m, 4H); 4.02(q, 2H); 3.20(m, 2H); 1.16(t, 3H); 1.12(m, 6H)<br>DMSO-d6: 9.30(bs, 1H); 9.02(bs, 1H); 8.40(s, 1H); 7.75(bs, 2H); 7.50(d, 2H); 7.35(d, 2H); 6.75(s, 1H); 4.60-4.00(m, 4H); 4.05(q, 2H); 3.23(m, 2H); 2.25(s, 3H); 2.03(s, 3H); 1.22(t, 3H); 1.18(m, 6H)( |
| 77 | 509.30 | 3.10 | DMSO-d6: 9.22(s, 1H); 9.00(s, 1H); 8.38(s, 1H); 7.70(bs, 2H); 7.45(d, 2H); 7.30(d, 2H); 7.20(m, 1H); 6.72(s, 1H); 4.60-4.10(m, 4H); 3.98(t, 2H); 3.20(m, 2H); 2.02(s, 3H); 1.55(m, 2H); 1.15(m, 6H); 0.89(t, 3H) |
| 78 | 509.30<br>509.40 | 3.10<br>3.10 | DMSO-d6: 9.22(s, 1H); 9.02(s, 1H); 8.38(s, 1H); 7.78(bs, 2H); 7.50(d, 2H); 7.32(d, 2H); 6.72(s, 1H); 4.84(m, 1H); 4.60-4.00(m, 4H); 3.28(m, 2H); 2.02(s, 3H); 1.22(d, 6H); 1.18(m, 6H) |
| 79 | 523.30<br>523.30 | 3.30<br>3.30 | DMSO-d6: 9.23(s, 1H); 9.01(s, 1H); 8.38(s, 1H); 7.78(bs, 2H); 7.48(d, 2H); 7.32(d, 2H); 6.78(s, 1H); 4.60-4.10(m, 4H); 3.85(d, 2H); 3.20(m, |

TABLE 2-continued

| Cmpd # | LC/MS | RT | NMR |
|---|---|---|---|
| | | | 2H); 2.02(s, 3H); 1.88(m, 1H); 1.15(m, 6H); 0.86(d, 6H), DMSO-d6: 9.22(s, 1H); 9.02(s, 1H); 8.38(s, 1H); 7.78(bs, 2H); 7.50(d, 2H); 7.32(d, 2H); 6.72(s, 1H); 4.60-4.00(m, 4H); 3.80(d, 2H); 3.25(m, 2H); 2.02(s, 3H); 1.88(m, 1H); 1.18(m, 6H); 0.98(d, 6H) |
| 80 | 537.30<br>537.30 | 3.50<br>3.50 | DMSO-d6: 9.23(s, 1H); 9.01(s, 1H); 8.38(s, 1H); 7.78(bs, 2H); 7.48(d, 2H); 7.32(d, 2H); 6.78(s, 1H); 4.60-4.10(m, 4H); 3.78(d, 2H); 3.20(m, 2H); 2.02(s, 3H); 1.15(m, 6H); 0.90(s, 9H)<br>DMSO-d6: 9.22(s, 1H); 9.02(s, 1H); 8.38(s, 1H); 7.78(bs, 2H); 7.50(d, 2H); 7.32(d, 2H); 6.72(s, 1H); 4.60-4.00(m, 4H); 3.80(s, 2H); 3.25(m, 2H); 2.02(s, 3H); 1.18(m, 6H); 0.92(s, 9H) |
| 81 | 557.30<br>557.30 | 3.50<br>3.50 | DMSO-d6: 9.88(s, 1H); 9.03(s, 1H); 8.33(s, 1H); 7.74(bs, 2h0; 7.53(d, 2H); 7.32(d, 2H0; 7.18(d, 2h); 7.06(d, 2H0; 6.72(s, 1H); 4.60-4.10(m, 4H); 3.16(m, 2H); 2.38(s, 3H0; 2.02(s, 3H); 1.15(m, 6H)<br>DMSO-d6: 9.86(bs, 1H); 9.03(s, 1H); 8.35(s, 1H); 7.76(bs, 2H); 7.55(d, 2H); 7.35(d, 2H); 7.21(d, 2H); 7.05(d, 2H); 6.75(s, 1H); 4.60-4.00(m, 4H); 3.22(m, 2H); 2.30(s, 3H); 2.02(s, 3H); 1.18(m, 6H) |
| 82 | 605.30 | 4.40 | DMSO-d6: 9.25(s, 1H); 8.95(s, 1H); 8.35 9s, 1H); 7.72(bs, 2H); 7.45(d, 2H); 7.32(d, 2H); 6.65(s, 1H); 4.60-4.10(m, 6H); 3.20(m, 2H); 2.05(s, 3H); 1.98(m, 2H); 1.65(m, 2H); 1.45(m, 1H); 1.38(m, 1H); 1.18-1.00(m, 8H); 0.85(d, 6H); 0.78(d, 3H) |
| 83 | 605.30 | 4.40 | DMSO-d6: 9.25(s, 1H); 8.95(s, 1H); 8.35 9s, 1H); 7.72(bs, 2H); 7.45(d, 2H); 7.32(d, 2H); 6.65(s, 1H); 4.60-4.10(m, 6H); 3.20(m, 2H); 2.05(s, 3H); 1.98(m, 2H); 1.65(m, 2H); 1.45(m, 1H); 1.38(m, 1H); 1.18-1.00(m, 8H); 0.85(d, 6H); 0.78(d, 3H) |
| 84 | 523.30 | 3.30 | DMSO-d6: 8.98(bs, 1H); 8.94(s, 1H); 8.38(s, 1H); 7.72(bs, 2H); 7.45(d, 2H); 7.25(d, 2H); 6.73(s, 1H); 4.60-4.10(m, 4H); 3.20(m, 2H); 2.02(s, 3H); 1.40(s, 9H); 1.15(m, 6H) |
| 85 | 494.30 | 2.40 | DMSO-d6: 8.92(s, 1H); 8.32(d, 1H); 8.05(s, 1H); 7.72(bs, 2h); 7.38(d, 2H); 7.22(d, 2h); 6.63(m, 1H); 6.02(bs, 1H); 4.10-3.55(m, 6H); 3.40(m, 2H); 3.00(t, 2H); 2.00-1.75(m, 5H); 1.40(m, 2H); 0.85(t, 3H) |
| 86 | 494.30 | 2.40 | DMSO-d6: 8.92(s, 1H); 8.32(d, 1H); 8.05(s, 1H); 7.72(bs, 2h); 7.38(d, 2H); 7.22(d, 2h); 6.63(m, 1H); 6.02(bs, 1H); 4.10-3.55(m, 7H); 3.40(m, 2H); 1.75-2.00(m, 5H); 1.05(d, 6H) |
| 87 | 508.30 | 2.70 | |
| 88 | 534.30 | 2.90 | DMSO-d6: 8.92(s, 1H); 8.32(d, 1H); 8.05(s, 1H); 7.72(bs, 2h); 7.38(d, 2H); 7.22(d, 2h); 6.63(m, 1H); 6.02(bs, 1H); 4.10-3.55(m, 6H); 3.40(m, 3H); 1.45-2.10(m, 10H); 1.35-1.00(m, 5H) |
| 89 | 552.30 | 2.50 | |
| 90 | 467.20 | 2.40 | DMSO-d6: 9.25(bs, 1H); 8.98(s, 1H); 8.38(s, 1H); 7.75(bs, 2H); 7.42(d, 2H); 7.28(d, 2H); 6.60(m, 1H); 4.10-3.55(m, 6H); 3.60(s, 3H); 3.42(m, 2H); 2.00-1.75(m, 5H) |
| 91 | 481.30 | 2.60 | DMSO-d6: 9.25(bs, 1H); 8.98(s, 1H); 8.38(s, 1H); 7.75(bs, 2H); 7.42(d, 2H); 7.28(d, 2H); 6.60(m, 1H); 4.03(q, 2H); 4.10-3.55(m, 6H); 3.42(m, 2H); 2.00-1.75(m, 5H); 1.18(t, 3H) |
| 92 | 495.30 | 2.90 | DMSO-d6: 9.25(bs, 1H); 8.98(s, 1H); 8.38(s, 1H); 7.75(bs, 2H); 7.42(d, 2H); 7.28(d, 2H); 6.60(m, 1H); 4.10-3.55(m, 6H); 3.98(t, 2H); 3.42(m, 2H); 2.00-1.75(m, 5H); 1.58(m, 2H); 0.93(t, 3H) |
| 93 | 495.30 | 2.80 | DMSO-d6: 9.25(bs, 1H); 8.98(s, 1H); 8.38(s, 1H); 7.75(bs, 2H); 7.42(d, 2H); 7.28(d, 2H); 6.60(m, 1H); 4.82(m, 1H); 4.10-3.55(m, 6H); 3.42(m, 2H); 2.00-1.75(m, 5H); 1.20(d, 6H) |
| 94 | 509.30 | 3.10 | DMSO-d6: 9.25(bs, 1H); 8.98(s, 1H); 8.38(s, 1H); 7.75(bs, 2H); 7.42(d, 2H); 7.28(d, 2H); 6.60(m, 1H); 4.10-3.55(m, 6H); 3.60(d, 2H); 3.42(m, 2H); 2.00-1.75(m, 5H); 0.89(d, 6H) |
| 95 | 523.30 | 3.30 | DMSO-d6: 9.25(bs, 1H); 8.98(s, 1H); 8.38(s, 1H); 7.75(bs, 2H); 7.42(d, 2H); 7.28(d, 2H); 6.60(m, 1H); 4.10-3.55(m, 6H); 3.75(s, 2H); 3.42(m, 2H); 2.00-1.75(m, 5H); 0.91(s, 9H) |
| 96 | 543.30 | 3.30 | DMSO-d6: 9.85(bs, 1H); 9.05(bs, 1H); 8.32(d, 1H); 7.75(bs, 2h); 7.50(d, 2h); 7.32(d, 2H); 7.20(d, 2H); 7.05(d, 2H); 6.60(m, 1h); 4.10-3.55(m, 6H); 3.40(m, 2H); 2.25(s, 3h); 2.00-1.75(m, 5H) |
| 97 | 591.30 | 3.30 | DMSO-d6: 9.25(bs, 1H); 8.86(bs, 1h); 8.42(d, 1H); 7.75(bs, 2H); 7.45(d, 2H); 7.32(d, 2H); 6.62(m, 1H); 4.50(m, 1H); 4.10-3.55(m, 6H); 3.40(m, 2H); 2.00-1.20(m, 11H); 1.10-0.72(m, 12H) |
| 98 | 591.30 | 4.20 | DMSO-d6: 9.25(bs, 1H); 8.86(bs, 1h); 8.42(d, 1H); 7.75(bs, 2H); 7.45(d, 2H); 7.32(d, 2H); 6.62(m, 1H); 4.50(m, 1H); 4.10-3.55(m, 6H); 3.40(m, 2H); 2.00-1.20(m, 11H); 1.10-0.72(m, 12H) |
| 99 | 422.20 | 1.51 | 8.36(s, br, 1H), 8.11(s, br, 1H), 7.25(s, br, 2H), 6.90(d, br, 2H), 6.53(d, br, 4H), 4.59-3.98(m, 6H), 3.04(s, br, 2H), 2.03(m, 3H), 1.20 S, br, 6H). |
| 100 | 522.20 | 2.41 | 1H NMR(500MHZ, DMSO-d6) 9.31(s, br, 1H), 8.78(s, br, 1H), 8.11(d, 1H), 7.47(d, 2H), 7.32(d, 2H), 7.17-6.79(m, 4H), 4.14(d, 2H), 3.84(d, 4H), 3.25(d, 2H), 2.08(s, 3H), 1.91(m, 1H), 1.23(s, br, 6H), 0.93(d, 6H). |
| 101 | 494.20 | 2.06 | 1H NMR(500MHZ, DMSO-d6) 9.29(s, br, 1H), 8.96(s, br, 1H), 8.10(d, 1H), 7.47(d, 2H), 7.31(d, 2H), 7.06(s, br, 2H), 6.90(s, br, 2H), 4.09(m, 3H), 3.23(d, 2H), 2.08(s, 3H), 1.23(m, 12H). |
| 102 | 508.20 | 2.25 | 1H NMR(500MHZ, DMSO-d6) 9.23(s, br, 1H), 8.93(s, br, 1H), 8.12(d, 1H), 7.47(d, 2H), 7.29(d, 2H), 7.04(s, br, 2H), 6.83(s, br, 2H), 4.16(d, |

TABLE 2-continued

| Cmpd # | LC/MS | RT | NMR |
|---|---|---|---|
| | | | 3H), 4.00(m, 3H), 3.18(d, br, 2H), 2.07(s, 3H), 1.63(m, 2H), 1.22(s, br, 6H), 0.93(t, 3H). |
| 103 | 508.20 | 2.20 | 1H NMR(500MHZ, DMSO-d6) 9.23(s, br, 1H), 8.94(s, br, 1H), 8.10(d, 1H), 7.46(d, 2H), 7.30(d, 2H), 7.05(s, br, 2H), 6.87(s, br, 2H), 4.85(m, 1H), 4.15(d, 2H), 3.21(d, br, 2H), 2.08(s, 3H), 1.24(m, 14H). |
| 104 | 536.20 | 2.60 | 1H NMR(500MHZ, DMSO-d6) 9.26(s, br, 1H), 8.91(s, br, 1H), 8.11(d, 1H), 7.49(d, 2H), 7.31(s, br, 2H), 7.01(s, br, 2H), 6.78(s, br, 2H), 4.17(d, 2H), 3.76(s, 2H), 3.14 M, 2H), 2.07(s, 3H), 1.22(m, 7H), 0.94(m, 10H). |
| 105 | 493.40 | 1.80 | 1H NMR(500MHZ, DMSO-d6) 8.88(s, br, 1H), 8.16-8.05(m, 2H), 7.44(d, 2H), 7.23(d, 2H), 7.13-7.01(m, 2H), 6.89(s, br, 1H), 5.94(s, br, 1H), 4.15(d, 4H), 3.24(s, br, 1H), 3.08(m, 2H), 2.08(s, 3H), 1.32-1.11(m, 8H), 1.04(t, 3H). |
| 106 | 507.40 | 1.90 | 1H NMR(500MHZ, DMSO-d6) 8.88(s, br, 1H), 8.11(m, 2H), 7.42(d, 2H), 7.22(d, 2H), 7.06(s, br, 2H), 6.88(s, br, 1H), 5.99(s, br, 1H), 4.17(d, 4H), 3.22(s, br, 1H), 3.02(m, 2H), 2.08(s, 3H), 1.42(m, 2H), 1.25(m, 8H), 0.87(m, 3H). |
| 107 | 507.40 | 1.90 | 1H NMR(500MHZ, DMSO-d6) 8.87(s, br, 1H), 8.10(m, 1H), 8.02(s, br, 1H), 7.43(d, 2H), 7.23(d, 2H), 7.06(m, 2H), 6.87(s, br, 1H), 5.84(s, br, 1H), 4.15(d, 4H), 3.74(m, 1H), 3.23(m, 1H), 2.07(s, 3H), 1.25(m, 8H), 1.07(m, 6H). |
| 108 | 521.40 | 2.10 | 1H NMR(500MHZ, DMSO-d6) 8.85(s, br, 1H), 8.10(m, 1H), 7.97(s, br, 1H), 7.42(d, 2H), 7.20(m, 2H), 7.05(m, 2H), 6.87(s, br, 1H), 5.83(s, br, 1H), 4.15(d, 4H), 3.22(s, br, 1H), 2.07(s, 3H), 1.30-1.17(m, 17H). |
| 109 | 522.40 | 2.40 | 1H NMR(500MHZ, DMSO-d6) 9.02(s, br, 1H), 8.92(s, br, 1H), 8.11(d, 1H), 7.45(d, 2H), 7.29(d, 2H), 7.05(s, 2H), 6.87(s, br, 2H) 4.16(d, 2H), 3.23(s, br, 2H), 2.08(s, 3H), 1.46(s, 10H), 1.23(s, br, 7H). |
| 110 | 520.30 | 2.51 | . |
| 111 | 506.30 | 2.41 | 1H NMR(500MHZ, DMSO-d6) 9.62(s, 1H), 9.00(s, br, 1H), 8.11(s, 1H), 7.48(dd, 4H), 7.13-6.77(m, 4H), 4.15(d, 4H), 3.22(d, br, 2H), 2.13(m, 2H), 2.08(s, 3H), 1.23(s, br, 6H), 0.93(m, 7H). |
| 112 | 465.40 | 2.40 | DMSO-d6: 9.65(s, 1H); 9.02(s, 1H); 8.35(s, 1H); 7.75(bs, 2H); 7.52(d, 2H); 7.40(d, 2H); 6.74(s, 1H); 4.60-4.00(m, 4H); 3.20(m, 2H); 2.05(s, 3H); 2.02(s, 3H); 1.15(m, 6H) |
| 113 | 563.30 | 2.10 | 1H NMR(500MHZ, DMSO-d6) 8.70(s, 1H), 8.14(d, 1H), 7.44(d, 2H), |
| | 563.20 | 2.03 | 6.99-6.79(m, 4H), 6.61(s, br, 2H), 4.20(d, br, 3H), 4.06(q, 2H), 3.49(m, 4H), 3.04(d, 2H), 2.97(m, 4H), 2.07(s, 3H), 1.20(m, 10H). |
| 114 | 537.40 | 3.40 | DMSO-d6: 9.18(s, 1H); 8.38(s, 1H); 7.76(bs, 2H); 7.55(d, 2H); 7.12(d, 2H); 6.75(m, 1H); 4.70-4.00(m, 4H); 3.18(m, 2H); 3.06(s, 3H); 2.03(s, 3H); 1.32(s, 9H); 1.15(m, 6H) |
| 115 | 523.40 | 3.10 | DMSO-d6: 9.15(s, 1H); 8.34(d, 1H); 7.72(bs, 2H); 7.52(d, 2H); 7.12(d, 2H); 6.60(m, 1H); 4.00-3.55(m, 6H); 3.45-3.35(m, 2H); 3.12(s, 3H); 1.95-1.75(m, 5H); 1.32(s, 9H) |
| 116 | 437.40 | 1.80 | DMSO-d6: 8.60(s, 1H); 8.35(s, 1H); 7.68(bs, 2H); 7.32(d, 2H); 6.70(s, 1H); 6.45(d, 2H); 5.15(bs, 1H); 4.60-4.00(m, 4H); 3.22(m, 2H); 2.62(s, 3H); 2.02(s, 3H); 1.16(m, 6H) |
| 117 | 423.40 | 1.60 | DMSO-d6: 8.56(s, 1H); 8.36(d, 1H); 7.65(bs, 2H); 7.28(d, 2H); 6.55(m, 1H); 6.45(d, 2H); 5.15(bs, 1H); 4.00-3.55(m, 6H); 3.45-3.35(m, 2H); 2.62(s, 3H); 2.00-1.75(m, 5H) |
| 118 | 523.40 | 3.20 | DMSO-d6: 9.18(s, 1H); 8.32(s, 1H); 7.78(bs, 2H); 7.58(d, 2H); 7.15(d, 2H); 6.75(m, 1H); 4.60-4.00(m, 4H); 3.88(q, 2H); 3.22(m, 2H); 3.18(s, 3H); 2.02(s, 3H); 1.55(m, 2H); 1.18(m, 6H); 0.72(m, 3H) |
| 119 | 523.40 | 3.20 | DMSO-d6: 9.18(s, 1H); 8.32(s, 1H); 7.78(bs, 2H); 7.58(d, 2H); 7.15(d, 2H); 6.75(m, 1H); 4.78(m, 1H); 4.60-4.00(m, 4H); 3.22(m, 2H); 3.18(s, 3H); 2.02(s, 3H); 1.18(m, 12H); |
| 120 | 537.40 | 3.40 | DMSO-d6: 9.18(s, 1H); 8.32(s, 1H); 7.78(bs, 2H); 7.58(d, 2H); 7.15(d, 2H); 6.75(m, 1H); 4.60-4.00(m, 4H); 3.75(d, 2H); 3.22(m, 2H); 3.18(s, 3H); 2.02(s, 3H); 1.76(m, 1H); 1.18(m, 6H); 0.75(m, 6H); |
| 121 | 571.40 | 3.60 | DMSO-d6: 9.22(s, 1H); 8.35(s, 1H); 7.78(bs, 2H); 7.65(d, 2H); 7.32(d, 2H); 7.15(d, 2H); 6.96(d, 2H); 6.72(m, 1H); 4.60-4.00(m, 4H); 3.22(m, 5H); 2.20(s, 3H); 2.02(s, 3H); 1.18(m, 6H) |
| 122 | 603.40 | 2.80 | DMSO-d6: 9.85(s, 1H); 8.35(d, 1H); 7.68(bs, 2H); 7.47(d, 2H); 6.86(d, 2H); 6.63(m, 1H); 4.00(m, 2H); 4.00-3.55(m, 6H); 3.40(m, 6H); 2.92(m, 4H); 1.90(m, 2H); 1.32(s, 9H) |
| 123 | 503.40 | 1.70 | DMSO-d6: 9.80(s, 1H); 8.35(d, 1H); 7.66(bs, 2H); 7.42(d, 2H); 6.83(d, 2H); 6.63(m, 1H); 4.00(m, 2H); 4.00-3.20(m, 8H); 2.85-2.95(m, 8H); 1.90(m, 2H); |
| 124 | 575.40 | 2.50 | DMSO-d6: 8.88(s, 1H); 8.38(d, 1H); 7.72(bs, 2H); 7.48(d, 2H); 6.96(d, 2H); 6.62(m, 1H); 4.06(q, 2H); 4.03(m, 2H); 4.00-3.60(m, 4H); 3.55-3.35(m, 8H); 2.92(m, 4H); 1.85(m, 2H); 1.15(t, 3H) |
| 125 | 589.40 | 2.70 | DMSO-d6: 8.88(s, 1H); 8.38(d, 1H); 7.72(bs, 2H); 7.48(d, 2H); 6.96(d, 2H); 6.62(m, 1H); 4.00(m, 2H); 3.96(t, 2H); 4.00-3.60(m, 4H); 3.55-3.35(m, 8H); 2.92(m, 4H); 1.85(m, 2H); 1.58(m, 2H); 0.82(t, 3H) |

TABLE 2-continued

| Cmpd # | LC/MS | RT | NMR |
|---|---|---|---|
| 126 | 481.40 | 2.60 | DMSO-d6: 9.20(s, 1H); 8.32(d, 1H); 7.75(bs, 2H); 7.52(d, 2H); 7.15(d, 2H); 6.60(d, 1H); 4.10-3.55(m, 9H); 3.40(, 2H); 3.12(s, 3H); 2.00-1.75 9m, 5H) |
| 127 | 495.40 | 2.80 | DMSO-d6: 9.20(s, 1H); 8.32(d, 1H); 7.75(bs, 2H); 7.52(d, 2H); 7.15(d, 2H); 6.60(d, 1H); 4.00(m, 2H); 4.10-3.55(m, 6H); 3.45(2H); 3.10(s, 3H); 2.00-1.75(m, 5H); 1.10(m, 3H) |
| 128 | 591.30 | 2.57 | 1H NMR(500MHZ, DMSO-d6) 9.08(s, br, 1H), 8.11(d, 1H), 7.53(d, 2H), 7.15-7.01(m, 6H), 4.14(d, 3H), 3.83(d, 2H), 3.59(s, br, 4H), 3.30(d, 2H), 3.15(s, br, 4H), 2.08(s, 3H), 1.89(m, 1H), 1.23(s, br, 6H), 0.90(m, 7H). |
| 129 | 509.40 | 3.00 | DMSO-d6: 9.20(s, 1H);, 8.32(d, 1H); 7.76(bs, 2H); 7.55(d, 2H); 7.16(d, 2H); 6.60(m, 1H); 3.98(m, 2H); 4.00-3.55(m, 6H); 3.55(m, 2H); 3.10(s, 3H); 2.00-1.75(m, 5H); 1.50(m, 2H); 0.80(m, 3H) |
| 130 | 509.40 | 3.00 | DMSO-d6: 9.20(s, 1H);, 8.32(d, 1H); 7.76(bs, 2H); 7.55(d, 2H); 7.16(d, 2H); 6.60(m, 1H); 4.72(m, 1H); 4.00-3.55(m, 6H); 3.55(m, 2H); 3.10(s, 3H); 2.00-1.75(m, 5H); 1.22(m, 6H) |
| 131 | 523.40 | 3.20 | DMSO-d6: 9.20(s, 1H);, 8.32(d, 1H); 7.76(bs, 2H); 7.55(d, 2H); 7.16(d, 2H); 6.60(m, 1H); 4.00-3.55(m, 8H); 3.55(,. 2H); 3.12(s, 3H); 2.00-1.75(m, 6H); 0.80 *m, 6H) |
| 132 | 537.40 | 3.40 | DMSO-d6: 9.20(s, 1H); 8.32(d, 1H); 7.76(bs, 2H); 7.55(d, 2H); 7.16(d, 2H); 6.60(m, 1H); 4.00-3.55(m, 8H); 3.55(m, 2H); 3.12(s, 3H); 2.00-1.75(m, 5H); 0.70(m, 9H) |
| 133 | 557.30 | 3.40 | DMSO-d6: 9.22(s, 1H); 8.32(d, 1H); 7.72(bs, 2H); 7.58(d, 2H); 7.25(d, 2H); 7.15(d, 2H); 6.98(m, 2H); 6.60(m, 1H); 4.00-3.55(m, 6H); 3.40(m, 2H);; 3.20(m, 3H); 2.20(s, 3H); 2.00-1.75(m, 5H) |
| 134 | 543.30 | 3.20 | DMSO-d6: 9.22(s, 1H); 8.40(d, 1H); 7.70(bs, 2H); 7.62(d, 2H); 7.30(m, 4H); 7.18(m, 1H); 7.10(m, 2H); 6.60(m, 1H); 4.00-3.55(m, 6H); 3.40(m, 2H); 3.28(m, 3H); 2.00-1.75(m, 5H) |
| 135 | 573.30 | 3.20 | DMSO-d6: 9.22(s, 1H); 8.34(d, 1H); 7.70(bs, 2H); 7.62(d, 2H); 7.20(m, 2H); 7.00(m, 2H); 6.90(m, 2H); 6.62(m, 1H); 4.00-3.55(m, 9H); 3.40(m, 2H); 3.25(m, 3H); 2.00-1.75(m, 5H) |
| 136 | 534.30 | 3.10 | DMSO-d6: 9.02(bs, 1H); 8.92(s, 1H); 8.40(d, 1H); 7.62(bs, 2H); 7.40(d, 2H); 7.30(d, 2H); 6.62(m, 1H); 4.10-3.55(m, 8H); 3.40(m, 2H); 1.86(m, 2H); 1.40(s, 9H) |
| 137 | 506.40 | 2.70 | DMSO-d6: 9.32(s, 1H); 8.95(s, 1H); 8.32(d, 1H); 7.75(bs, 2H); 7.42(d, 2H); 7.25(d, 2H); 6.65(m, 1H); 4.05(q, 2H); 4.00(m, 2H); 4.00-3.40(m, 8H); 1.85(m, 2H); 1.15(t, 3H) |
| 138 | 568.40 | 3.30 | DMSO-d6: 9.88(bs, 1H); 9.05(s, 1H); 8.35(d, 1H); 7.75(bs, 2H); 7.50(d, 2H); 7.32(d, 2H); 7.18(d, 2H); 7.02(d, 2H); 6.62(m, 1H); 3.98(m, 2H); 4.00-3.30(m, 8H); 2.29(s, 3H); 1.88(m, 2H); |
| 139 | 577.20 | 2.31 | 1H NMR(500MHZ, CD3OD) 8.04(d, 1H), 7.65(s, br, 2H), 7.37(m, 4H), 4.13-3.98(m, 4H), 3.82(s, br, 4H), 3.61-3.32(m, 5H), 2.65(s, 8H), 2.20(s, 3H), 1.70(m, 2H), 1.38(s, br, 4H), 0.98(t, 3H). |
| 140 | 588.20 | 2.10 | 1H NMR(500MHZ, CD3OD) 7.99(m, 1H), 7.64(s, br, 2H), 7.41-7.22(m, 4H), 4.08(t, 2H), 4.04-3.71(m, 12H), 3.66(m, 2H), 3.43(s, br, 3H), 2.65(s, 4H), 2.03(s, br, 2H), 1.69(m, 2H), 0.98(t, 3H). |
| 141 | 574.30 | 2.80 | DMSO-d6: 8.95(m, 1H); 8.05(m, 1H); 7.50(m, 2H); 7.05(m, 1H); 6.90(m, 5H); 4.00(m, 4H); 4.00-3.50(m, 4H); 3.00(m, 4H); 1.85(m, 2H); 1.22(t, 3H) |
| 142 | 605.30 | 2.00 | 1H NMR(500MHZ, DMSO-d6) 9.11(s, br, 1H), 8.11(d, 1H), 7.53(d, 2H), 7.17-6.96(m, 6H), 4.14(d, 2H), 3.75(s, 2H), 3.61(s, br, 5H), 3.31(d, 2H), 3.17(s, br, 4H), 2.08(s, 3H), 1.24(s, br, 6H), 0.93(s, 10H). |
| 143 | 577.30 | 2.22 | 1H NMR(500MHZ, DMSO-d6) 8.99(s, br, 1H), 8.11(d, 1H), 7.50(d, 2H), 7.13-6.84(m, 6H), 4.80(m, 1H), 4.14(d, 2H), 3.54(s, br, 5H), 3.25(d, br, 2H), 3.09(s, br, 4H), 2.08(s, 3H), 1.20(m, 13H). |
| 144 | 585.40 | 2.20 | DMSO-d6: 9.02(bs, 1H); 8.08(d, 1H); 7.52(d, 2H); 7.15(m, 1H); 6.98(m, 5H) 4.05(q, 2H); 3.85(m, 4H); 3.55(m, 6H); 3.35(m, 2H); 3.12(m, 4H); 2.88(s, 3H); 1.90(m, 2H); 1.15(t, 3H) |
| 145 | 599.40 | 2.30 | |
| 146 | 613.50 | 2.10 | |
| 147 | 627.50 | 2.30 | DMSO-d6: 8.95(bs, 1H); 8.06(d, 1H); 7.42(m, 2H); 7.10-6.90(m, 6H); 4.05(q, 2h); 3.82(m, 4H); 3.52(m, 6H); 3.28(m, 2H); 3.05(m, 6H); 1.88(m, 2H); 1.52(m, 2H); 1.25(m, 2H); 1.20(t, 3H); 0.80(t, 3H) |
| 148 | 565.40 | 2.30 | DMSO-d6: 8.95(bs, 1H); 8.06(d, 1H); 7.48(m, 2H); 7.10-6.90(m, 6H); 4.06(q, 2H); 3.80(m, 4H); 3.60(m, 4H); 3.55(s, 3H); 3.50(m, 4H); 3.35(m, 2H); 3.00(m, 4H); 1.80(m, 2H); 1.16(t, 3H) |
| 149 | 579.40 | 2.40 | |
| 150 | 593.50 | 2.20 | 8.95(bs, 1H); 8.02(d, 1H); 7.42(m, 2H); 7.10-6.90(m, 6h); 4.05(q, 2H); 3.80-3.40(m, 14H); 3.00(m, 4H); 1.85(m, 2H); 1.35(m, 2H); 1.20(m, 3H); 0.75(m, 3H) |
| 151 | 593.50 | 2.30 | 8.95(bs, 1H); 8.02(d, 1H); 7.42(m, 2H); 7.10-6.90(m, 6h); 4.62(m, 1H); 4.02(q, 2H); 3.80(m, 4H); 3.60-3.40(m, 8H); 3.02(m, 4H); 1.80(m, 2H); 1.20(t, 3H); 1.02(m, 6H) |
| 152 | 585.30 | 2.00 | |
| 153 | 599.30 | 2.10 | |

TABLE 2-continued

| Cmpd # | LC/MS | RT | NMR |
|---|---|---|---|
| 154 | 613.30 | 2.30 | DMS)-d6: 8.96(bs, 1H); 8.03(d, 1H); 7.42(d, 2H); 7.20-6.80(m, 6H); 3.80-3.60(m, 8H); 3.40(m, 2H); 3.35(m, 4H); 3.10(m, 6H); 1.85(m, 2H); 1.45(m, 2H); 1.22(m, 3H); 0.80(m, 3H) |
| 155 | 613.30 | 2.30 | DMS)-d6: 8.96(bs, 1H); 8.03(d, 1H); 7.42(d, 2H); 7.20-6.80(m, 6H); 4.60(m, 1H); 3.90-3.10(m, 6H); 3.32(m, 6H); 3.12(m, 6H); 1.80(m, 2H); 1.22(m, 3H); 1.06(m, 6H) |
| 156 | 579.20 | 1.70 | 1H NMR(500MHZ, CD3OD) 7.98(m, 1H), 7.69(s, br, 2H), 7.51-7.33(m, 3H), 7.28(s, br, 1H), 4.94(m, 1H), 3.97-3.78(m, 10H), 3.63(s, br, 3H), 3.60-3.42(m, 6H), 1.96(s, br, 2H), 1.30(d, 6H). |
| 157 | 593.20 | 1.80 | 1H NMR(500MHZ, CD3OD) 7.99(m, 1H), 7.69(s, br, 2H), 7.51-7.34(m, 3H), 7.28(s, br, 1H), 4.93(m, 1H), 4.11-3.98(m, 2H), 3.98-3.77(m, 10H), 3.63-3.37(m, 6H), 1.97(s, br, 2H), 1.28(d, 6H), 1.15(m, 3H). |
| 158 | 579.20 | 1.70 | 1H NMR(500MHZ, DMSO-d6) 9.04(s, br, 1H), 8.07(d, 1H), 7.50(d, 2H), 7.18-6.96(m, 6H), 3.99(t, 2H), 3.87-3.76(m, 4H), 3.65(m, 2H), 3.60-3.49(m, 8H), 3.41(s, br, 2H), 3.08(s, br, 3H), 1.85(m, 2H), 1.59(m, 2H), 0.91(t, 3H). |
| 159 | 593.20 | 1.80 | 1H NMR(500MHZ, DMSO-d6) 9.01(s, br, 1H), 8.06(d, 1H), 7.49(d, 2H), 7.16-6.92(m, 6H), 3.99(t, 2H), 3.87-3.77(m, 4H), 3.65(s, br, 2H), 3.54(s, br, 5H), 3.41(s, br, 2H), 3.06(s, br, 4H), 1.84(s, br, 2H), 1.59(m, 2H), 1.07(m, 4H), 0.91(t, 3H). |
| 160 | 607.20 | 1.90 | |
| 161 | 607.20 | 1.90 | |
| 162 | 599.20 | 1.70 | 1H NMR(500MHZ, DMSO-d6) 9.03(s, br, 1H), 8.08(d, 1H), 7.50(d, 2H), 7.20-6.89(m, 6H), 4.00(t, 2H), 3.92-3.80(m, 4H), 3.55(m, 8H), 3.09(s, br, 4H), 2.90(s, 3H), 1.92(m, 2H), 1.60(m, 2H), 0.90(t, 3H). |
| 163 | 613.20 | 1.70 | |
| 164 | 627.20 | 1.90 | |
| 165 | 627.20 | 1.80 | |
| 166 | 548.30 | 2.00 | DMSO-d6: 9.60(bs, 1H); 8.95(bs, 1H); 8.40(s, 1H); 7.50(d, 2H); 6.92(d, 2H); 6.72(s, 1H); 4.10-3.90(m, 6H); 3.75(m, 3H); 3.50(m, 4H); 3.00(m, 4H); 2.82(d, 3h); 2.38(m, 2H); 2.15(m, 1H); 1.88(m, 2H); 1.15(t, 3h) |
| 167 | 439.30 | 2.10 | DMSO-d6: 8.99(bs, 1H); 8.32(bs, 1H); 7.75(bs, 2H); 7.50(m, 2H);; 7.05(m, 2H); 6.60(m, 1H); 4.06(q, 2H); 3.55(m, 4H); 3.10(m, 4H); 2.80(s, 3H); 1.22(t, 3H) |
| 168 | 599.10 | 1.60 | 1H NMR(500MHZ, CD3OD) 7.98(d, 1H), 7.64(d, 2H), 7.40-7.27(m, 4H), 4.99(m, 1H), 3.97(s, br, 3H), 3.79(s, br, 3H), 3.70(t, 2H), 3.53-3.37(m, 6H), 2.99(s, 1H), 2.92(s, 2H), 2.86(s, 1H), 2.82(s, 1H), 2.35(t, 1H), 2.04(m, 2H), 1.28(m, 5H). |
| 169 | 613.20 | 1.70 | 1H NMR(500MHZ, CD3OD) 7.99(d, 1H), 7.65(d, 2H), 7.39-7.25(m, 4H), 4.93(m, 1H), 3.93(m, 4H), 3.80(m, 4H), 3.73(t, 2H), 3.53-3.39(m, 6H), 3.11(m, 2H), 2.03(m, 2H), 1.28(m, 9H). |
| 170 | 465.90 | 2.39 | DMSO-d6: 9.30(bs, 1H); 9.02(m, 1H); 8.03(m, 1H); 7.42(d, 2H); 7.28(d, 2H); 7.10-6.90(m, 3h); 3.80-3.60(m, 6H); 3.60(s, 3h); 3.50-3.40(m, 2h); 1.95(m, 3H); 1.85(m, 2H) |
| 171 | 479.90 | 2.67 | DMSO-d6: 9.30(bs, 1H); 9.02(m, 1H); 8.03(m, 1H); 7.42(d, 2H); 7.28(d, 2H); 7.10-6.90(m, 3H); 4.04(q, 2H); 3.80(m, 6H); 3.50-3.40(m, 2H); 1.95(m, 3H); 1.85(m, 2H); 1.22(t, 3H) |
| 172 | 493.90 | 3.03 | DMSO-d6: 9.30(bs, 1H); 9.02(m, 1H); 8.03(m, 1H); 7.42(d, 2H); 7.28(d, 2H); 7.10-6.90(m, 3H); 3.98(t, 2H); 3.90-3.60(m, 6H); 3.50-3.40(m, 2H); 1.95(m, 3H); 1.85(m, 2H); 1.60(m, 2H); 0.90(t, 3H) |
| 173 | 493.90 | 2.97 | DMSO-d6: 9.30(bs, 1H); 9.02(m, 1H); 8.03(m, 1H); 7.42(d, 2H); 7.28(d, 2H); 7.10-6.90(m, 3H); 4.82(m, 1H); 3.90-3.60(m, 6H); 3.50-3.40(m, 2H); 1.95(m, 3H); 1.85(m, 2H); 1.22(d, 6H) |
| 174 | 507.90 | 3.40 | DMSO-d6: 9.30(bs, 1H); 9.02(m, 1H); 8.03(m, 1H); 7.42(d, 2H); 7.28(d, 2H); 7.10-6.90(m, 3H); 4.02(t, 2H); 3.90-3.60(m, 6H); 3.50-3.40(m, 2H); 1.95(m, 3H); 1.85(m, 2H); 1.60(m, 2h0; 1.36 9m, 2H); 0.90(t, 3H) |
| 175 | 507.90 | 3.38 | DMSO-d6: 9.30(bs, 1H); 9.02(m, 1H); 8.03(m, 1H); 7.42(d, 2H); 7.28(d, 2H); 7.10-6.90(m, 3H); 3.90-3.60(m, 6H); 3.80(d, 2H); 3.50-3.40(m, 2H); 1.95(m, 3H); 1.85(m, 3H); 0.89(d, 6H) |
| 176 | 522.00 | 3.70 | DMSO-d6: 9.30(bs, 1H); 9.02(m, 1H); 8.03(m, 1H); 7.42(d, 2H); 7.28(d, 2H); 7.10-6.90(m, 3H); 4.00-3.30(m, 10H); 1.95-1.85(m, 5H); 0.88(s, 9H) |

Example 22

Inhibition of FLT-3

Compounds were screened for their ability to inhibit FLT-3 activity using a radiometric filter-binding assay. This assay monitors the $^{33}$P incorporation into a substrate poly (Glu, Tyr) 4:1 (pE4Y). Reactions were carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay were 90 µM ATP and 0.5 mg/mL pE4Y (both from Sigma Chemicals, St Louis, Mo.). The final concentration of compounds is generally between 0.01 and 5 µM. Typically, a 12-point titration was conducted by preparing serial dilutions from 10 mM DMSO stock of test compound. Reactions were carried out at room temperature. Solution 1 contains 100 mM HEPES (pH 7.5), 10 mM $MgCl_2$, 25 mM NaCl, 1 mg/ml pE4Y and 180 μM ATP(containing 0.3 μCi of [γ-$^{33}$P]ATP for each reaction). Solution 2 contains 100 mM HEPES (pH 7.5), 10 mM MgCl$_2$, 25 mM NaCl, 2 mM DTT, 0.02% BSA and 3 nM FLT-3. The assay was run on a 96 well plate by mixing 50 μL each of Solution 1 and 2.5 mL of the test ds. The reaction was initiated with Solution 2. After incubation for 20 minutes temperature, the reaction was stopped with 50 μL of 20% TCA containing 0.4 mM of ATP. All of the reaction volume was then transferred to a filter plate and washed with 5% TCA by a Harvester9600 from TOMTEC (Hamden, Conn.). The amount of $^{33}$P incorporation into pE4y was analyzed by a Packard TopCount Microplate Scintillation Counter (Meriden, Conn.). The data was fitted using Prism software to get an IC$_{50}$ or K$_i$.

Many compounds of the invention, including compounds in Table 1, inhibited FLT-3.

Example 23

Inhibition of AUR-2

Compounds are screened in the following manner for their ability to inhibit Aurora-2 using a standard coupled enzyme assay (Fox et al (1998) *Protein Sci* 7, 2249). To an assay stock buffer solution containing 0.1M HEPES 7.5, 10 mM MgCl$_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 μM peptide (LRRASLG, American Peptide, Sunnyvale, Calif.) is added a DMSO solution of a compound of the present invention to a final concentration of 30 μM. The resulting mixture is incubated at 30° C. for 10 min. The reaction was initiated by the addition of 10 μL of Aurora-2 stock solution to give a final concentration of 70 nM in the assay. The rates of reaction are obtained by monitoring absorbance at 340 nm over a 5 minute read time at 30° C. using a BioRad Ultramark plate reader (Hercules, Calif.). The K$_i$ values are determined from the rate data as a function of inhibitor concentration.

Many compounds of the invention, including compounds in Table 1, inhibited AUR-2 with a K$_i$ of less than 50 nM.

Example 24

Inhibition of KDR

Compounds were screened for their ability to inhibit KDR using a standard coupled enzyme assay (Fox et al., Protein Sci., (1998) 7, 2249). Assays were carried out in a mixture of 200 mM HEPES 7.5, 10 mM MgCl2, 25 mM NaCl, 1 mM DTT and 1.5% DMSO. Final substrate concentrations in the assay were 300 μM ATP (Sigma Chemicals) and 10 μM poly E4Y (Sigma). Assays were carried out at 37° C. and 30 nM KDR. Final concentrations of the components of the coupled enzyme system were 2.5 mM phosphoenolpyruvate, 200 μM NADH, 30 μg/ML pyruvate kinase and 10 μg/ml lactate dehydrogenase. An assay stock buffer solution was prepared containing all of the reagents listed above, with the exception of ATP and the test compound of interest. 177 μl of the stock solution was placed in a 96 well plate followed by addition of 3 μl of 2 mM DMSO stock containing the test compound (final compound concentration 30 μM). The plate was preincubated for about 10 minutes at 37° C. and the reaction initiated by addition of 20 μl of ATP (final concentration 300 μM). Rates of reaction were obtained using a Molecular Devices plate reader (Sunnyvale, Calif.) over a 5 minute read time at 37° C. Compounds showing greater than 50% inhibition versus standard wells containing the assay mixture and DMSO without test compound were titrated to determine IC50 values determined.

Some compounds of the invention, including compounds in Table 1, inhibited KDR with a K$_i$ of less than 50 nM.

Example 25

JAK3 Inhibition Assay

Compounds were screened for their ability to inhibit JAK using the assay shown below. Reactions were carried out in a kinase buffer containing 100 mM HEPES (pH 7.4), 1 mM DTT, 10 mM MgCl$_2$, 25 mM NaCl, and 0.01% BSA.

Substrate concentrations in the assay were 5 μM ATP (200 uCi/μmole ATP) and 1 μM poly(Glu)$_4$Tyr. Reactions were carried out at 25° C. and 1 nM JAK3.

To each well of a 96 well polycarbonate plate was added 1.5 μl of a candidate JAK3 inhibitor along with 50 μl of kinase buffer containing 2 μM poly(Glu)$_4$Tyr and 10 μM ATP. This was then mixed and 50 μl of kinase buffer containing 2 nM JAK3 enzyme was added to start the reaction. After 20 minutes at room temperature (25° C.), the reaction was stopped with 50 μl of 20% trichloroacetic acid (TCA) that also contained 0.4 mM ATP. The entire contents of each well were then transferred to a 96 well glass fiber filter plate using a TomTek Cell Harvester. After washing, 60 μl of scintillation fluid was added and $^{33}$P incorporation detected on a Perkin Elmer TopCount.

Example 26

JAK2 Inhibition Assay

The assays were as described above in Example 25 except that JAK-2 enzyme was used, the final poly(Glu)$_4$Tyr concentration was 15 μM, and final ATP concentration was 12 μM.

Table 3 depicts JAK2 and JAK3 inhibition data (Ki) for exemplary compounds. Compound numbers in Table 3 corresponds to those compounds depicted in Table 1. In Table 3, "A" represents a Ki of less than 0.05 μM and "B" represents a Ki of between 0.05 and 0.5 μM for the indicated enzyme.

TABLE 3

| Cmpd # | JAK2 | JAK3 |
|---|---|---|
| 1 | B | A |
| 2 | A | A |
| 3 | A | A |
| 4 | A | A |
| 5 | A | A |
| 6 | A | A |
| 7 | A | A |
| 8 | A | A |
| 9 | A | A |
| 10 | A | A |
| 11 | A | A |
| 12 | A | A |
| 13 | A | A |
| 14 | B | B |
| 15 | A | A |
| 16 | A | A |
| 17 | A | A |
| 18 | A | A |
| 19 | A | A |
| 20 | A | A |
| 21 | A | A |
| 22 | A | A |

TABLE 3-continued

| Cmpd # | JAK2 | JAK3 |
|---|---|---|
| 23 | A | A |
| 24 | A | A |
| 25 | B | B |
| 26 | A | A |
| 27 | A | A |
| 28 | A | A |
| 29 | A | A |
| 30 | A | A |
| 31 | A | A |
| 32 | A | A |
| 33 | A | A |
| 34 | A | A |
| 35 | A | A |
| 36 | A | A |
| 37 | A | A |
| 38 | A | A |
| 39 | A | A |
| 40 | A | A |
| 41 | A | A |
| 42 | A | A |
| 43 | A | A |
| 44 | A | A |
| 45 | A | A |
| 46 | A | A |
| 47 | A | A |
| 48 | A | A |
| 49 | A | A |
| 50 | A | A |
| 51 | A | A |
| 52 | A | A |
| 53 | A | A |
| 54 | A | A |
| 55 | A | A |
| 56 | A | A |
| 57 | A | A |
| 58 | A | A |
| 59 | A | A |
| 60 | A | A |
| 61 | A | A |
| 62 | A | A |
| 63 | A | A |
| 64 | A | A |
| 65 | A | A |
| 66 | A | A |
| 67 | A | A |
| 68 | A | A |
| 69 | A | A |
| 70 | A | A |
| 71 | A | A |
| 72 | A | A |
| 73 | A | A |
| 74 | A | A |
| 75 | A | A |
| 76 | A | A |
| 77 | A | A |
| 78 | A | A |
| 79 | A | A |
| 80 | A | A |
| 81 | A | A |
| 82 | A | B |
| 83 | A | N |
| 84 | A | A |
| 85 | A | A |
| 86 | A | A |
| 87 | A | A |
| 88 | A | A |
| 89 | A | A |
| 90 | A | A |
| 91 | A | A |
| 92 | A | A |
| 93 | A | A |
| 94 | A | A |
| 95 | A | A |
| 96 | A | A |
| 97 | B | B |
| 98 | B | B |
| 99 | A | A |
| 100 | A | A |
| 101 | A | A |
| 102 | A | A |
| 103 | A | A |
| 104 | A | A |
| 105 | A | A |
| 106 | A | A |
| 107 | A | A |
| 108 | A | A |
| 109 | A | A |
| 110 | A | A |
| 111 | A | A |
| 112 | A | A |
| 113 | A | A |
| 114 | A | A |
| 115 | A | A |
| 116 | A | A |
| 117 | A | A |
| 118 | A | A |
| 119 | A | A |
| 120 | A | A |
| 121 | A | A |
| 122 | A | A |
| 123 | A | A |
| 124 | A | A |
| 125 | A | A |
| 126 | A | A |
| 127 | A | A |
| 128 | A | A |
| 129 | A | A |
| 130 | A | A |
| 131 | A | A |
| 132 | A | A |
| 133 | A | A |
| 134 | A | A |
| 135 | A | A |
| 136 | A | A |
| 137 | A | A |
| 138 | A | A |
| 139 | A | A |
| 140 | A | A |
| 141 | | |
| 142 | A | A |
| 143 | A | A |
| 144 | B | B |
| 145 | B | B |
| 146 | B | B |
| 147 | B | B |
| 148 | B | B |
| 149 | B | B |
| 150 | B | B |
| 151 | B | B |
| 152 | B | B |
| 153 | B | B |
| 154 | B | B |
| 155 | B | B |
| 156 | B | B |
| 157 | B | B |
| 158 | B | B |
| 159 | B | B |
| 160 | B | B |
| 161 | B | B |
| 162 | B | B |
| 163 | B | B |
| 164 | B | B |
| 165 | B | B |
| 166 | A | A |
| 167 | A | A |
| 168 | B | B |
| 169 | B | B |
| 170 | B | B |
| 171 | B | A |
| 172 | B | A |
| 173 | B | A |
| 174 | B | B |
| 175 | B | B |

TABLE 3-continued

| Cmpd # | JAK2 | JAK3 |
|---|---|---|
| 176 | B | B |
| 119 | A | A |

While a number of embodiments of this invention have been described, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above.

The invention claimed is:

1. A compound of formula I:

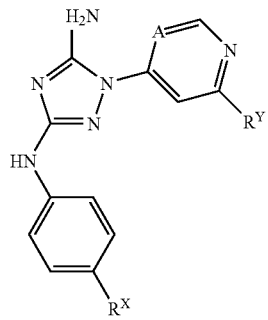

(I)

or a pharmaceutically acceptable salt thereof, wherein:
A is N;
$R^1$ is H, halogen or a $C_{1-6}$ alkyl;
$R^X$ is selected from

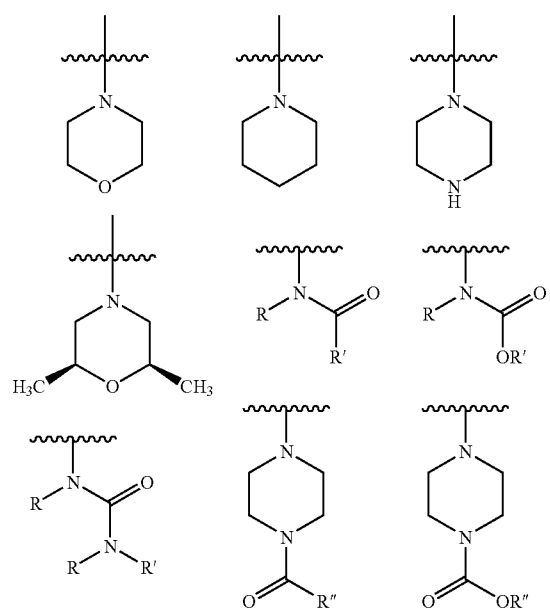

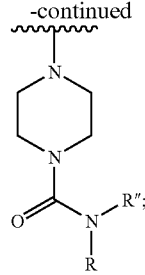

$R^Y$ is selected from

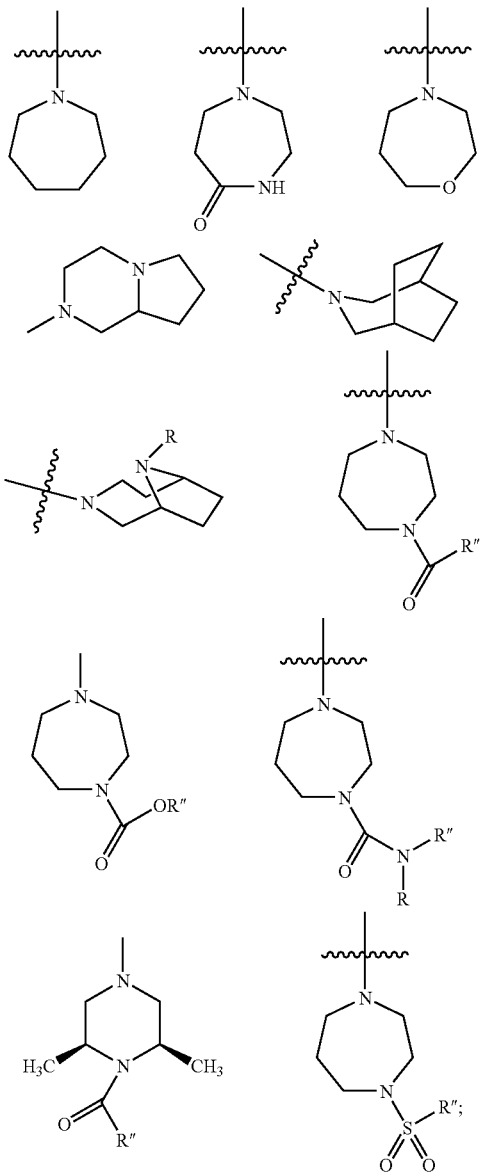

each occurrence of R is independently selected from hydrogen or a $C_{1-6}$ aliphatic group optionally substituted with J or J'; and
R' is independently selected from hydrogen or a group selected from $C_{1-8}$ aliphatic optionally substituted with up to three occurrences of J or J', $C_{6-10}$ aryl optionally substituted with up to three occurrences of J, a heteroaryl ring having 5-10 ring atoms optionally substituted with up to three occurrences of J, or a heterocyclyl ring having 3-10 ring atoms optionally substituted with up to three occurrences of J or J', or wherein R and R' taken together, form a 5-8 membered cycloalkyl, heterocyclyl, aryl, or heteroaryl ring having 0-3 heteroatoms independently selected from nitrogen, oxygen, or sulfur, each ring being optionally and independently substituted with up to three occurrences of J;

each occurrence of R" is independently selected from hydrogen or a group selected from $C_{1-8}$ aliphatic optionally substituted with up to three occurrences of J or J', $C_{6-10}$ aryl optionally substituted with up to three occurrences of J, a heteroaryl ring having 5-10 ring atoms optionally substituted with up to three occurrences of J, or a heterocyclyl ring having 3-10 ring atoms optionally substituted with up to three occurrences of J or J', or wherein R and R" taken together, form a 5-8 membered cycloalkyl, heterocyclyl, aryl, or heteroaryl ring having 0-3 heteroatoms independently selected from nitrogen, oxygen, or sulfur, each ring being optionally and independently substituted with up to three occurrences of J;

each occurrence of J is independently selected from halogen; —$R^o$; —$OR^o$; —$SR^o$; 1,2-methylenedioxy; 1,2-ethylenedioxy; phenyl (Ph) optionally substituted with $R^o$; —O(Ph) optionally substituted with $R^o$; —$(CH_2)_{1-2}$(Ph) optionally substituted with $R^o$; —CH=CH(Ph) optionally substituted with $R^o$; —$NO_2$; —CN; —$N(R^o)_2$; —$NR^oC(O)R^o$; —$NR^oC(S)R^o$; —$NR^oC(O)N(R^o)_2$; —$NR^oC(S)N(R^o)_2$; —$NR^oCO_2R^o$; —$NR^oNR^oC(O)R^o$; —$NR^oNR^oC(O)N(R^o)_2$; —$NR^oNR^oCO_2R^o$; —C(O)C(O)$R^o$; —C(O)C(O)$OR^o$, —C(O)C(O)N($R^o$)$_2$, —C(O)$CH_2$C(O)$R^o$; —$CO_2R^o$; —C(O)$R^o$; —C(S)$R^o$; —C(S)$OR^o$, —C(O)N($R^o$)$_2$; —C(S)N($R^o$)$_2$; —C(=NH)—N($R^o$)$_2$, —OC(O)N($R^o$)$_2$; —OC(O)$R^o$; —C(O)N(O$R^o$)$R^o$; —C(N$OR^o$)$R^o$; —S(O)$_2R^o$; —S(O)$_3R^o$; —$SO_2$N($R^o$)$_2$; —S(O)$R^o$; —$NR^oSO_2$N($R^o$)$_2$; —$NR^oSO_2R^o$; —N(O$R^o$)$R^o$; —C(=NH)—N($R^o$)$_2$; C(=NO$R^o$)$R^o$; $(CH_2)_{0-2}$NHC(O)$R^o$; —P(O)$_2R^o$; —PO($R^o$)$_2$; —OPO($R^o$)$_2$; or —P(O)(H)(O$R^o$);

wherein each independent occurrence of $R^o$ is selected from hydrogen, optionally substituted $C_{1-6}$ aliphatic, optionally substituted 5-6 membered heteroaryl or heterocyclic ring, optionally substituted phenyl (Ph); optionally substituted —O(Ph); optionally substituted —$(CH_2)_{1-2}$(Ph); optionally substituted —CH=CH(Ph); or, two independent occurrences of $R^o$, on the same substituent or different substituents, taken together with the atom(s) to which each $R^o$ group is bound, form a 5-8-membered heterocyclyl, aryl, or heteroaryl ring or a 3-8-membered cycloalkyl ring having 0-3 heteroatoms independently selected from nitrogen, oxygen, or sulfur;

wherein a substituent for an aliphatic group of $R^o$ is optionally substituted heteroaryl, optionally substituted, heterocyclic, $NH_2$, NH($C_{1-6}$ aliphatic), N($C_{1-6}$ aliphatic)$_2$, halogen, $C_{1-6}$ aliphatic, OH, O($C_{1-6}$ aliphatic), $NO_2$, CN, $CO_2$H, $CO_2$($C_{1-6}$ aliphatic), O(halo $C_{1-6}$ aliphatic), or halo($C_{1-6}$ aliphatic), wherein each of these $C_{1-6}$ aliphatic groups of $R^o$ is unsubstituted;

wherein a substituent for a phenyl, heteroaryl or heterocyclic group of $R^o$ is $C_{1-6}$ aliphatic, $NH_2$, NH($C_{1-4}$ aliphatic), N($C_{1-6}$ aliphatic)$_2$, halogen, $C_{1-6}$ aliphatic, OH, O($C_{1-6}$ aliphatic), $NO_2$, CN, $CO_2$H, $CO_2$($C_{1-6}$ aliphatic), O(halo $C_{1-6}$ aliphatic), or halo($C_{1-6}$ aliphatic), wherein each of these $C_{1-6}$ aliphatic groups of $R^o$ is unsubstituted;

each occurrence of J' is independently selected from =O, =S, =NNH$R^*$, =NN($R^*$)$_2$, =NNHC(O)$R^*$, =NNHCO$_2$(alkyl), =NNHSO$_2$(alkyl), or =N$R^*$, where each $R^*$ is independently selected from hydrogen or an optionally substituted $C_{1-6}$ aliphatic; wherein an aliphatic group of $R^*$ is optionally substituted with $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2$H, $CO_2$($C_{1-4}$ aliphatic), O(halo $C_{1-4}$ aliphatic), or halo ($C_{1-4}$ aliphatic), wherein each of the $C_{1-4}$ aliphatic groups of $R^*$ is unsubstituted.

2. The compound according to claim 1, wherein $R^X$ is selected from

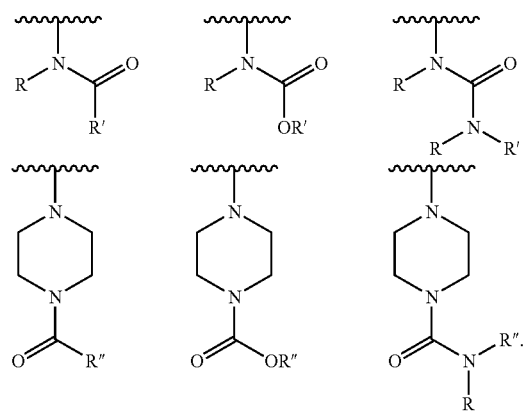

3. The compound according to claim 1, wherein $R_Y$ is

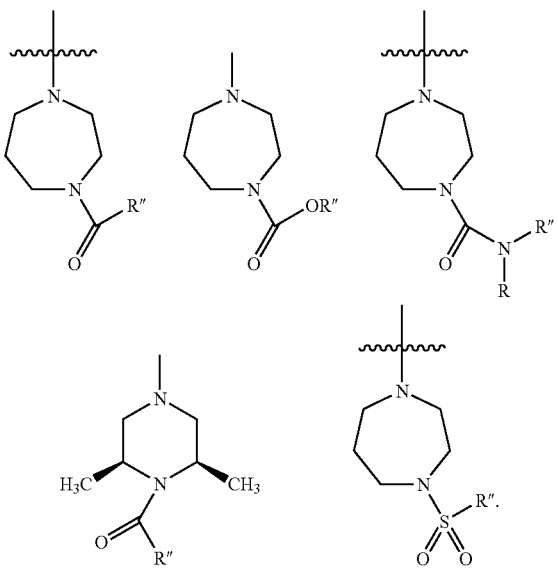

4. The compound according to claim 1, wherein R' is a $C_{1-6}$ aliphatic, phenyl or a 5-8 membered heteroaryl group, wherein R' is optionally substituted with up to one occurrence of J.

5. The compound according to claim 4, wherein R' is a $C_{1-6}$ aliphatic group or phenyl, wherein R' is optionally substituted with up to one occurrence of J, wherein J is —COOR°, —OR°, R° or —CF₃, and wherein R° is a C₁₋₃ aliphatic group.

6. The compound according to claim 5, wherein R' is methyl, ethyl, propyl, isopropyl, —CH₂-isopropyl, butyl, t-butyl, —CH₂-t-butyl or cyclohexyl, wherein R' is optionally substituted with —COOR°, —OR° or R°.

7. The compound according to claim 1, wherein R is hydrogen or methyl.

8. The compound according to claim 1, wherein each R" is independently selected from a C₁₋₆ aliphatic group, phenyl or a 5-8 membered heterocycle group, wherein each R" is optionally and independently substituted with up to one occurrence of J.

9. The compound according to claim 8, wherein each R" is independently selected from a C₁₋₆ aliphatic group or phenyl, wherein each R" is optionally and substituted with up to one occurrence of J, wherein each J is independently selected from halogen, —CF₃, —CN, —COOR°, —COR° or —OR°, wherein each R° is a C₁₋₃ aliphatic group.

10. The compound according to claim 9, wherein each R" is methyl, ethyl, propyl, isopropyl, —CH₂-isopropyl, butyl, t-butyl or —CH₂-t-butyl, wherein each R" is optionally substituted with —CN, —COOR° or —OR°.

11. A compound according to claim 1, selected from one of the following compounds:

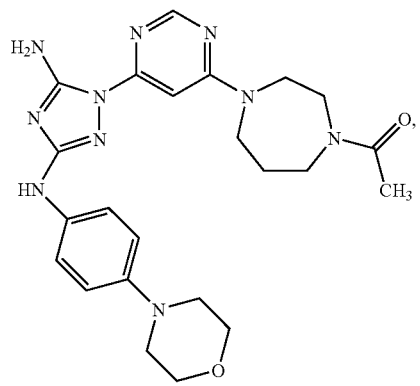

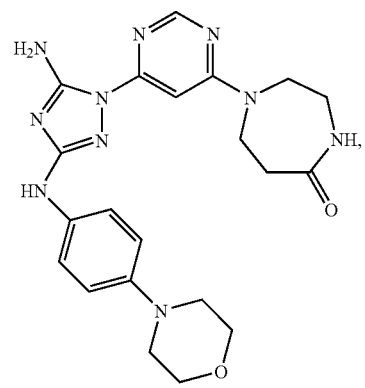

-continued

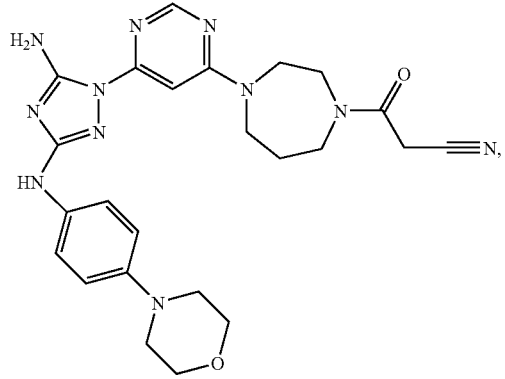

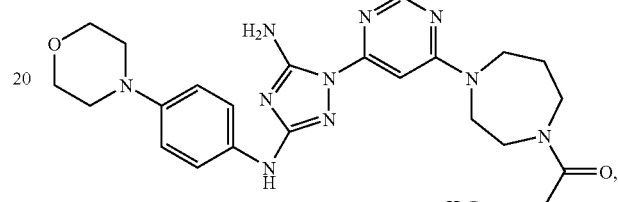

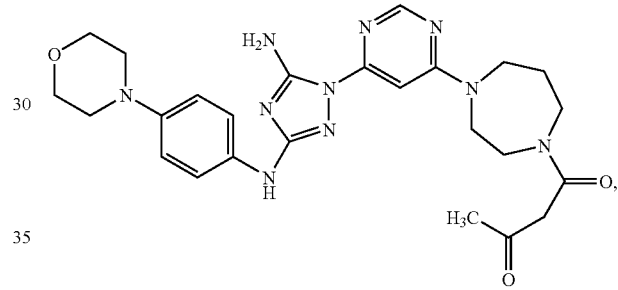

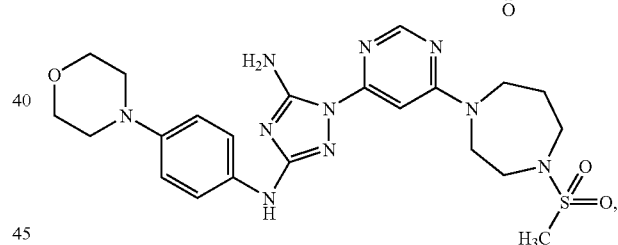

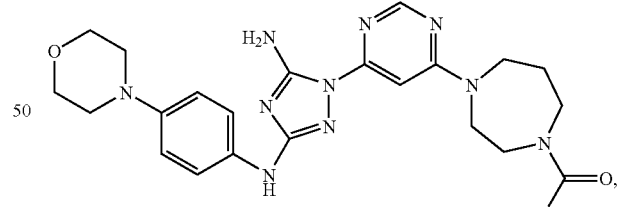

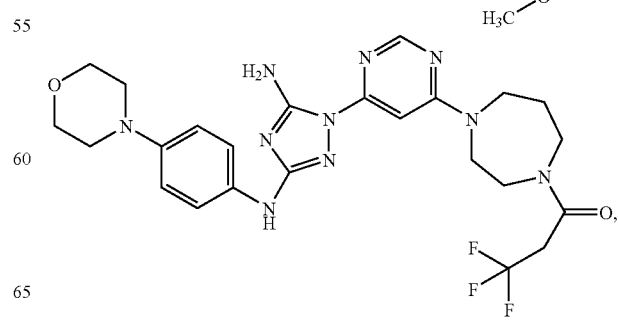

-continued
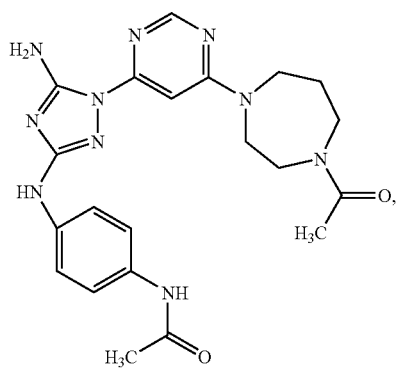
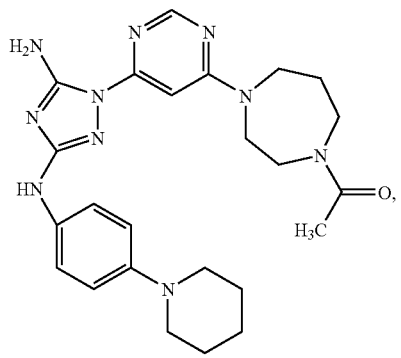
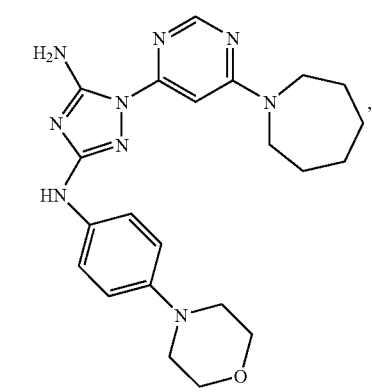
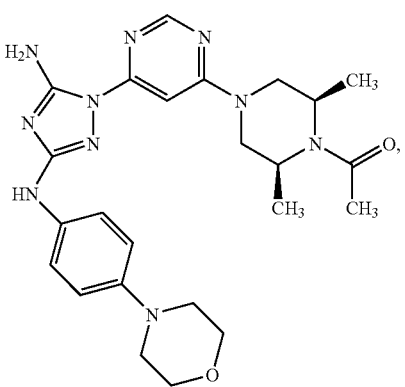
-continued
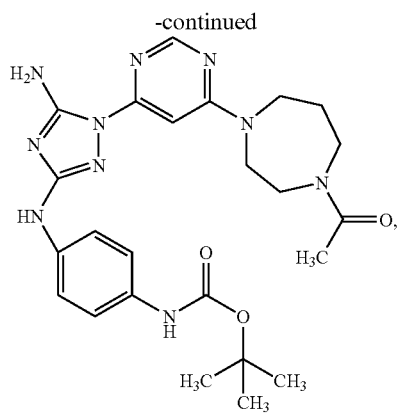
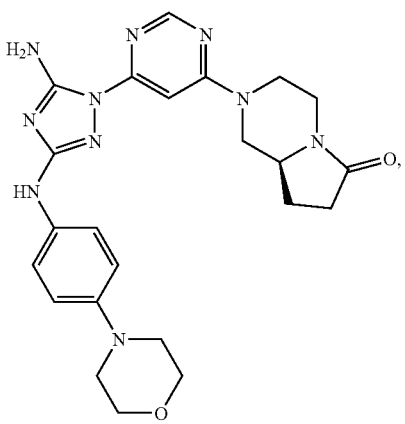
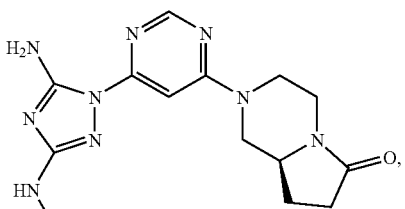
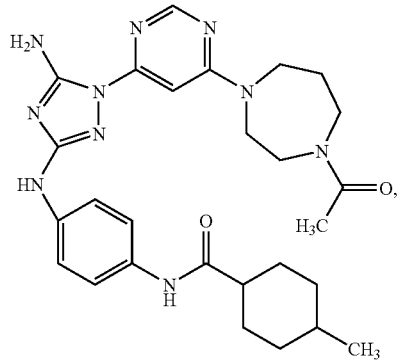

-continued
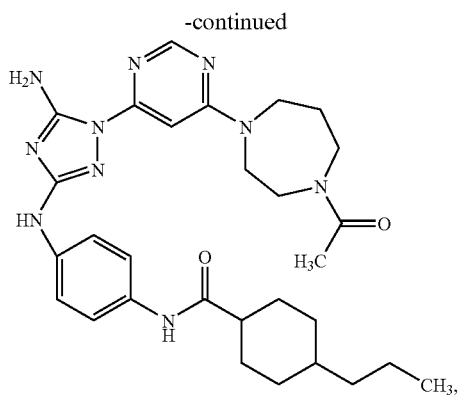
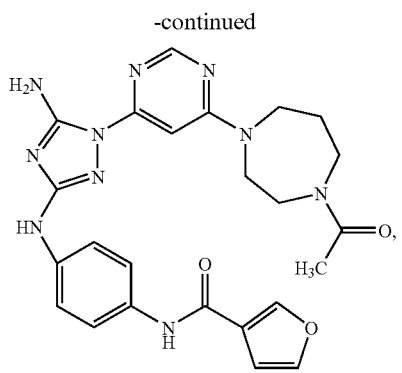
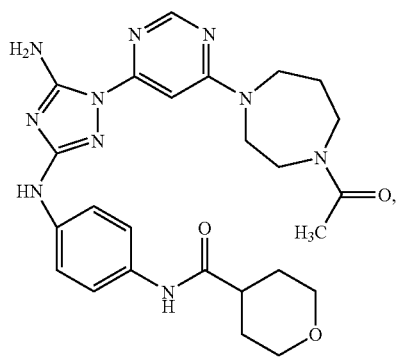
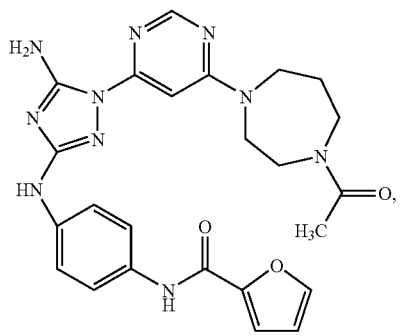
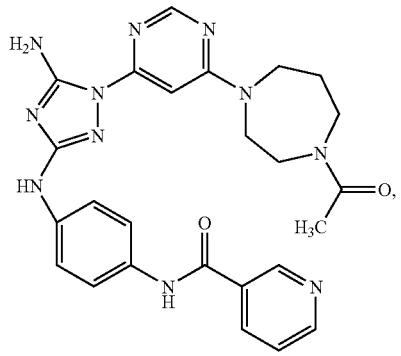
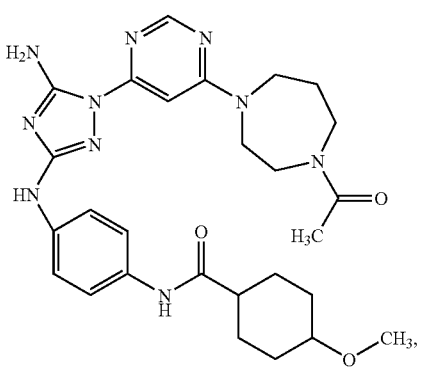
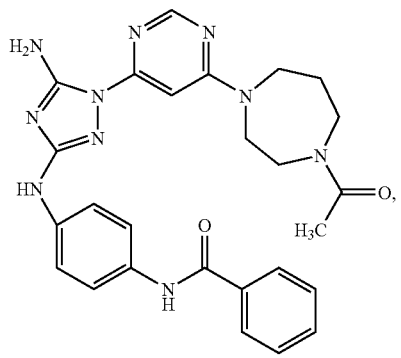
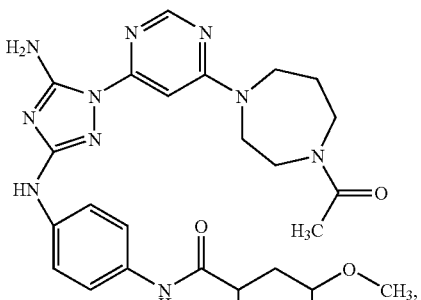

-continued
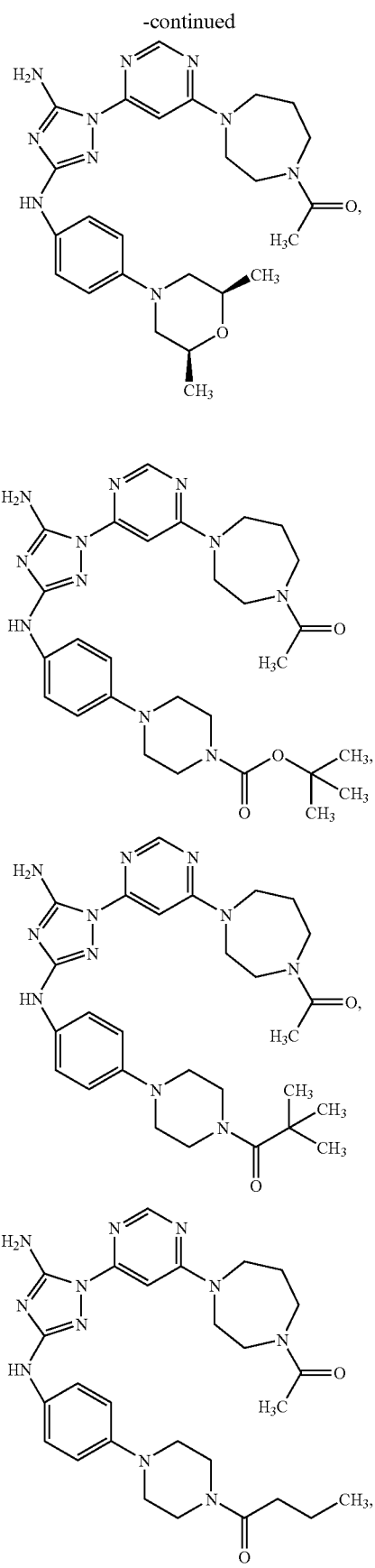
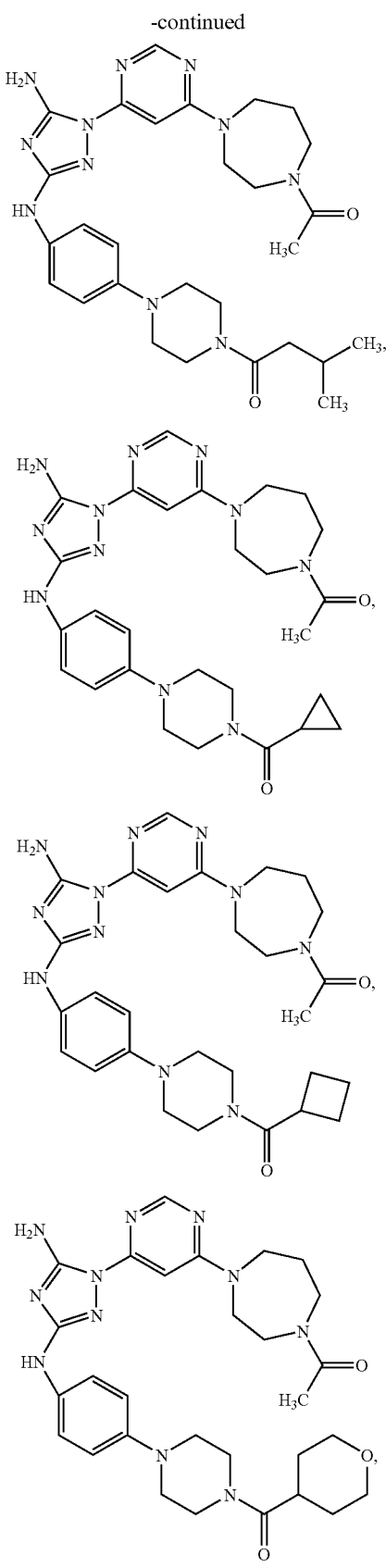

-continued
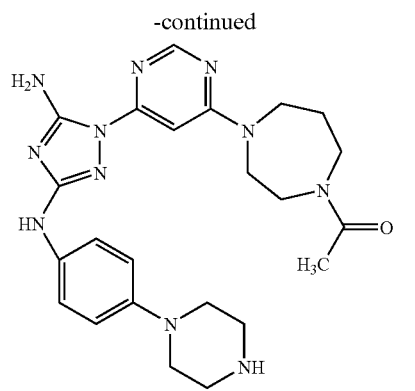
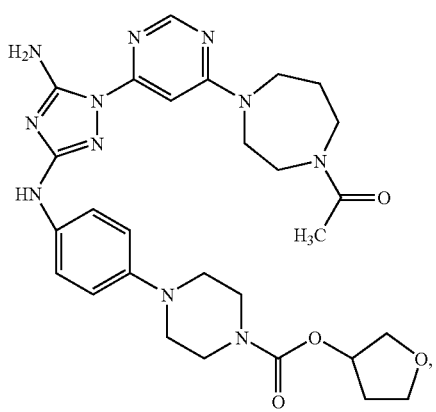
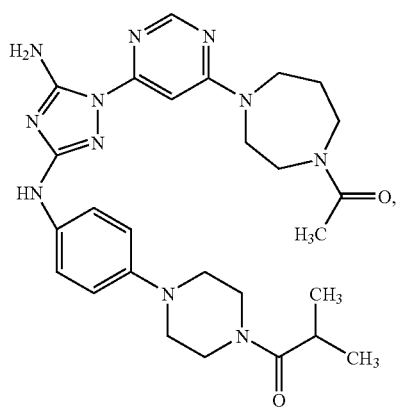
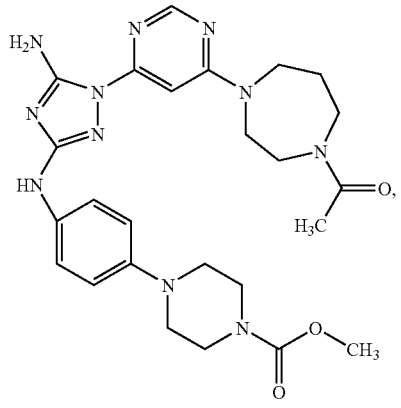
-continued
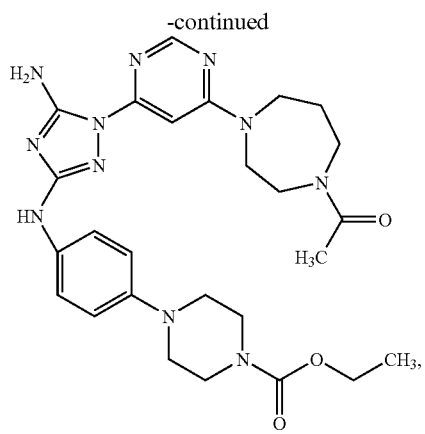
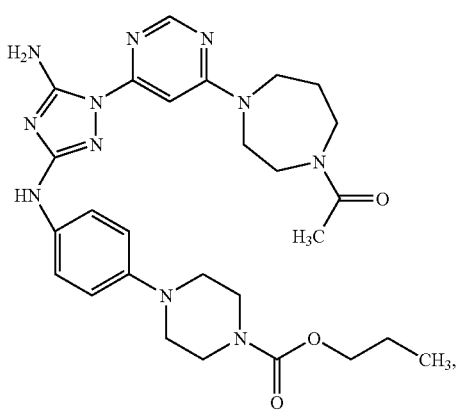
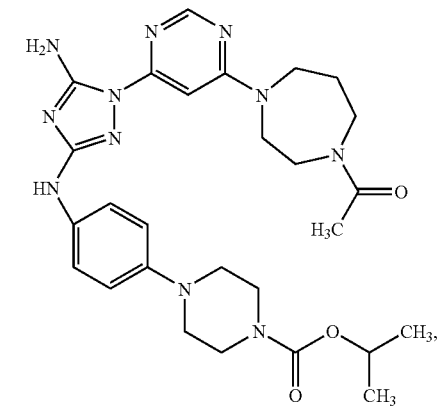
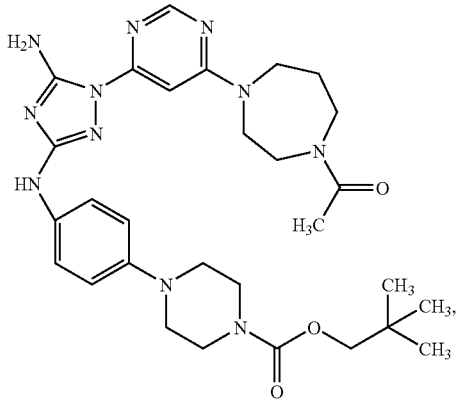

185
-continued
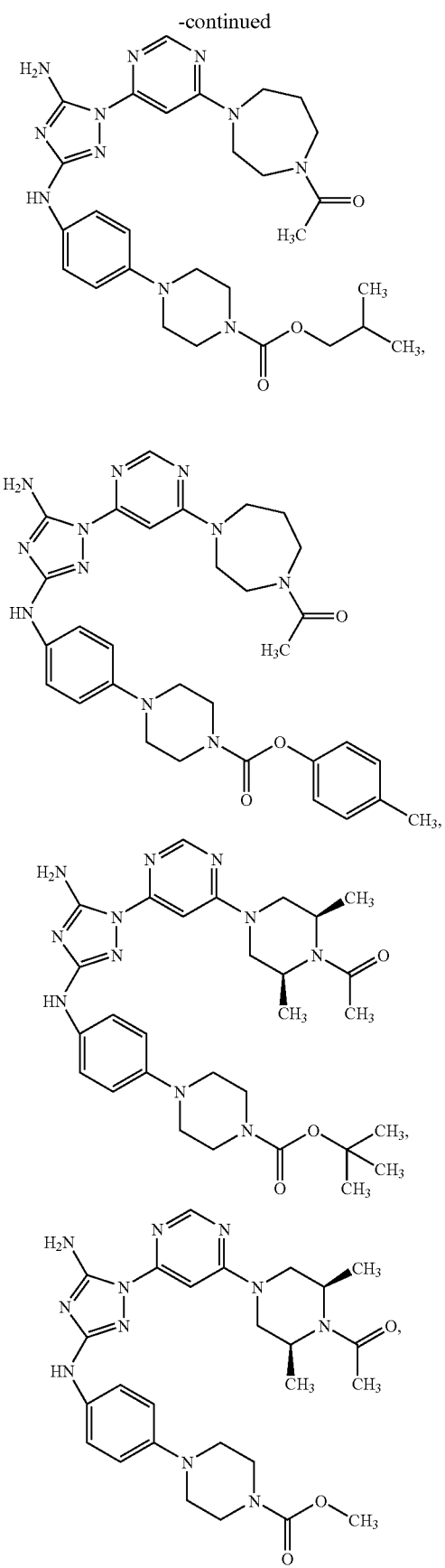
186
-continued
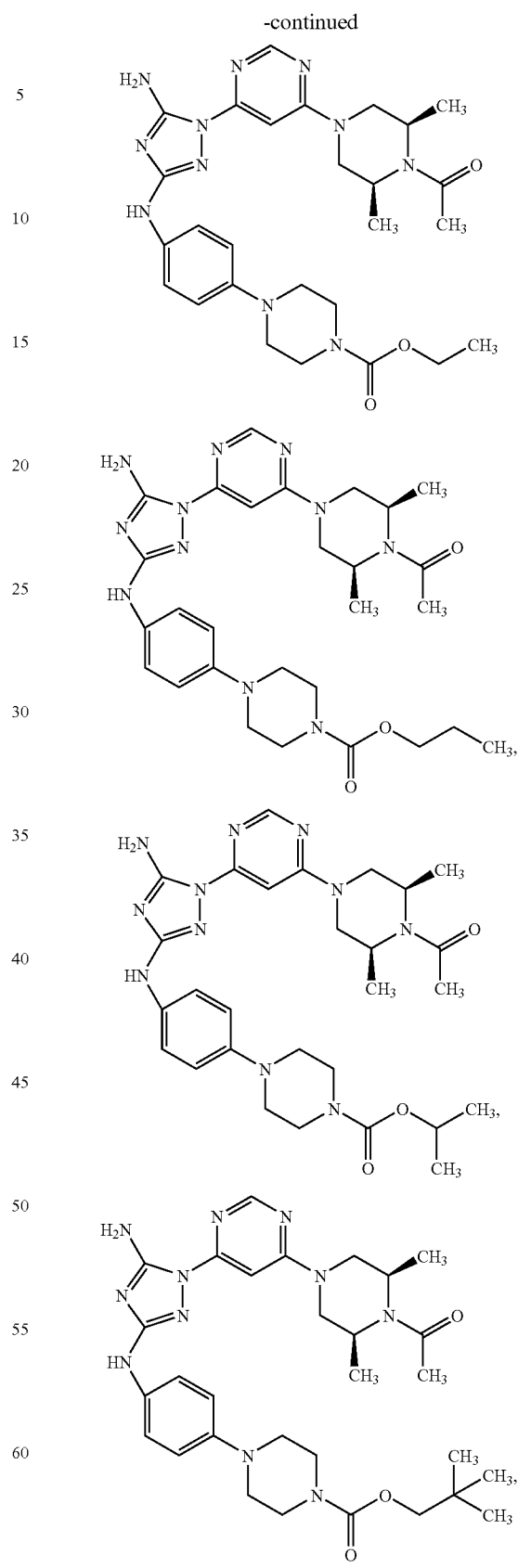

-continued
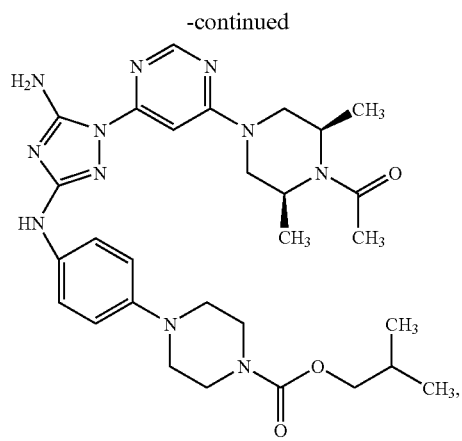
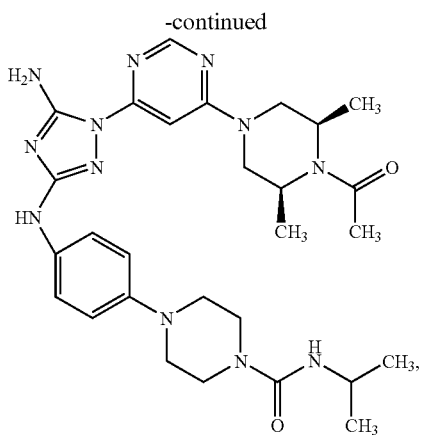
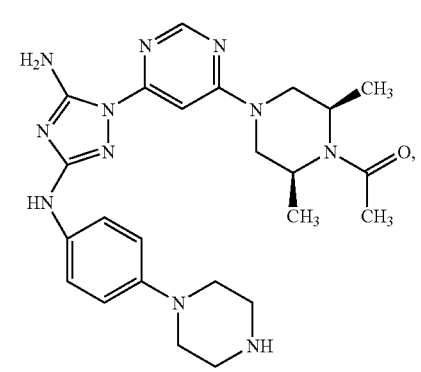
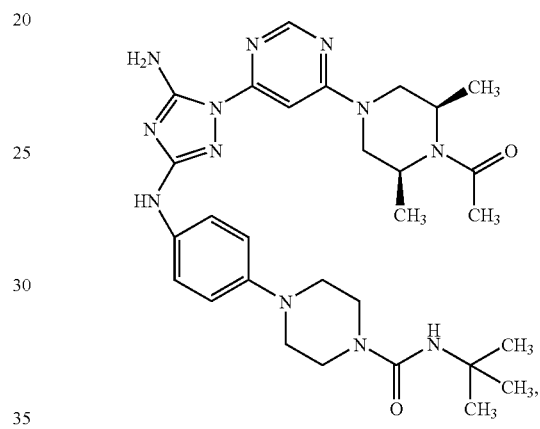
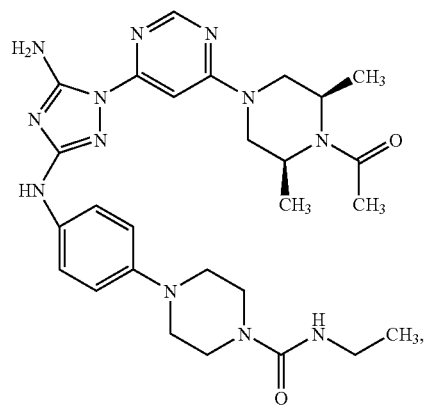
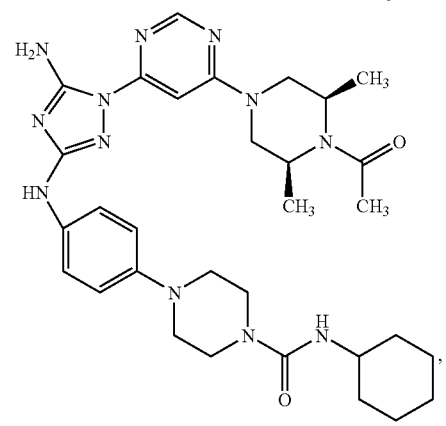
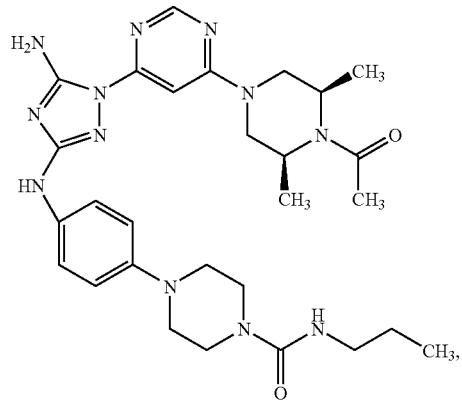
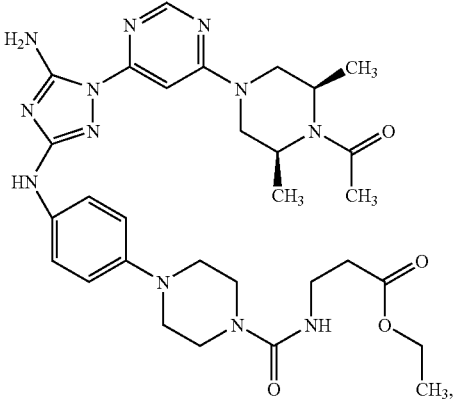

189
-continued
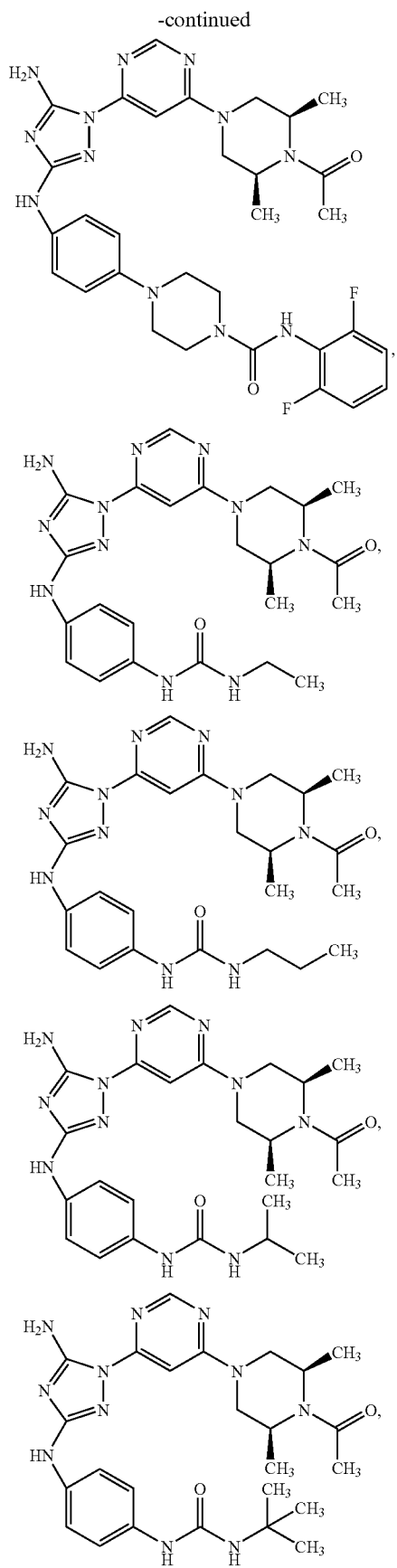
190
-continued
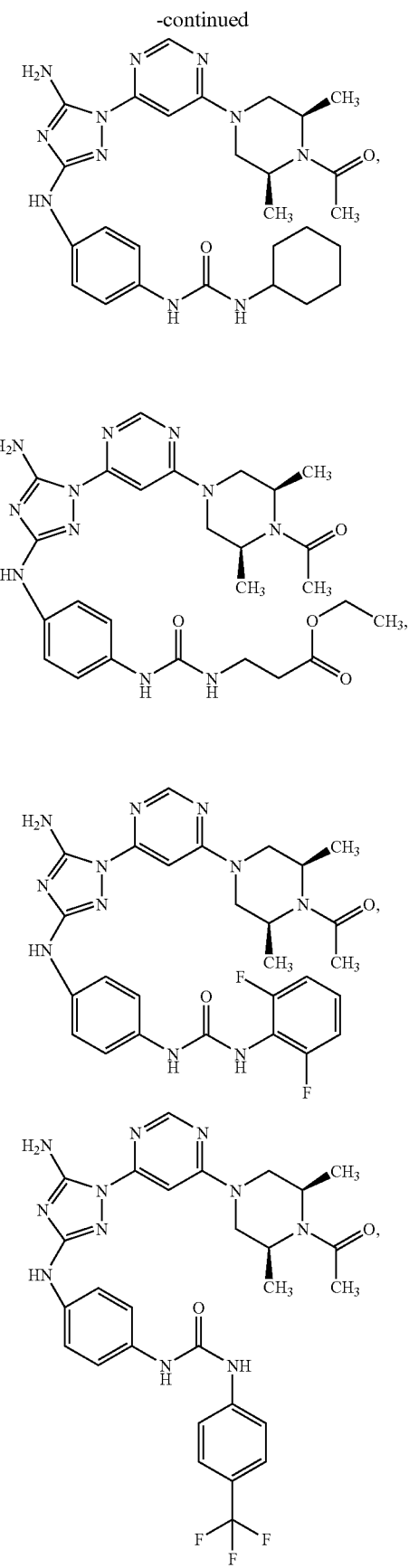

191
-continued
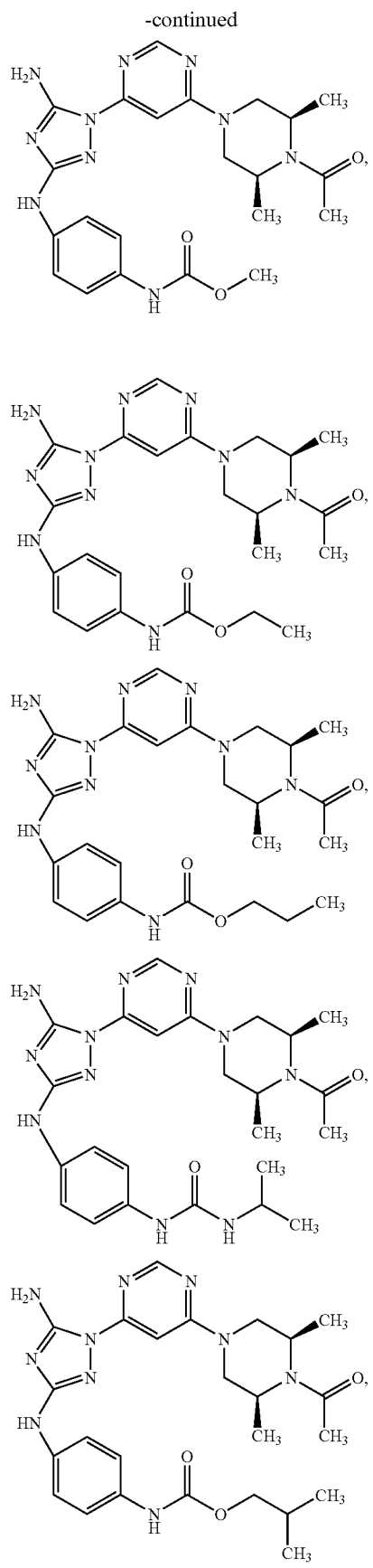
192
-continued
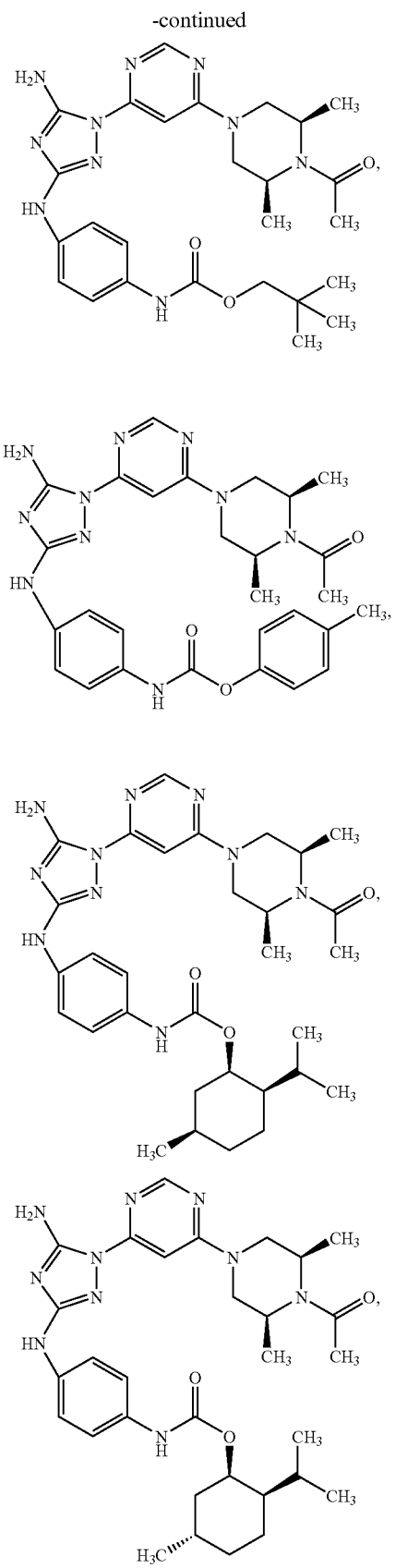

-continued

-continued
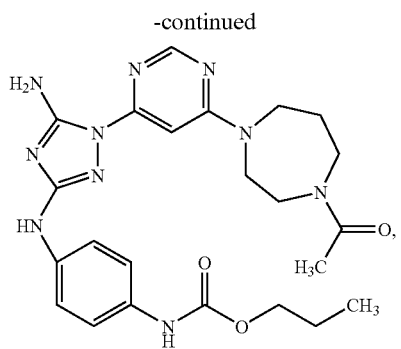
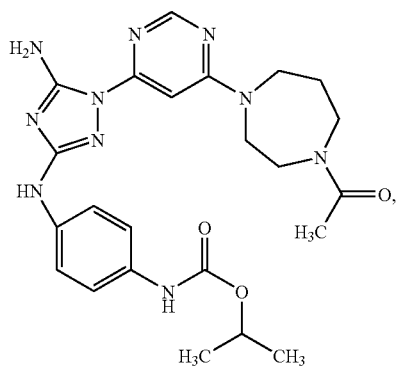
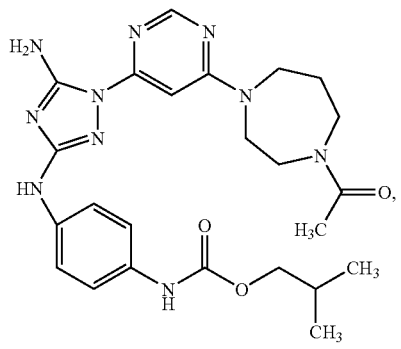
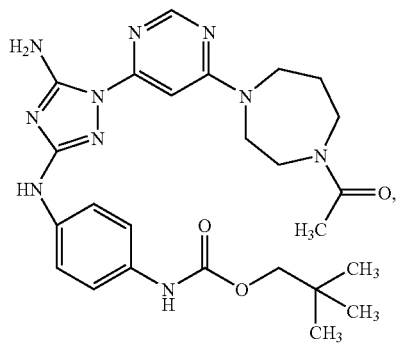
-continued
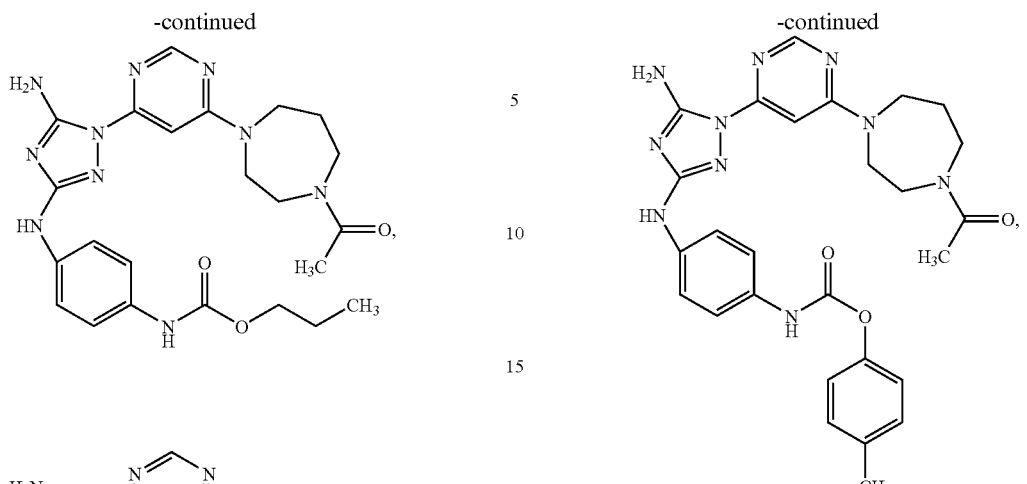
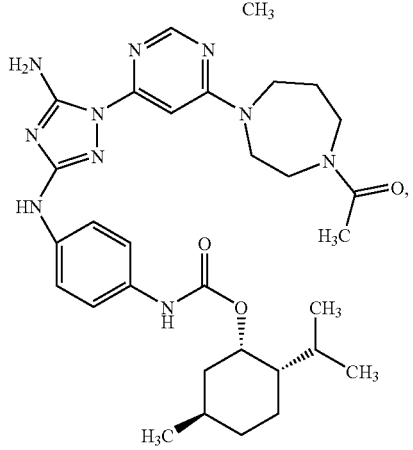
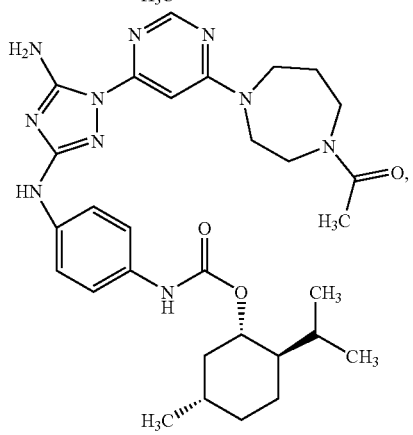
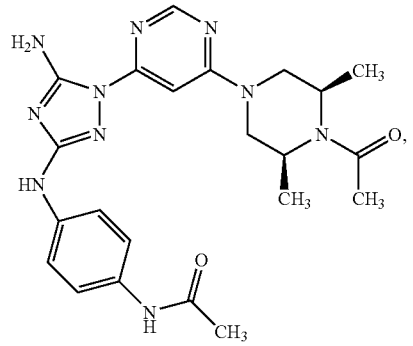

-continued
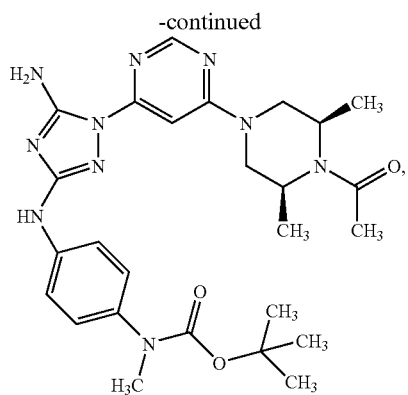
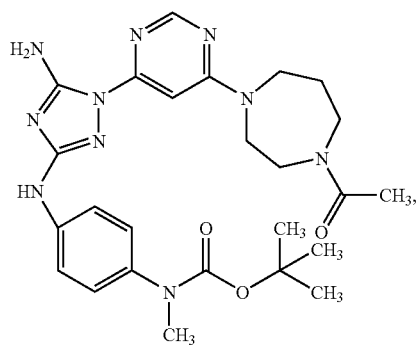
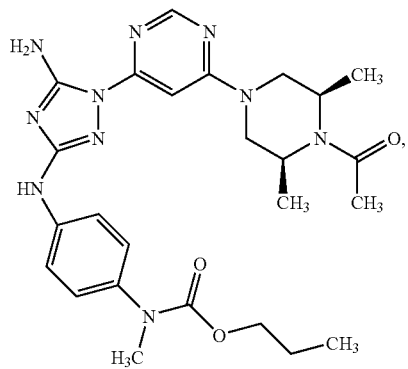
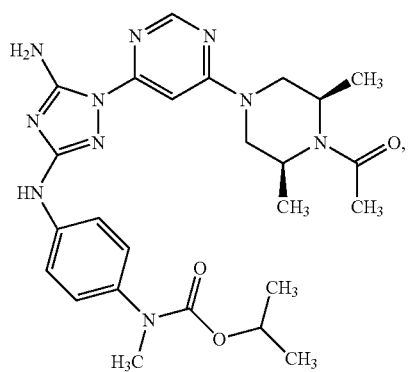
-continued
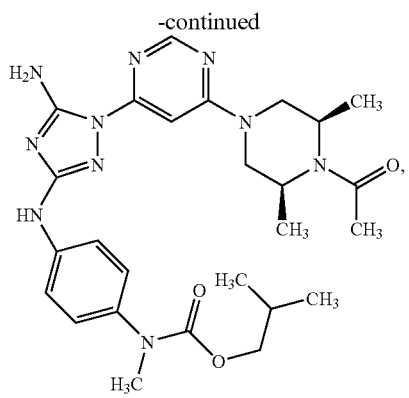
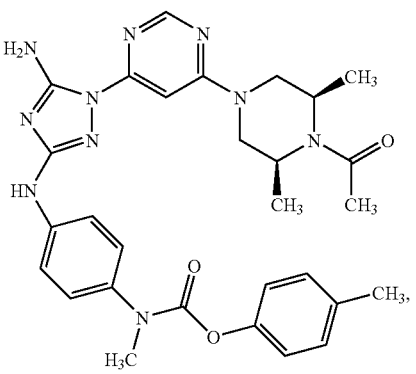
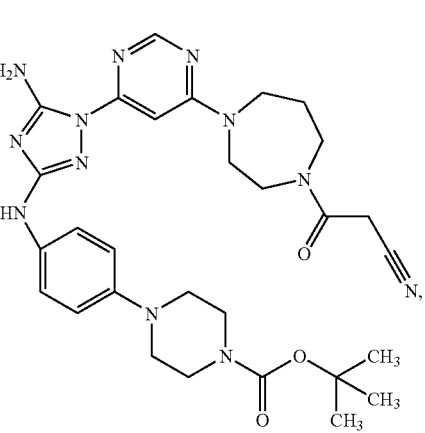
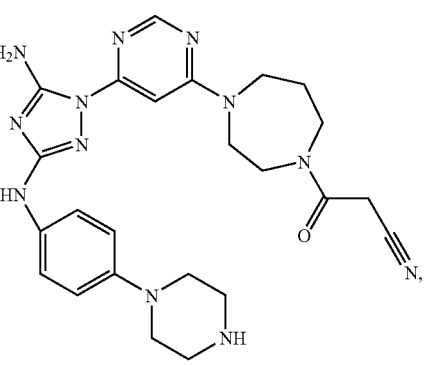

199
-continued
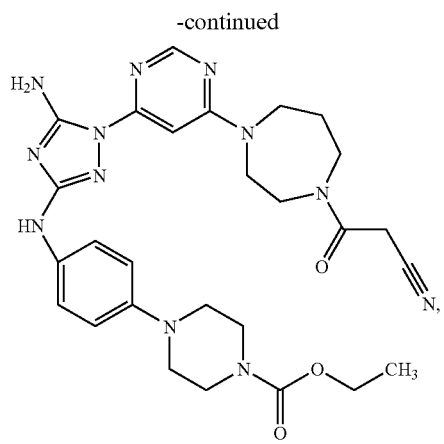
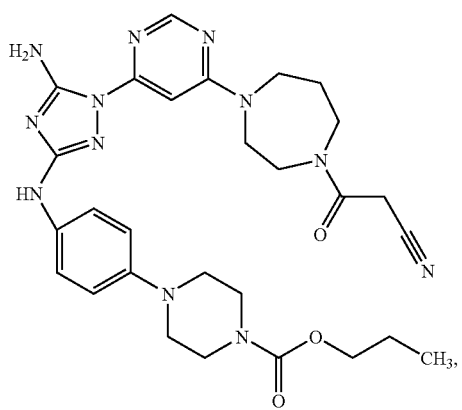
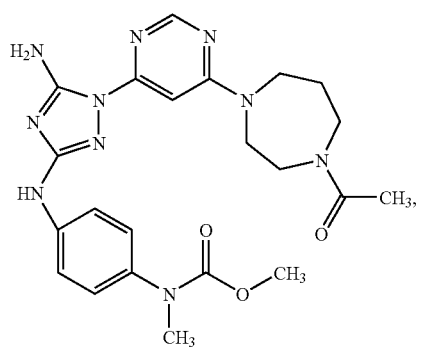
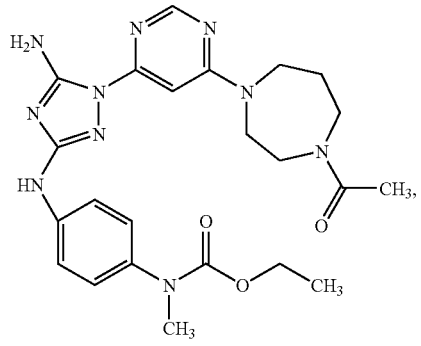
200
-continued
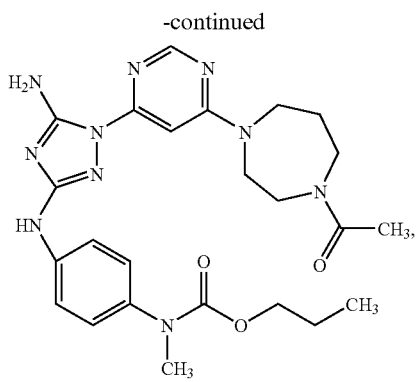
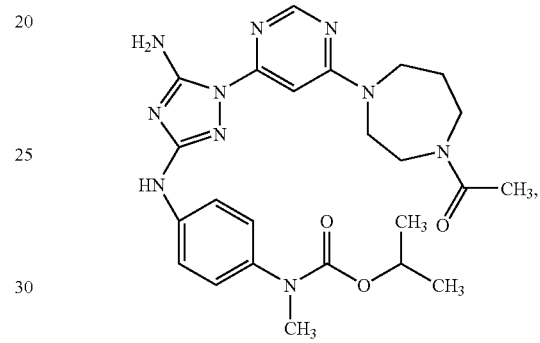
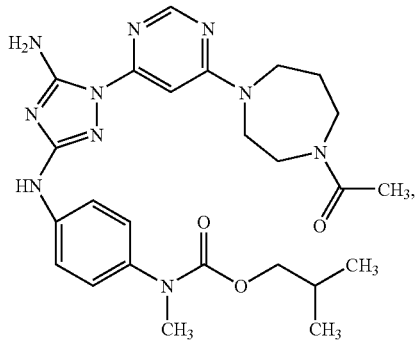
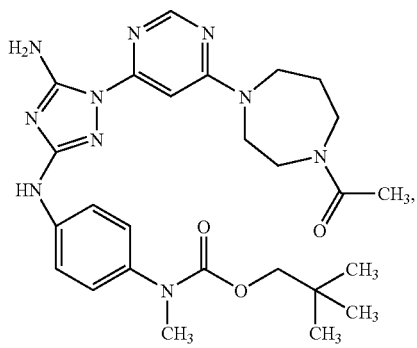

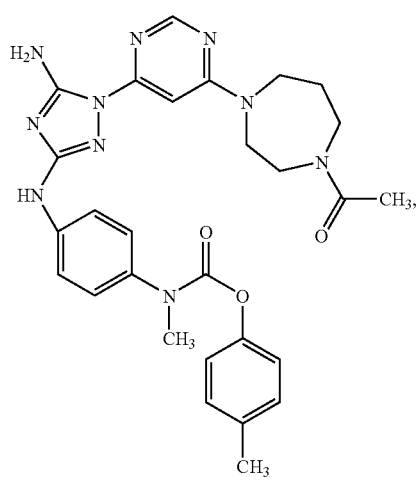
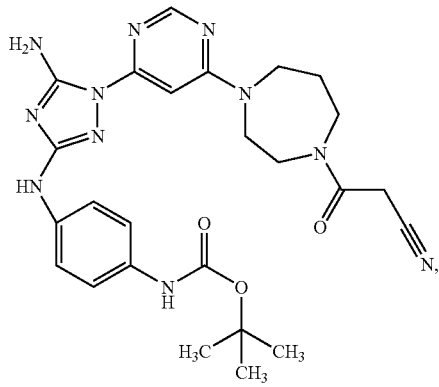
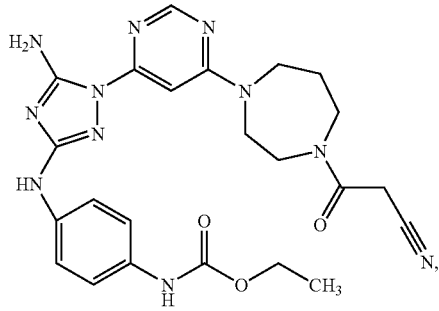
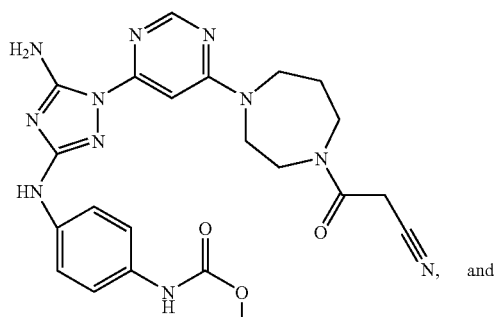
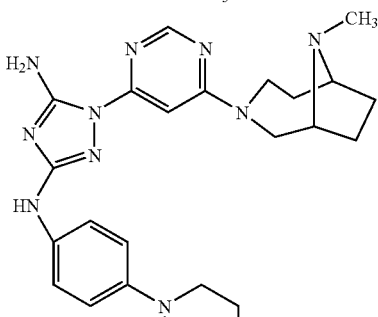

12. A composition comprising the compound according to claim 1 and a pharmaceutically acceptable carrier, adjuvant, or vehicle.

13. The composition according to claim 12, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

14. The composition according to claim 13, wherein said therapeutic agent is an immunomodulatory or immunosuppressive agent.

15. A method of inhibiting JAK2 or JAK3 kinase activity in a biological sample, comprising contacting said biological sample with the compound according to claim 1 or a composition thereof.

* * * * *